United States Patent
Messina et al.

(10) Patent No.: US 10,400,229 B2
(45) Date of Patent: Sep. 3, 2019

(54) BACTERIAL HYALURONIDASE AND PROCESS FOR ITS PRODUCTION

(71) Applicant: FIDIA FARMACEUTICI S.P.A., Abano Terme (PD) (IT)

(72) Inventors: Luciano Messina, Abano Terme (IT); Luca Musumeci, Abano Terme (IT); Susanna Vaccaro, Abano Terme (IT)

(73) Assignee: FIDIA FARMACEUTICI S.P.A., Abano Terme (PD) (IT)

( * ) Notice: Subject to any disclaimer, the term of this patent is extended or adjusted under 35 U.S.C. 154(b) by 0 days.

(21) Appl. No.: 15/728,959

(22) Filed: Oct. 10, 2017

(65) Prior Publication Data
US 2018/0362949 A1 Dec. 20, 2018

Related U.S. Application Data

(62) Division of application No. 14/899,219, filed as application No. PCT/IB2014/062193 on Jun. 13, 2014, now Pat. No. 9,822,351.

(30) Foreign Application Priority Data

Jun. 17, 2013 (IT) .............................. M12013A0992

(51) Int. Cl.
*C12N 9/26* (2006.01)
*A61K 38/00* (2006.01)

(52) U.S. Cl.
CPC .... *C12N 9/2474* (2013.01); *C12Y 302/01035* (2013.01); *A61K 38/00* (2013.01)

(58) Field of Classification Search
None
See application file for complete search history.

(56) References Cited

U.S. PATENT DOCUMENTS 5,643,758 A 7/1997 Guan et al.
9,822,351 B2 * 11/2017 Messina ......... C12Y 302/01035

FOREIGN PATENT DOCUMENTS

| CN | 101633931 A | 1/2010 |
| EP | 0005751 A1 | 12/1979 |
| WO | WO 2009/037566 A2 | 3/2009 |
| WO | WO 2009/111066 A1 | 9/2009 |
| WO | WO 2010/130810 A1 | 11/2010 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Hynes et al. "Hyaluronidases of Gram-positive bacteria", XP-002538530, FEMS Microbiology Letters, 183, (2000), 201-207.
International Search Report, issued in PCT/IB2014/062193, dated Nov. 17, 2014.
Sambrook et al., "Molecular Cloning: A Laboratory Manual", 2nd Edition, Cold Spring Harbor, N.Y., 1989, pp. 11.2-11.19.
Sambrook et al., "Molecular Cloning: A Laboratory Manual", 2nd Edition, Cold Spring Harbor, N.Y., 1989, pp. 8.46-8.52.
Written Opinion of the International Searching Authority, issued in PCT/IB2014/062193, dated Nov. 17, 2014.

* cited by examiner

*Primary Examiner* — Christian L Fronda
(74) *Attorney, Agent, or Firm* — Birch, Stewart, Kolasch & Birch, LLP

(57) ABSTRACT

The present invention relates to a hyaluronidase from *S. koganeiensis*, applications thereof and a method for the production thereof.

6 Claims, 29 Drawing Sheets

Figure 1:
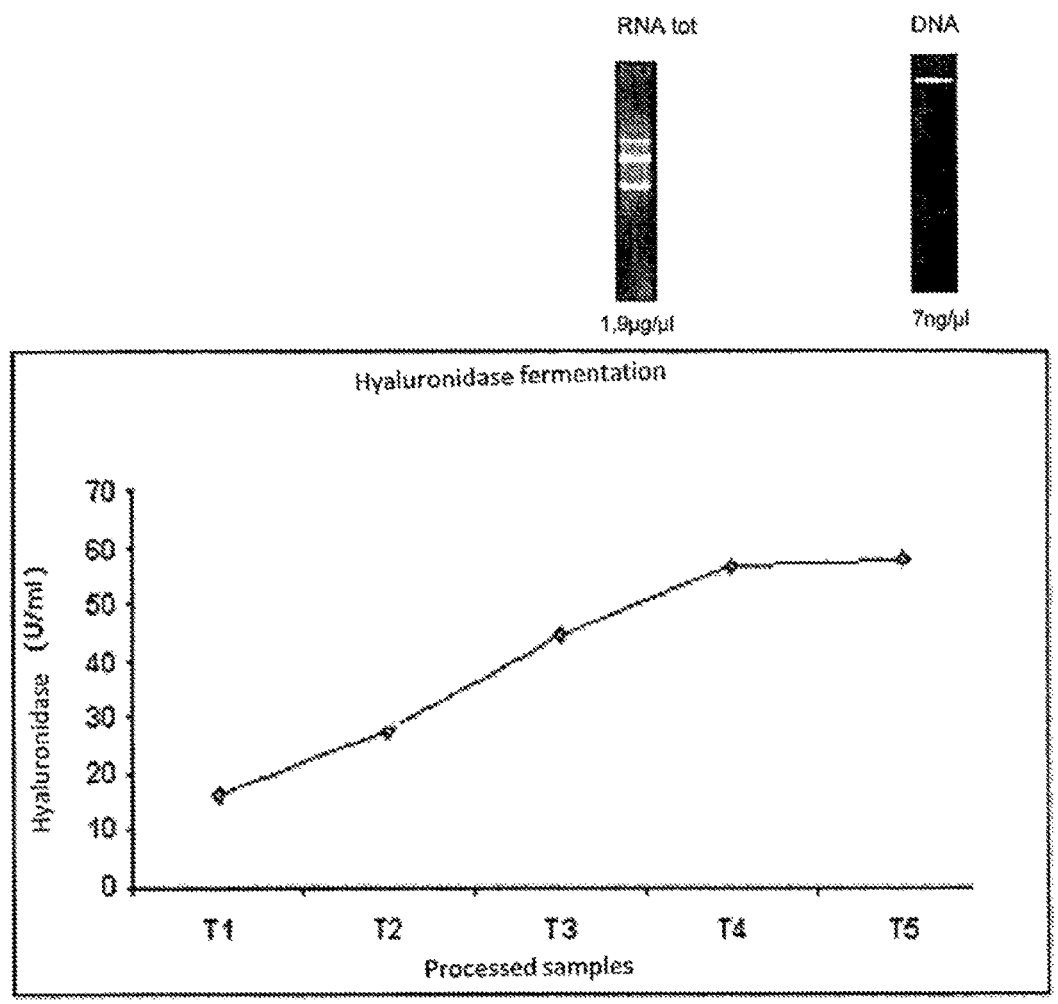

Specification includes a Sequence Listing.

```
  1  GAG AAC GCG ACG ACG ATC TTC GAC GGT CTG GTG GCC GCC GAG   45
  1   E   N   A   T   T   I   F   D   G   L   V   A   A   E   15

46  AGA TTC AGC GCG GAC ACA CTG GAG GCC GCC TTC CTC AAG ACG   90
 16   R   F   S   A   D   T   L   E   A   A   F   L   K   T   30

91  ACC TCG GAG ACG AAC CAC GCG ACT ATC TAC CAG GTC GGT ACG  135
 31   T   S   E   T   N   H   A   T   I   Y   Q   V   G   T   45

136  TCG GGT GAC GGC GCG CTG AAC GTG ATC TCC GAC AAC CCG GGC  180
 46   S   G   D   G   A   L   N   V   I   S   D   N   P   G   60

181  ACC TCG GCC ATA TAC CTG TCC GGC ACC GAG ACC GCG CGT TCC ACC  225
 61   T   S   A   I   Y   L   S   G   T   E   T   A   R   S   T   75

226  CTG AAG ATC ACC CAC AGC GGG TAC GCC GAC GGC TCC GAC AAG GAC  279
 76   L   K   I   T   H   S   G   Y   A   D   G   S   D   K   D   90

271  GCC GCC GCC CTG TCG CTC GAC CTC CGC GTC GCC ACC GCC GCC  315
 91   A   A   A   L   S   L   D   L   R   V   A   T   A   A  105

316  CAG GGC ACC TAC GTG ACG GTG ACG AAC GGT CTG ACC AAG GGC AAC  360
106   Q   G   T   Y   V   T   V   T   N   G   L   T   K   G   N  120

361  CTG ATC GCC CTG TCC AAC AAC ACG GCC CTG GAC GAC TTC GTC GTC  405
121   L   I   A   L   S   N   N   T   A   L   D   D   F   V   V  135

406  AAG GGC ACC GGC CGC ATC GGC GTC GGC ATC GAC CGC GCG GCC ACG  450
136   K   G   T   G   R   I   G   V   G   I   D   R   A   A   T  150

451  CCG CGT GCC CAG GTC GAC ATC GTG CAG CGG GGC GAC GCC CTC GCC  495
151   P   R   A   Q   V   D   I   V   Q   R   G   D   A   L   A  165

496  GCG CTC CTG GTG GAG GGC TCG GTA GAG ATC GGG AAC GCC GCG ACG  540
166   A   L   L   V   E   G   S   V   E   I   G   N   A   A   T  180

541  GTG CCG  546
181   V   P   182
```

Besides the difference of an aminoacid (underlined) all the sequences obtained by the previous proteic sequences (in bold characters) were found.

FIG.2

GENOME ENZYMATIC DIGESTION

X : PUTATIVE RESTRICTION SITE PER ENZYME

LIGATION OF THE DIGESTED ENZYME

AMPLIFICATION WITH PRIMER

INTERNAL TO THE KNOWN REGION

```
  1   ggta cgt gtg acg gct aca ccc cgc ccc aac ctc cgt aca acc att   45
  1                                                                  15

46   ccgg agt tga tcg ttg tcg ttg tcc cgg ggg act cat gcg act cat   90
 16                                                                  30

91   gcg tcc ctc cgt tca cag cag aca cga gag agt ggg gga cga cgc   135
 31                                                                  45

136   ATG CCG GTG GCA CGC AGA CTG TTT CTG GGG AGC TTC ACC GCG GGC   180
 46    M   P   V   A   R   R   L   F   L   G   S   F   T   A   G    60

181   GCG GTG ACC GTG GCG ACG GCC GCG GCG ACG GGT ACG GCC TCG GCG   225
 61    A   V   T   V   A   T   A   A   A   T   G   T   A   S   A    75
                                        MesFor2
226   GCC GGG GAG AAC GGC GCG ACG ACC TTC GAC GGC CCG GTG GCC       270
 76    A   G   E   N   G   A   T   T   F   D   G   P   V   A        90

271   GCC GAG ACG TTC AGC GCG GAC ACC ACA CTG GAG GCC GCC TTC CTC   315
 91    A   E   T   F   S   A   D   T   T   L   E   A   A   F   L   105

316   AAG ACG ACC TCG GAG ACG AAC CAC GCG GCG ACC ATC TAC CAG GCC   360
106    K   T   T   S   E   T   N   H   A   A   T   I   Y   Q   A   120

361   GGT ACG TCG GGC GAC GGC GCG GCG CTG AAC GTG ATC TCC GAC AAC   405
121    G   T   S   G   D   G   A   A   L   N   V   I   S   D   N   135

406   CCG GGC ACC TCG GCC ATG TAC CTC TCC GGC ACC GAG ACC GCG CGC   450
136    P   G   T   S   A   M   Y   L   S   G   T   E   T   A   R   150
                                        MesINTf
451   GGC ACC CTG AAG ATC ACC CAC CGC GGT TAC GCC GAC GGC TCC GAC   495
151    G   T   L   K   I   T   H   R   G   Y   A   D   G   S   D   165

496   AAG GAC GCC GCC GCC CTG TCG CTC GAC CTC CGC GTG GCC GGC ACC   540
166    K   D   A   A   A   L   S   L   D   L   R   V   A   G   T   180
                                MesINTr
541   GCC GCC CAG GGC ATC TAC GTC ACG GCG ACG AAC GGC CCG ACC AAG   585
181    A   A   Q   G   I   Y   V   T   A   T   N   G   P   T   K   195

586   GGC AAC CTG ATC GCC CTG CGC AAC AAC ACC GGC CTG GAC GAC TTC   630
196    G   N   L   I   A   L   R   N   N   T   G   L   D   D   F   210

631   GTC GTC AAG GGC ACC GGC CGC ATC GGC GTC GGC ATC GAC CGC GCG   675
211    V   V   K   G   T   G   R   I   G   V   G   I   D   R   A   225

676   GCC ACG CCC CGC GCC CAG GTC CAC ATC GTC CAG CGG GGC GAG GCC   720
226    A   T   P   R   A   Q   V   H   I   V   Q   R   G   E   A   240

721   CTC GCC GCG CTC CTG GTG GAG GGC TCG GTA CGC ATC GGG AAC GCC   765
241    L   A   A   L   L   V   E   G   S   V   R   I   G   N   A   255

766   GCG ACG GTA CCG ACG TCG GTG GAC AGC TCG GGC GGC GCC CTG       810
256    A   T   V   P   T   S   V   D   S   S   G   G   A   L       270

811   TAC GCG TCG GGC GCC CTG CTG TGG CGC GGC TCC AAC GGC ACG       855
271    Y   A   S   G   A   L   L   W   R   G   S   N   G   T       285

856   GTC ACG ACG ATC GCA CCG GCG tga agt aca ggc gag aac agt gca   900
286    V   T   T   I   A   P   A   *                               300

901   gtt gac gcc cga aga act gtt tcg cgg gag   930
301
```

Nucleic acids:
- In small letters the not encoding region found in 5' and in 3'.
- In italic letters the encoding region in 5' and 3' found with these last processing steps.
- In bold letters the START and STOP codons.
- In underlined letters the sequence corresponding to oligo in 5' MesFor2 (in bold letters the nucleotidic and conservative sequences) and MesINTf/MesINTr.
- In underlined and bold letters the restriction sites per KpnI.

Aminoacids:
- In bold letters the region corresponding to the results of the previous proteic sequencing.
- In bold letters the regions corresponding to the leader peptide found in this last processing step.

FIG.4

```
3    acc att cgg agt tga tcg ttg tcg ttg tcc cgg ggg act cat gcg   47
0                                                                  14

48   act cat gcg tcc ctc cgt tca cag cag aca cga gag agt ggg gga   92
15                                                                 29

93   cga cgc ATG CCG GTG GCA CGC AGA CTG TTT CTG GCG AGC TTC ACC  137
30        M   P   V   A   R   R   L   F   L   G   S   F   T       44
          ‾   ‾   ‾   ‾   ‾   ‾   ‾   ‾   ‾   ‾   ‾   ‾   ‾

138  GCG GGC GCG GTG ACC GTG GCG ACG GCC GCC GCG ACG GGT ACG GCC  182
45   A   G   A   V   T   V   A   T   A   A   A   T   G   T   A   59
     ‾   ‾   ‾   ‾   ‾   ‾   ‾   ‾   ‾   ‾   ‾   ‾   ‾   ‾   ‾

183  TCG GCG GCC GGG GAG AAC GGC GCG ACG ACC TTC GAC GGC CCG      227
60   S   A   G   E   N   G   A   T   T   F   D   G   P           74
     ‾

228  GTG GCC GCC GAG AGG TTC AGC GCG GAC ACC ACA CTG GAG GCC GCC  272
75   V   A   A   E   R   F   S   A   D   T   T   L   E   A   A   89

273  TTC CTC AAG ACG ACC TCG GAG ACG AAC CAC GCG GCG ACC ATC TAC  317
90   F   L   K   T   T   S   E   T   N   H   A   A   T   I   Y   104

318  CAG GCC GGT ACG TCG GGC GAC GCC GCG GCG CTG AAC GTG ATC TCC  362
105  Q   A   G   T   S   G   D   A   A   A   L   N   V   I   S   119

363  GAC AAC CCG GGC ACC TCG GCC ATG TAC CTC TCC GGC ACC GAG ACC  407
120  D   N   P   G   T   S   A   M   Y   L   S   G   T   E   T   134

408  GCG AAC GGC ACC CTG AAG ATC ACC CAC CGC GGG TAC GCC GAC GGT  452
135  A   N   G   T   L   K   I   T   H   R   G   Y   A   D   G   149

453  TCC GAC AAG GAC GCC GCC GCC CTG TCG CTC GAC CTC CGC GTG GCC  497
150  S   D   K   D   A   A   A   L   S   L   D   L   R   V   A   164

498  GGC ACC GCC GCC CAG GGC ATC TAC GTC ACG GCG ACG AAC GGC CCG  542
165  G   T   A   A   Q   G   I   Y   V   T   A   T   N   G   P   179

543  ACC AAG GGC AAC CTG ATC GCC CTG CGC AAC AAC ACG GGC CTG GAC  587
180  T   K   G   N   L   I   A   L   R   N   N   T   G   L   D   194

588  GAC TTC GTC GTC AAG GGC ACC GGC CGC ATC GGC GTC GGC ATC GAC  632
195  D   F   V   V   K   G   T   G   R   I   G   V   G   I   D   209

633  CGC GCG GCC ACG CCC CGC GCG CAG GTC AAC ATC GTC CAG CGG GGC  677
210  R   A   A   T   P   R   A   Q   V   N   I   V   Q   R   G   224

678  GAC GCC CTG GCC GCG CTC CTG GTG GAG GGC TCG GTA AAC ATC GGG  722
225  D   A   L   A   A   L   L   V   E   G   S   V   N   I   G   239

723  AAC GCC GCG ACG GTA CCG ACG TCG GTG GAC AGC TCG GGC GGC GGC  767
240  N   A   A   T   V   P   T   S   V   D   S   S   G   G   G   254

768  GCC CTG TAC GCG TCG GGC GCC CTG CTG TGG CGC GGC TCC AAC      812
255  A   L   Y   A   S   G   A   L   L   W   R   G   S   N       269

813  GGC ACG GTC ACG ACG ATC GCA CCG GCG tga agt aca gga gag aac  857
270  G   T   V   T   T   I   A   P   A   *                       284

858  agt gca gtt gac   869
285                   288
```

- in underlined letters the region corresponding to the leader peptide.
- in bold letters the aminoacidic sequence corresponding to mature hyaluronidase.
- in bold and small letters the nucleotidic sequence of the primers utilized for the isolation.

FIG.5

CLUSTAL 2.1 multiple sequence alignment

```
S.pristinaespiralis    MSVSRRLFLGSFTAGAVTVAAGAAAIPARAAEADGPITTFDGFVAEGFRIDSIVKSAFF  60
S.tsukubaensis         MAVNRRLFLGGFTAGAVTVAAG-TATPAAAAAQSPTTTFDGFVAERPSTNGTVNRAFL  59
S.koganeiensis         MPVARRLFLGSFTAGAVTVATAARTGIASAAGENGATTFDGFVAERPSADTTIERAFL  60
Actinoplanes           MAVARRLFLGSFTAGAVTVALGFST---PAAAET-ITTTPGFVVSQRFSTLGTIESAYT  56
                       *.: ******.********  .  :    . ** ** . *.*.*. *   .:::*:.*:*;

S.pristinaespiralis    KTISTTEEAVTAYQRSTSGSGVALNVVSKNPGDSAMYLSGIEKAHGTLKISHIGHADGSD 120
S.tsukubaensis         KTISTTEEAAVYQRSTSGSGVALNTYSDNPDNSAVYLIGREKTRGTLKISHIGHADGSD 119
S.koganeiensis         KTISETNEAAIIYQRGTSGSGAALDVLSDNPGTSAMYLSHIETARGTLKITRGYADGSD 120
Actinoplanes           KTISVIDNAVTVYQAAASERGFALNVYGNEENSAMYLSGIETGRGTLKITRGYDDGSD 116
                       **** *:.*.*  *** .:** *.***::.*       ** .* *  ;*****:* * ****

S.pristinaespiralis    RYASRASIDLLTAGTAAQGIFYKADGPTIGSILICLRNH-ARDDFVVKGSGRVGIGRSVG 179
S.tsukubaensis         RDRAAVSIDLKTAGTATQGIFLIATDGAITGSILICLRNN-GRDDFVVKGSGRVGIGLAVG 178
S.koganeiensis         KERAALSLDLRVAGTAAQGIYYTATNGRTKGNLIALRNHTGLDDFVVESTGRISVGIDRA 180
Actinoplanes           RSRAAISIDLRIAGTAAQGIYLIATNGPTIGSLIARLNNFCREDFIVTGASGRIGIGVNRG 176
                         . *:*:****  ,****:****::.*  :*.*.*..****       . ***:*.*:*:*:

S.pristinaespiralis    GNPWRQLHVVQQPGTDSALMVEGSTVRVVDVASAPTGVDSRGGGVLYAENGALKKRGSDNI 239
S.tsukubaensis         SAFRSQLHVVQRFGADSRLMVPGAVRIVDAATVPTAVDSKGGSTILYAQGGELMWRSANGM 238
S.koganeiensis         AIPRAQVHIVQRGDALAALLVEGSVRIGRAATVPTSVDSSGGGALVASGGCALLWRGSNGT 240
Actinoplanes           DIPRGQVHIVQRGFVPAGVLIEGVVRIANTATVPTSADSSGGGNLYRVHGALMRSANGK 236
                          . *:*;*** ..  :.::** **:.*:,**..** *** *** .* * **.:;..

S.pristinaespiralis    VTTIAPA 246
S.tsukubaensis         VIRIASA 245
S.koganeiensis         VTTIAPA 247
Actinoplanes           VIQIASA 243
                       ** **.*
```

☐ Bacterial hyaluronidase (Hyaluronidase_1) functional domain

\*   Conserved aminoacidic residues

:   Aminoacidic residues with strongly similar properties

.   Aminoacidic residues with strongly similar properties

FIG.6A

FIG.6B

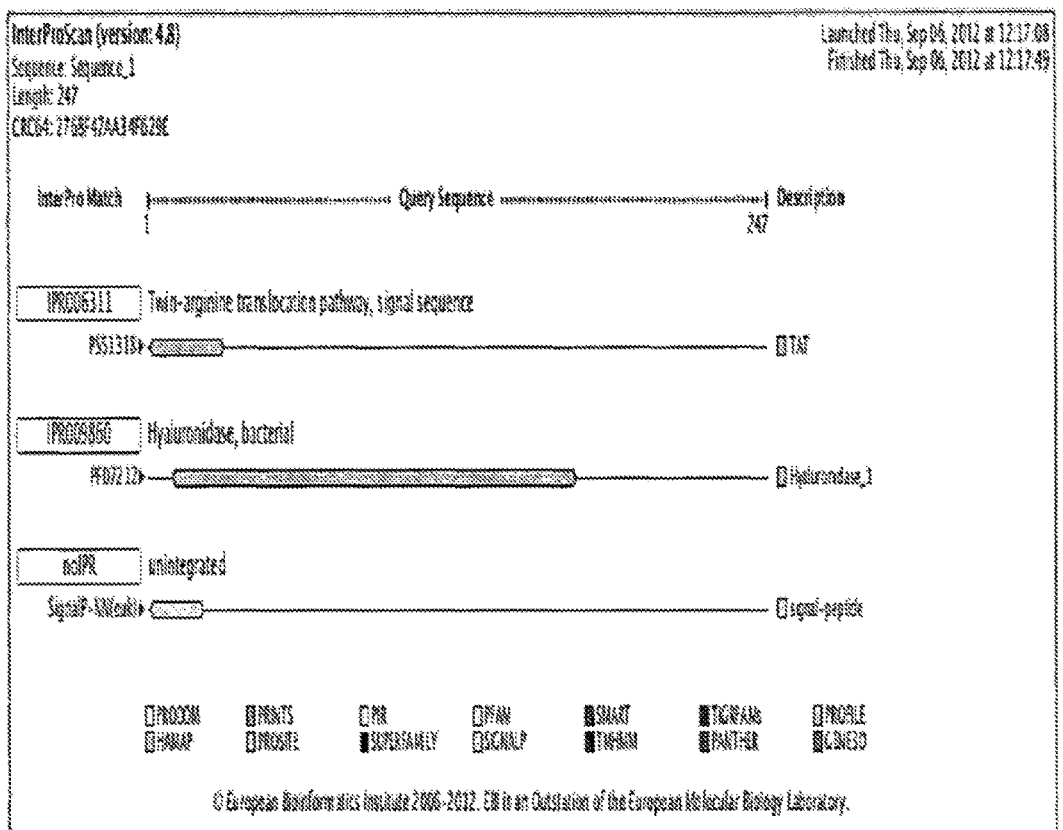
Aminoacidic sequence of Hyaluronidase from S. Koganeiensis:
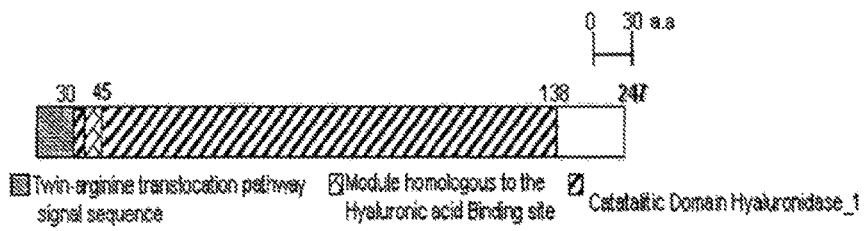
FIG.7A

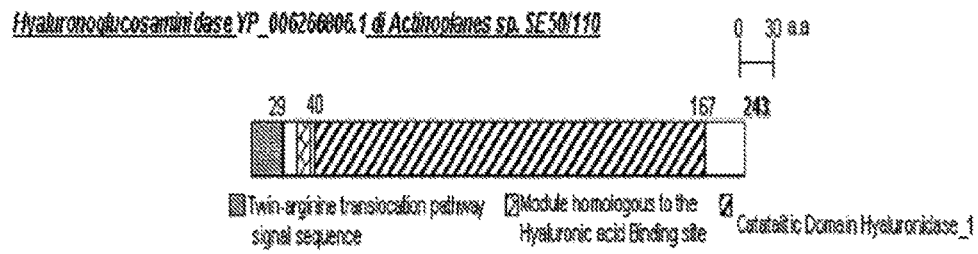
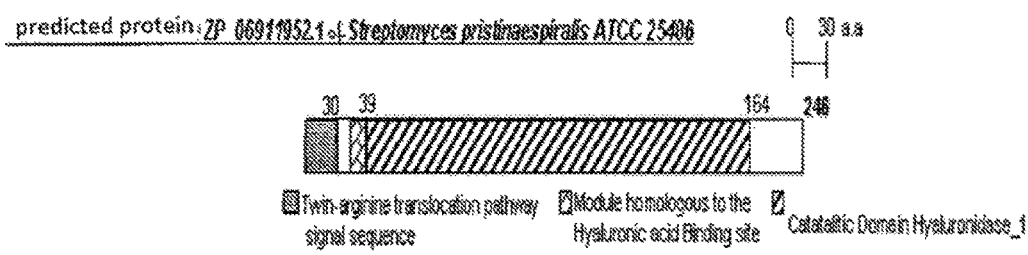
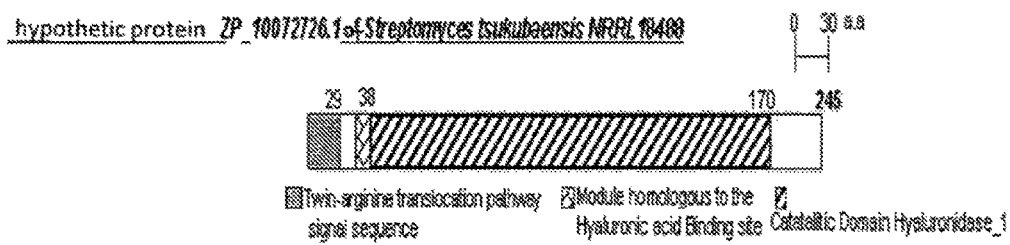
FIG.7B

FIG.13C

SEQUENCE LISTING

```
<160> NUMBER OF SEQ ID NOS: 52

<210> SEQ ID NO 1
<211> LENGTH: 15
<212> TYPE: PRT
<213> ORGANISM: Streptomyces koganeiensis

<400> SEQUENCE: 1

Ala Gly Glu Asn Gly Ala Thr Thr Thr Phe Asp Gly Pro Val Ala
1               5                   10                  15

<210> SEQ ID NO 2
<211> LENGTH: 27
<212> TYPE: PRT
<213> ORGANISM: Streptomyces koganeiensis

<400> SEQUENCE: 2

Arg Phe Ser Ala Asp Thr Thr Ile Glu Ala Ala Phe Ile Lys Thr Thr
1               5                   10                  15

Ser Glu Thr Ile His Ala Ala Thr Ile Tyr Lys
            20                  25

<210> SEQ ID NO 3
<211> LENGTH: 18
<212> TYPE: PRT
<213> ORGANISM: Streptomyces koganeiensis

<400> SEQUENCE: 3

Gly Tyr Ala Asp Gly Ser Asp Lys Asp Ala Ala Ala Leu Ser Leu Asp
1               5                   10                  15

Leu Arg

<210> SEQ ID NO 4
<211> LENGTH: 8
<212> TYPE: PRT
<213> ORGANISM: Streptomyces koganeiensis

<400> SEQUENCE: 4

Ala Gln Val His Ile Val Gln Arg
1               5

<210> SEQ ID NO 5
<211> LENGTH: 17
<212> TYPE: PRT
<213> ORGANISM: Streptomyces koganeiensis
```

<400> SEQUENCE: 5

Ile Gly Asn Ala Ala Thr Val Pro Thr Ser Val Asp Ser Ser Gly Gly
1               5                   10                  15

Gly

<210> SEQ ID NO 6
<211> LENGTH: 26
<212> TYPE: DNA
<213> ORGANISM: Streptomyces koganeiensis

<400> SEQUENCE: 6
ggagaacggg gcgacgacga cgttcg                                    26

<210> SEQ ID NO 7
<211> LENGTH: 26
<212> TYPE: DNA
<213> ORGANISM: Streptomyces koganeiensis

<400> SEQUENCE: 7
gtcggcaccg tcgccgcgtt cccgat                                    26

<210> SEQ ID NO 8
<211> LENGTH: 546
<212> TYPE: DNA
<213> ORGANISM: Streptomyces koganeiensis

<400> SEQUENCE: 8
gagaacgggg cgacgacgac gttcgacggc ccggtggccg ccgagaggtt cagcgcggac    60
accacactgg aggccgcctt cctcaagacg acctcggaga cgaaccacgc ggcgaccatc   120
taccaggccg gtacgtcggg cgacggcgcg gcgctgaacg tgatctccga caacccgggc   180
acctcggcca tgtacctctc cggcaccgag accgcgcgcg gcaccctgaa gatcacccac   240
cgcgggtacg ccgacggctc cgacaaggac gccgccgccc tgtcgctcga cctccgcgtg   300
gccggcaccg ccgcccaggg catctacgtc acggcgacga acggcccgac caagggcaac   360
ctgatcgccc tgcgcaacaa cacgggcctg acgacttcg tcgtcaaggg caccggccgc   420
atcggcgtcg gcatcgaccg cgcggccacg ccccgcgccc aggtccacat cgtccagcgg   480
ggcgacgccc tcgccgcgct cctggtggag ggctcggtac gcatcgggaa cgccgcgacg   540
gtgccg                                                             546

<210> SEQ ID NO 9
<211> LENGTH: 18
<212> TYPE: DNA
<213> ORGANISM: Streptomyces koganeiensis

<400> SEQUENCE: 9
cgggagaagg gtgaacgc                                                 18

<210> SEQ ID NO 10
<211> LENGTH: 19
<212> TYPE: DNA
<213> ORGANISM: Streptomyces koganeiensis

<400> SEQUENCE: 10
ctccgcgacc agttcttcg                                                19

```
<210> SEQ ID NO 11
<211> LENGTH: 24
<212> TYPE: DNA
<213> ORGANISM: Streptomyces koganeiensis

<400> SEQUENCE: 11
ggcatctacg tcacggcgac gaac                                          24

<210> SEQ ID NO 12
<211> LENGTH: 25
<212> TYPE: DNA
<213> ORGANISM: Streptomyces koganeiensis

<400> SEQUENCE: 12
cgtacccgcg gtgggtgatc ttcag                                         25

<210> SEQ ID NO 13
<211> LENGTH: 930
<212> TYPE: DNA
<213> ORGANISM: Streptomyces koganeiensis

<400> SEQUENCE: 13
ggtacctgtg acggctacac cccgccccaa cctccgtaca accattcgga gttgatcgtt    60
gtcgttgtcc cggggactc atgcgactca tgcgtccctc cgttcacagc agacacgaga    120
gagtggggga cgacgcatgc cggtggcacg cagactgttt ctggggagct tcaccgcggg   180
cgcggtgacc gtggcgacgg ccgccgcgac gggtacggcc tcggcggccg gggagaacgg   240
cgcgacgacg accttcgacg gcccggtggc cgccgagagg ttcagcgcgg acaccacact   300
ggaggccgcc ttcctcaaga cgacctcgga gacgaaccac gcggcgacca tctaccaggc   360
cggtacgtcg ggcgacggcg cggcgctgaa cgtgatctcc gacaacccgg gcacctcggc   420
catgtaccgc tccggcaccg agaccgcgcg cggcaccctg aagatcaccc accgcgggta   480
cgccgacggc tccgacaagg acgccgccgc cctgtcgctc gacctccgcg tggccggcac   540
cgccgcccag ggcatctacg tcacggcgac gaacggcccg accaagggca acctgatcgc   600
cctgcgcaac aacacgggcc tggacgactt cgtcgtcaag ggcaccggcc gcatcggcgt   660
cggcatcgac cgcgcgggcca cgccccgcgc ccaggtccac atcgtccagc ggggcgacgc   720
cctcgccgcg ctcctggtgg agggctcggt acgcatcggg aacgccgcga cggtaccgac   780
gtcggtggac agctcgggcg gcggcgcct gtacgcgtcg gcggcgccc tgctgtggcg   840 cggctccaac ggcacggtca cgacgatcgc accggcgtga agtacaggag agaacagtgc   900
agttgacgcc cgaagaactg tttcgcggga                                    930

<210> SEQ ID NO 14
<211> LENGTH: 21
<212> TYPE: DNA
<213> ORGANISM: Streptomyces koganeiensis

<400> SEQUENCE: 14
accattcgga gttgatcgtt g                                             21

<210> SEQ ID NO 15
<211> LENGTH: 21
<212> TYPE: DNA
<213> ORGANISM: Streptomyces koganeiensis

<400> SEQUENCE: 15
gtcaactgca ctgttctctc c                                             21
```

<210> SEQ ID NO 16
<211> LENGTH: 867
<212> TYPE: DNA
<213> ORGANISM: Streptomyces koganeiensis

<400> SEQUENCE: 16

```
accattcgga gttgatcgtt gtcgttgtcc cggggactc atgcgactca tgcgtccctc      60
cgttcacagc agacacgaga gagtggggga cgacgcatgc cggtggcacg cagactgttt    120
ctggggagct tcaccgcggg cgcggtgacc gtggcgacgg ccgccgcgac gggtacggcc    180
tcggcggccg gggagaacgg cgcgacgacg accttcgacg gcccggtggc cgccgagagg    240
ttcagcgcgg acaccacact ggaggccgcc ttcctcaaga cgacctcgga gacgaaccac    300
gcggcgacca tctaccaggc cggtacgtcg ggcgacggcg cggcgctgaa cgtgatctcc    360
gacaacccgg gcacctcggc catgtacctc tccggcaccg agaccgcgcg cggcaccctg    420
aagatcaccc accgcgggta cgccgacggc tccgacaagg acgccgccgc cctgtcgctc    480
gacctccgcg tggccggcac cgccgcccag ggcatctacg tcacggcgac gaacggcccg    540
accaagggca acctgatcgc cctgcgcaac aacacgggcc tggacgactt cgtcgtcaag    600
ggcaccggcc gcatcggcgt cggcatcgac cgcgcggcca cgccccgcgc ccaggtccac    660
atcgtccagc ggggcgacgc cctcgccgcg ctcctggtgg agggctcggt acgcatcggg    720
aacgccgcga cggtaccgac gtcggtggac agctcgggcg gcggcgccct gtacgcgtcg    780
ggcggcgccc tgctgtggcg cggctccaac ggcacggtca cgacgatcgc accggcgtga    840
agtacaggag agaacagtgc agttgac                                          867
```

<210> SEQ ID NO 17
<211> LENGTH: 744
<212> TYPE: DNA
<213> ORGANISM: Streptomyces koganeiensis

<400> SEQUENCE: 17

```
atgccggtgg cacgcagact gtttctgggg agcttcaccg cgggcgcggt gaccgtggcg      60
acggccgccg cgacgggtac ggcctcggcg gccggggaga acggcgcgac gacgaccttc    120
gacggcccgg tggccgccga gaggttcagc gcggacacca cactggaggc cgccttcctc    180
aagacgacct cggagacgaa ccacgcggcg accatctacc aggccggtac gtcgggcgac    240
ggcgcggcgc tgaacgtgat ctccgacaac ccgggcacct cggccatgta cctctccggc    300
accgagaccg cgcgcggcac cctgaagatc acccaccgcg ggtacgccga cggctccgac    360
aaggacgccg ccgccctgtc gctcgacctc cgcgtggccg gcaccgccgc ccagggcatc    420
tacgtcacgg cgacgaacgg cccgaccaag ggcaacctga tcgccctgcg caacaacacg    480
ggcctggacg acttcgtcgt caagggcacc ggccgcatcg gcgtcggcat cgaccgcgcg    540
gccacgcccc gcgcccaggt ccacatcgtc agcggggcg acgccctcgc cgcgctcctg    600
gtggagggct cggtacgcat cgggaacgcc gcgacggtac cgacgtcggt ggacagctcg    660
ggcggcggcg ccctgtacgc gtcgggcggc gccctgctgt ggcgcggctc caacggcacg    720
gtcacgacga tcgcaccggc gtga                                              744
```

<210> SEQ ID NO 18
<211> LENGTH: 247
<212> TYPE: PRT
<213> ORGANISM: Streptomyces koganeiensis

<400> SEQUENCE: 18

```
Met Pro Val Ala Arg Arg Leu Phe Leu Gly Ser Phe Thr Ala Gly Ala
1               5                   10                  15

Val Thr Val Ala Thr Ala Ala Thr Gly Thr Ala Ser Ala Ala Gly
            20                  25                  30

Glu Asn Gly Ala Thr Thr Thr Phe Asp Gly Pro Val Ala Ala Glu Arg
            35                  40                  45

Phe Ser Ala Asp Thr Thr Leu Glu Ala Ala Phe Leu Lys Thr Thr Ser
    50                  55                  60

Glu Thr Asn His Ala Ala Thr Ile Tyr Gln Ala Gly Thr Ser Gly Asp
65                  70                  75                  80

Gly Ala Ala Leu Asn Val Ile Ser Asp Asn Pro Gly Thr Ser Ala Met
                85                  90                  95

Tyr Leu Ser Gly Thr Glu Thr Ala Arg Gly Thr Leu Lys Ile Thr His
            100                 105                 110

Arg Gly Tyr Ala Asp Gly Ser Asp Lys Asp Ala Ala Leu Ser Leu
            115                 120                 125

Asp Leu Arg Val Ala Gly Thr Ala Ala Gln Gly Ile Tyr Val Thr Ala
    130                 135                 140

Thr Asn Gly Pro Thr Lys Gly Asn Leu Ile Ala Leu Arg Asn Asn Thr
145                 150                 155                 160

Gly Leu Asp Asp Phe Val Val Lys Gly Thr Gly Arg Ile Gly Val Gly
                165                 170                 175

Ile Asp Arg Ala Ala Thr Pro Arg Ala Gln Val His Ile Val Gln Arg
            180                 185                 190

Gly Asp Ala Leu Ala Ala Leu Leu Val Glu Gly Ser Val Arg Ile Gly
            195                 200                 205

Asn Ala Ala Thr Val Pro Thr Ser Val Asp Ser Ser Gly Gly Gly Ala
            210                 215                 220

Leu Tyr Ala Ser Gly Gly Ala Leu Leu Trp Arg Gly Ser Asn Gly Thr
225                 230                 235                 240

Val Thr Thr Ile Ala Pro Ala
                245
```

<210> SEQ ID NO 19
<211> LENGTH: 387
<212> TYPE: DNA
<213> ORGANISM: Streptomyces koganeiensis

<400> SEQUENCE: 19

```
ttcgacggcc cggtggccgc cgagaggttc agcgcggaca ccacactgga ggccgccttc      60
ctcaagacga cctcggagac gaaccacgcg gcgaccatct accaggccgg tacgtcgggc    120
gacggcgcgg cgctgaacgt gatctccgac aacccgggca cctcggccat gtacctctcc    180
ggcaccgaga ccgcgcgcgg caccctgaag atcacccacc gcgggtacgc cgacggctcc    240
gacaaggacg ccgccgccct gtcgctcgac ctccgcgtgg ccggcaccgc cgcccagggc    300
atctacgtca cggcgacgaa cggcccgacc aagggcaacc tgatcgccct cgcaacaac    360
acgggcctgg acgacttcgt cgtcaag                                        387
```

<210> SEQ ID NO 20
<211> LENGTH: 90
<212> TYPE: DNA
<213> ORGANISM: Streptomyces koganeiensis

<400> SEQUENCE: 20
atgccggtgg cacgcagact gtttctgggg agcttcaccg cgggcgcggt gaccgtggcg    60
acggccgccg cgacgggtac ggcctcggcg    90

<210> SEQ ID NO 21
<211> LENGTH: 217
<212> TYPE: PRT
<213> ORGANISM: Streptomyces koganeiensis

<400> SEQUENCE: 21

| Ala | Gly | Glu | Asn | Gly | Ala | Thr | Thr | Thr | Phe | Asp | Gly | Pro | Val | Ala | Ala |
|-----|-----|-----|-----|-----|-----|-----|-----|-----|-----|-----|-----|-----|-----|-----|-----|
| 1 | | | | 5 | | | | | 10 | | | | | 15 | |

| Glu | Arg | Phe | Ser | Ala | Asp | Thr | Thr | Leu | Glu | Ala | Ala | Phe | Leu | Lys | Thr |
| | | | 20 | | | | | 25 | | | | | 30 | | |

| Thr | Ser | Glu | Thr | Asn | His | Ala | Ala | Thr | Ile | Tyr | Gln | Ala | Gly | Thr | Ser |
| | | | 35 | | | | 40 | | | | | 45 | | | |

| Gly | Asp | Gly | Ala | Ala | Leu | Asn | Val | Ile | Ser | Asp | Asn | Pro | Gly | Thr | Ser |
| | 50 | | | | | 55 | | | | | 60 | | | | |

| Ala | Met | Tyr | Leu | Ser | Gly | Thr | Glu | Thr | Ala | Arg | Gly | Thr | Leu | Lys | Ile |
| 65 | | | | | 70 | | | | | 75 | | | | | 80 |

| Thr | His | Arg | Gly | Tyr | Ala | Asp | Gly | Ser | Asp | Lys | Asp | Ala | Ala | Ala | Leu |
| | | | | 85 | | | | | 90 | | | | | 95 | |

| Ser | Leu | Asp | Leu | Arg | Val | Ala | Gly | Thr | Ala | Ala | Gln | Gly | Ile | Tyr | Val |
| | | | | 100 | | | | | 105 | | | | | 110 | |

| Thr | Ala | Thr | Asn | Gly | Pro | Thr | Lys | Gly | Asn | Leu | Ile | Ala | Leu | Arg | Asn |
| | | | 115 | | | | | 120 | | | | | 125 | | |

| Asn | Thr | Gly | Leu | Asp | Asp | Phe | Val | Val | Lys | Gly | Thr | Gly | Arg | Ile | Gly |
| | 130 | | | | | 135 | | | | | 140 | | | | |

| Val | Gly | Ile | Asp | Arg | Ala | Ala | Thr | Pro | Arg | Ala | Gln | Val | His | Ile | Val |
| 145 | | | | | 150 | | | | | 155 | | | | | 160 |

| Gln | Arg | Gly | Asp | Ala | Leu | Ala | Ala | Leu | Leu | Val | Glu | Gly | Ser | Val | Arg |
| | | | | 165 | | | | | 170 | | | | | 175 | |

| Ile | Gly | Asn | Ala | Ala | Thr | Val | Pro | Thr | Ser | Val | Asp | Ser | Ser | Gly | Gly |
| | | | 180 | | | | | 185 | | | | | 190 | | |

| Gly | Ala | Leu | Tyr | Ala | Ser | Gly | Gly | Ala | Leu | Leu | Trp | Arg | Gly | Ser | Asn |
| | | | 195 | | | | | 200 | | | | | 205 | | |

| Gly | Thr | Val | Thr | Thr | Ile | Ala | Pro | Ala |
| | 210 | | | | | 215 | | |

<210> SEQ ID NO 22
<211> LENGTH: 651
<212> TYPE: DNA
<213> ORGANISM: Streptomyces koganeiensis

<400> SEQUENCE: 22
gccggggaga acggcgcgac gacgaccttc gacggcccgg tggccgccga gaggttcagc    60
gcggacacca cactggaggc cgccttcctc aagacgacct cggagacgaa ccacgcggcg   120
accatctacc aggccggtac gtcgggcgac ggcgcggcgc tgaacgtgat ctccgacaac   180
ccgggcacct cggccatgta cctctccggc accgagaccg cgcgcggcac cctgaagatc   240
acccaccgcg ggtacgccga cggctccgac aaggacgccg ccgccctgtc gctcgacctc   300
cgcgtggccg gcaccgccgc ccagggcatc tacgtcacgg cgacgaacgg cccgaccaag   360
ggcaacctga tcgccctgcg caacaacacg ggcctggacg acttcgtcgt caagggcacc   420
ggccgcatcg gcgtcggcat cgaccgcgcg gccacgcccc gcgcccaggt ccacatcgtc   480

```
cagcggggcg acgccctcgc cgcgctcctg gtggagggct cggtacgcat cgggaacgcc      540
gcgacggtac cgacgtcggt ggacagctcg ggcggcggcg ccctgtacgc gtcgggcggc      600
gccctgctgt ggcgcggctc aacggcacg gtcacgacga tcgcaccggc g               651

<210> SEQ ID NO 23
<211> LENGTH: 741
<212> TYPE: DNA
<213> ORGANISM: Streptomyces pristinaespiralis

<400> SEQUENCE: 23
atgagcgtgt cgcggaggtt gttcctcgga gggttcaccg cggggcggt gaccgtggcg       60 gcgggcgccg ccgcgacgcc ggcggcggcc gcggaggcg acggcccgac gacgacgttc      120
gacggtccgg tggtggcgga gggtttcagg acggactcca ccgtcaagtc cgccttcttc      180
aagacgacgt cgacgaccga gcacgcgtg acggcctatc aggccggcac gtccggcagc      240
ggcgtggccc tgaacgtcgt atcgaagaac ccgggtgact cggccatgta tctcagtggc      300
acggagaagg cgcacggcac gctgaagatc tcgcacacgg ccacgcgga cggctcggac      360 gagaaggcgt ccgctctgtc gatcgacctg ctgacggcgg ggacggcagc ccagggcatc      420
ttcgtgaagg cgggcaacgg gcccaccacc ggcaacctga tctgcctgcg caacaacgcc      480
cgagacgact tcgtcgtcaa gggcagcggg cgggtcggta tcggcatggg cgtgggcggc      540 aaccctggt cgcagctcca tgtcgtgcag cagccgggca ccgactcggc gctgatggtc      600
gagggcacgg tgcgggtcgt cgacgtggcc tccgcgccca cgggcgtcga ctcgcgcggc      660
ggcggcgtgc tgtacgcgga gaacggtgcg ctgaagtggc gcggctccga caacacggtc      720
accaccatcg ccccgcctg a                                                741

<210> SEQ ID NO 24
<211> LENGTH: 738
<212> TYPE: DNA
<213> ORGANISM: Streptomyces tsukubaensis

<400> SEQUENCE: 24
atggctgtga accggagact cttcctgggc ggattcaccg cggggcggt gaccgtggcg       60 gcgggcactg cgacgcccgc tgcggccgcg gcggcccagg ggccgacgac gacgttcgac      120
gggcccgtgg tcgccgagcg cttcagcacg aactcgacgg tcaactccgc cttcctgaag      180
acgacgtcca cgaccgagca cgccgcgacc gtctaccagg ccgggacctc gggcagcggg      240
gtcgccctga acatcgtgtc ggacaacccg gacaactcgg cggtctacct caccggccgg      300
gagaagaccc gcggcaccct gaagatctcg cacatcggcc atgcggacgg gtccgacgcg      360
gacgccgccg ccgtgtccat cgacctgaag acggccggaa ccgccacgca gggcatcttc      420
ctgaccgcca cggacggtgc cacgacgggc aatctgatct gtctgcgcaa caacggccgc      480
gacgatttcg tcgtcaaggg cagcggacgg gtcggcatcg gtctggcggt gggctccgcc      540 cctggtccc agctccatgt cgtccagcgg ccggggcccg actccgcgct gatggtcgag      600
ggagcggtac ggatcgtcga cgccgcgacc gtaccgacgg cggtcgactc caagggcggc      660
ggcacgctct acgcacaggg cggcgagctg atgtggcgca cgcgaacgg caacgtcacc      720 cgtatcgcct cggcctga                                                   738

<210> SEQ ID NO 25
<211> LENGTH: 375
<212> TYPE: DNA
<213> ORGANISM: Streptomyces pristinaespiralis
```

<400> SEQUENCE: 25

```
ttcgacggtc cggtggtggc ggagggtttc aggacggact ccaccgtcaa gtccgccttc      60
ttcaagacga cgtcgacgac cgagcacgcg gtgacggcct atcaggccgg cacgtccggc     120
agcggcgtgg ccctgaacgt cgtatcgaag aacccgggtg actcggccat gtatctcagt    180
ggcacggaga aggcgcacgg cacgctgaag atctcgcaca cgggccacgc ggacggctcg    240
gacgagaagg cgtccgctct gtcgatcgac ctgctgacgg cggggacggc agcccagggc    300
atcttcgtga aggcgggcaa cgggcccacc accggcaacc tgatctgcct gcgcaacaac    360
gcccgagacg acttc                                                      375
```

<210> SEQ ID NO 26
<211> LENGTH: 393
<212> TYPE: DNA
<213> ORGANISM: Streptomyces tsukubaensis

<400> SEQUENCE: 26

```
ttcgacgggc ccgtggtcgc cgagcgcttc agcacgaact cgacggtcaa ctccgccttc      60
ctgaagacga cgtccacgac cgagcacgcc gcgaccgtct accaggccgg gacctcgggc    120
agcggggtcg ccctgaacat cgtgtcggac aacccggaca actcggcggt ctacctcacc    180
ggccgggaga gacccgcgg caccctgaag atctcgcaca tcggccatgc ggacgggtcc    240
gacgcggacg ccgccgccgt gtccatcgac ctgaagacgg ccggaaccgc cacgcagggc    300
atcttcctga ccgccacgga cggtgccacg acgggcaatc tgatctgtct gcgcaacaac    360
ggccgcgacg atttcgtcgt caagggcagc gga                                  393
```

<210> SEQ ID NO 27
<211> LENGTH: 15
<212> TYPE: DNA
<213> ORGANISM: Streptomyces koganeiensis

<400> SEQUENCE: 27

```
ttcgacggcc cggtg                                                       15
```

<210> SEQ ID NO 28
<211> LENGTH: 34
<212> TYPE: DNA
<213> ORGANISM: Streptomyces koganeiensis

<400> SEQUENCE: 28

```
gtaggatccg ccggggagaa cggcgcgacg acga                                  34
```

<210> SEQ ID NO 29
<211> LENGTH: 34
<212> TYPE: DNA
<213> ORGANISM: Streptomyces koganeiensis

<400> SEQUENCE: 29

```
gactctagat cacgccggtg cgatcgtcgt gacc                                  34
```

<210> SEQ ID NO 30
<211> LENGTH: 20
<212> TYPE: DNA
<213> ORGANISM: Streptomyces koganeiensis

<400> SEQUENCE: 30

```
tgtggaattg tgagcggata                                                  20
```

```
<210> SEQ ID NO 31
<211> LENGTH: 21
<212> TYPE: DNA
<213> ORGANISM: Streptomyces koganeiensis

<400> SEQUENCE: 31
tttcaaccat tgttccagg t                                              21

<210> SEQ ID NO 32
<211> LENGTH: 33
<212> TYPE: DNA
<213> ORGANISM: Streptomyces koganeiensis

<400> SEQUENCE: 32
tggccatggc cggggagaac ggcgcgacga cga                                33

<210> SEQ ID NO 33
<211> LENGTH: 34
<212> TYPE: DNA
<213> ORGANISM: Streptomyces koganeiensis

<400> SEQUENCE: 33
ctcgaattct cacgccggtg cgatcgtcgt gacc                               34

<210> SEQ ID NO 34
<211> LENGTH: 20
<212> TYPE: DNA
<213> ORGANISM: Artificial Sequence
<220> FEATURE:
<223> OTHER INFORMATION: T7-promoter

<400> SEQUENCE: 34
taatacgact cactataggg                                               20

<210> SEQ ID NO 35
<211> LENGTH: 19
<212> TYPE: DNA
<213> ORGANISM: Artificial Sequence
<220> FEATURE:
<223> OTHER INFORMATION: T7-terminator

<400> SEQUENCE: 35
gctagttatt gctcagcgg                                                19

<210> SEQ ID NO 36
<211> LENGTH: 34
<212> TYPE: DNA
<213> ORGANISM: Streptomyces koganeiensis

<400> SEQUENCE: 36
atacatatgg ccggggagaa cggcgcgacg acga                               34

<210> SEQ ID NO 37
<211> LENGTH: 34
<212> TYPE: DNA
<213> ORGANISM: Streptomyces koganeiensis

<400> SEQUENCE: 37
ctcgaattct cacgccggtg cgatcgtcgt gacc                               34

<210> SEQ ID NO 38
<211> LENGTH: 8711
<212> TYPE: DNA
<213> ORGANISM: Artificial Sequence
```

<220> FEATURE:
<223> OTHER INFORMATION: Sequence of vector pHTsk_HYAL

<400> SEQUENCE: 38

| | | | | |
|---|---|---|---|---|
| ttaagttatt | ggtatgactg | gttttaagcg | caaaaaaagt | tgcttttcg tacctattaa | 60 |
| tgtatcgttt | tagaaaaccg | actgtaaaaa | gtacagtcgg | cattatctca tattataaaa | 120 |
| gccagtcatt | aggcctatct | gacaattcct | gaatagagtt | cataaacaat cctgcatgat | 180 |
| aaccatcaca | aacagaatga | tgtacctgta | aagatagcgg | taaatatatt gaattacctt | 240 |
| tattaatgaa | ttttcctgct | gtaataatgg | gtagaaggta | attactatta ttattgatat | 300 |
| ttaagttaaa | cccagtaaat | gaagtccatg | gaataataga | aagagaaaaa gcattttcag | 360 |
| gtataggtgt | tttgggaaac | aatttccccg | aaccattata | tttctctaca tcagaaaggt | 420 |
| ataaatcata | aaactctttg | aagtcattct | ttacaggagt | ccaaatacca gagaatgttt | 480 |
| tagatacacc | atcaaaaatt | gtataaagtg | gctctaactt | atcccaataa cctaactctc | 540 |
| cgtcgctatt | gtaaccagtt | ctaaaagctg | tatttgagtt | tatcacccct gtcactaaga | 600 |
| aaataaatgc | agggtaaaat | ttatatcctt | cttgttttat | gtttcggtat aaaacactaa | 660 |
| tatcaatttc | tgtggttata | ctaaaagtcg | tttgttggtt | caaataatga ttaaaatatct | 720 |
| cttttctctt | ccaattgtct | aaatcaattt | tattaaagtt | catttgatat gcctcctaaa | 780 |
| tttttatcta | aagtgaattt | aggaggctta | cttgtctgct | ttcttcatta gaatcaatcc | 840 |
| ttttttaaaa | gtcaatatta | ctgtaacata | aatatatatt | ttaaaaatat cccactttat | 900 |
| ccaattttcg | tttgttgaac | taatgggtgc | tttagttgaa | gaataaagac cacattaaaa | 960 |
| aatgtggtct | tttgtgtttt | tttaaaggat | ttgagcgtag | cgaaaaatcc ttttctttct | 1020 |
| tatcttgata | taagggtaa | ctattgccga | tcgtccattc | cgacagcatc gccagtcact | 1080 |
| atggcgtgct | gctagcgcca | ttcgccattc | aggctgcgca | actgttggga agggcgatcg | 1140 |
| gtgcgggcct | cttcgctatt | acgccagctg | gcgaaagggg | gatgtgctgc aaggcgatta | 1200 |
| agttgggtaa | cgccagggtt | ttcccagtca | cgacgttgta | aaacgacggc cagtgaattc | 1260 |
| gagctcaggc | cttaactcac | attaattgcg | ttgcgctcac | tgcccgcttt ccagtcggga | 1320 |
| aacctgtcgt | gccagctgca | ttaatgaatc | ggccaacgcg | cggggagagg cggtttgcgt | 1380 |
| attgggcgcc | agggtggttt | ttcttttcac | cagtgagacg | ggcaacagct gattgccctt | 1440 |
| caccgcctgg | ccctgagaga | gttgcagcaa | gcggtccacg | ctggtttgcc ccagcaggcg | 1500 |
| aaaatcctgt | ttgatggtgg | ttgacggcgg | gatataacat | gagctgtctt cggtatcgtc | 1560 |
| gtatcccact | accgagatat | ccgcaccaac | gcgcagcccg | gactcggtaa tggcgcgcat | 1620 |
| tgcgcccagc | gccatctgat | cgttggcaac | cagcatcgca | gtgggaacga tgccctcatt | 1680 |
| cagcatttgc | atggtttgtt | gaaaaccgga | catggcactc | cagtcgcctt cccgttccgc | 1740 |
| tatcggctga | atttgattgc | gagtgagata | tttatgccag | ccagccagac gcagacgcgc | 1800 |
| cgagacagaa | cttaatgggc | ccgctaacag | cgcgatttgc | tggtgaccca atgcgaccag | 1860 |
| atgctccacg | cccagtcgcg | taccgtcttc | atgggagaaa | ataatactgt tgatgggtgt | 1920 |
| ctggtcagag | acatcaagaa | ataacgccgg | aacattagtg | caggcagctt ccacagcaat | 1980 |
| ggcatcctgg | tcatccagcg | gatagttaat | gatcagccca | ctgacgcgtt gcgcgagaag | 2040 |
| attgtgcacc | gccgctttac | aggcttcgac | gccgcttcgt | tctaccatcg acaccaccac | 2100 |
| gctggcaccg | agttgatcgg | cgcgagattt | aatcgccgcg | acaatttgcg acggcgcgtg | 2160 |
| cagggccaga | ctggaggtgg | caacgccaat | cagcaacgac | tgtttgcccg ccagttgttg | 2220 |

```
tgccacgcgg ttgggaatgt aattcagctc cgccatcgcc gcttccactt tttcccgcgt    2280
tttcgcagaa acgtggctgg cctggttcac cacgcgggaa acggtctgat aagagacacc    2340
ggcatactct gcgacatcgt ataacgttac tggtttcatc aaaatcgtct ccctccgttt    2400
gaatatttga ttgatcgtaa ccagatgaag cactcttttcc actatcccta cagtgttatg    2460
gcttgaacaa tcacgaaaca ataattggta cgtacgatct ttcagccgac tcaaacatca    2520
aatcttacaa atgtagtctt tgaaagtatt acatatgtaa gatttaaatg caaccgtttt    2580
ttcggaagga aatgatgacc tcgtttccac cggaattagc ttggtaccag ctattgtaac    2640
ataatcggta cggggtgaa aaagctaacg gaaaagggag cggaaaagaa tgatgtaagc      2700
gtgaaaaatt ttttatctta tcacttgaaa ttggaaggga gattctttat tataagaatt    2760
gtggaattgt gagcggataa caattcccaa ttaaaggagg aaggatcaat gattcaaaaa    2820
cgaaagcgga cagtttcgtt cagacttgtg cttatgtgca cgctgttatt tgtcagtttg    2880
ccgattacaa aaacatcagc cgtaggatcc gccggggaga acggcgcgac gacgaccttc    2940
gacggcccgg tggccgccga gaggttcagc gcggacacca cactgaggc cgccttcctc      3000
aagacgacct cggagacgaa ccacgcggcg accatctacc aggccggtac gtcgggcgac    3060
ggcgcggcgc tgaacgtgat ctccgacaac ccgggcacct cggccatgta cctctccggc    3120
accgagaccg cgcgcggcac cctgaagatc acccaccgcg ggtacgccga cggctccgac    3180
aaggacgccc cgcccctgtc gctcgacctc cgcgtggccg caccgccgc ccagggcatc      3240
tacgtcacgg cgacgaacgg cccgaccaag ggcaacctga tcgccctgcg caacaacacg    3300
ggcctggacg acttcgtcgt caagggcacc ggccgcatcg gcgtcggcat cgaccgcgcg    3360
gccacgcccc gcgcccaggt ccacatcgtc cagcggggcg acgccctcgc cgcgctcctg    3420
gtggagggct cggtacgcat cgggaacgcc gcgacggtac cgacgtcggt ggacagctcg    3480
ggcggcggcg ccctgtacgc gtcgggcggc gccctgctgt ggcgcggctc caacggcacg    3540
gtcacgacga tcgcaccggc gtgatctaga gtcgacgtcc ccggggcagc ccgcctaatg    3600
agcgggcttt tttcacgtca cgcgtccatg gagatctttg tctgcaactg aaaagtttat    3660
accttacctg gaacaaatgg ttgaaacata cgaggctaat atcggctat taggaatagt      3720
ccctgtacta ataaaatcag gtggatcagt tgatcagtat attttggacg aagctcggaa    3780
agaatttgga gatgacttgc ttaattccac aattaaatta agggaaagaa taaagcgatt    3840
tgatgttcaa ggaatcacgg aagaagatac tcatgataaa gaagctctaa aactattcaa    3900
taaccttaca atggaattga tcgaaagggt ggaaggttaa tggtacgaaa attaggggat    3960
ctacctagaa agccacaagg cgataggtca agcttaaaga acccttacat ggatcttaca    4020
gattctgaaa gtaaagaaac aacagaggtt aaacaaacag aaccaaaaag aaaaaaagca    4080
tgttgaaaaa caatgaaagt tgatgtttca atccataata agattaaatc gctgcacgaa    4140
attctggcag catccgaagg gaattcatat tacttagagg atactattga gagagctatt    4200
gataagatgg ttgagacatt acctgagagc caaaaaactt tttatgaata tgaattaaaa    4260
aaaagaacca acaaaggctg agacagactc caaacgagtc tgtttttta aaaaaaatat      4320
taggagcatt gaatatatat tagagaatta agaaagacat gggaataaaa atattttaaa    4380
tccagtaaaa atatgataag attatttcag aatatgaaga actctgtttg ttttttgatga    4440
aaaaacaaac aaaaaaaatc cacctaacgg aatctcaatt taactaacag cggccaaact    4500
gagaagttaa atttgagaag gggaaaaggc ggatttatac ttgtatttaa ctatctccat    4560
tttaacattt tattaaaccc catacaagtg aaaatcctct tttacactgt tcctttaggt    4620
```

```
gatcgcggag ggacattatg agtgaagtaa acctaaaagg aaatacagat gaattagtgt    4680
attatcgaca gcaaaccact ggaaataaaa tcgccaggaa gagaatcaaa aaagggaaag    4740
aagaagttta ttatgttgct gaaacggaag agaagatatg gacagaagag caaataaaaa    4800
acttttcttt agacaaattt ggtacgcata taccttacat agaaggtcat tatacaatct    4860
taaataatta cttctttgat ttttggggct attttttagg tgctgaagga attgcgctct    4920
atgctcacct aactcgttat gcatacggca gcaaagactt ttgctttcct agtctacaaa    4980
caatcgctaa aaaatggac aagactcctg ttacagttag aggctacttg aaactgcttg    5040
aaaggtacgg ttttatttgg aaggtaaacg tccgtaataa aaccaaggat aacacagagg    5100
aatccccgat ttttaagatt agacgtaagg ttcctttgct ttcagaagaa cttttaaatg    5160 gaaccctaa tattgaaatt ccagatgacg aggaagcaca tgtaaagaag gcttaaaaaa    5220 aggaaaaga gggtcttcca aaggttttga aaaagagca cgatgaattt gttaaaaaaa    5280
tgatggatga gtcagaaaca attaatattc cagaggcctt acaatatgac acaatgtatg    5340
aagatatact cagtaaagga gaaattcgaa agaaatcaa aaaacaaata cctaatccta    5400
caacatcttt tgagagtata tcaatgacaa ctgaagagga aaaagtcgac agtactttaa    5460
aaagcgaaat gcaaatcgt gtctctaagc cttcttttga tacctggttt aaaaacacta    5520
agatcaaaat tgaaataaa aattgtttat tacttgtacc gagtgaattt gcatttgaat    5580
ggattaagaa aagatattta gaaacaatta aaacagtcct tgaagaagct ggatatgttt    5640
tcgaaaaaat cgaactaaga aaagtgcaat aaactgctga agtatttcag cagttttttt    5700
tatttagaaa tagtgaaaaa aatataatca gggaggtatc aatatttaat gagtactgat    5760
ttaaatttat ttagactgga attaataatt aacacgtaga ctaattaaaa tttaatgagg    5820
gataaagagg atacaaaaat attaatttca atccctatta aattttaaca aggggggggat    5880 taaaatttaa ttagaggttt atccacaaga aaagacccta ataaaatttt tactagggtt    5940
ataacactga ttaatttctt aatgggggag ggattaaaat ttaatgacaa agaaaacaat    6000
cttttaagaa aagcttttaa aagataataa taaaaagagc tttgcgatta agcaaaactc    6060
tttacttttt cattgacatt atcaaattca tcgatttcaa attgttgttg tatcataaag    6120
ttaattctgt tttgcacaac cttttcagga atataaaaca catctgaggc ttgttttata    6180
aactcagggt cgctaaagtc aatgtaacgt agcatatgat atggtatagc ttccacccaa    6240
gttagccttt ctgcttcttc tgaatgtttt tcatatactt ccatgggtat ctctaaatga    6300
ttttcctcat gtagcaaggt atgagcaaaa agtttatgga attgatagtt cctctctttt    6360
tcttcaactt ttttatctaa acaaacact ttaacatctg agtcaatgta agcataagat    6420
gttttcccag tcataatttc aatcccaaat cttttagaca gaaattctgg acgtaaatct    6480
tttggtgaaa gattttttt atgtagcaat atatccgata cagcaccttc taaaagcgtt    6540
ggtgaatagg gcattttacc tatctcctct cattttgtgg aataaaaata gtcatattcg    6600
tccatctacc tatcctatta tcgaacagtt gaacttttta atcaaggatc agtccttttt    6660
ttcattattc ttaaactgtg ctcttaactt taacaactcg atttgttttt ccagatctcg    6720
agggtaacta gcctcgccga tcccgcaaga ggcccggcag tcaggtggca cttttcgggg    6780
aaatgtgcgc ggaacccta tttgtttatt tttctaaata cattcaaata tgtatccgct    6840
catgagacaa taaccctgat aaatgcttca ataatattga aaaggaaga gtatgagtat    6900 tcaacatttc cgtgtcgccc ttattccctt ttttgcggca ttttgccttc ctgttttttgc    6960 tcacccagaa acgctggtga agtaaaaaga tgctgaagat cagttgggtg cacgagtggg    7020
```

-continued

| | |
|---|---|
| ttacatcgaa ctggatctca acagcggtaa gatccttgag agttttcgcc ccgaagaacg | 7080 |
| ttttccaatg atgagcactt ttaaagttct gctatgtggc gcggtattat cccgtattga | 7140 |
| cgccgggcaa gagcaactcg gtcgccgcat acactattct cagaatgact tggttgagta | 7200 |
| ctcaccagtc acagaaaagc atcttacgga tggcatgaca gtaagagaat tatgcagtgc | 7260 |
| tgccataacc atgagtgata acactgcggc caacttactt ctgacaacga tcggaggacc | 7320 |
| gaaggagcta accgcttttt tgcacaacat gggggatcat gtaactcgcc ttgatcgttg | 7380 |
| ggaaccggag ctgaatgaag ccataccaaa cgacgagcgt gacaccacga tgcctgtagc | 7440 |
| aatggcaaca acgttgcgca aactattaac tggcgaacta cttactctag cttcccggca | 7500 |
| acaattaata gactggatgg aggcggataa agttgcagga ccacttctgc gctcggccct | 7560 |
| tccggctggc tggtttattg ctgataaatc tggagccggt gagcgtgggt ctcgcggtat | 7620 |
| cattgcagca ctggggccag atggtaagcc ctcccgtatc gtagttatct acacgacggg | 7680 |
| gagtcaggca actatggatg aacgaaatag acagatcgct gagataggtg cctcactgat | 7740 |
| taagcattgg taactgtcag accaagttta ctcatatata ctttagattg atttaaaact | 7800 |
| tcatttttaa tttaaaagga tctaggtgaa gatcctttt gataatctca tgaccaaaat | 7860 |
| cccttaacgt gagttttcgt tccactgagc gtcagacccc gtagaaaaga tcaaaggatc | 7920 |
| ttcttgagat ccttttttc tgcgcgtaat ctgctgcttg caaacaaaaa aaccaccgct | 7980 |
| accagcggtg gtttgtttgc cggatcaaga gctaccaact cttttccga aggtaactgg | 8040 |
| cttcagcaga gcgcagatac caaatactgt ccttctagtg tagccgtagt taggccacca | 8100 |
| cttcaagaac tctgtagcac cgcctacata cctcgctctg ctaatcctgt taccagtggc | 8160 |
| tgctgccagt ggcgataagt cgtgtcttac cgggttggac tcaagacgat agttaccgga | 8220 |
| taaggcgcag cggtcgggct gaacggggg ttcgtgcaca gcccagct tggagcgaac | 8280 |
| gacctacacc gaactgagat acctacagcg tgagctatga aaagcgcca cgcttcccga | 8340 |
| agggagaaag gcggacaggt atccggtaag cggcagggtc ggaacaggag agcgcacgag | 8400 |
| ggagcttcca gggggaaacg cctggtatct ttatagtcct gtcgggtttc gccacctctg | 8460 |
| acttgagcgt cgatttttgt gatgctcgtc aggggggcgg agcctatgga aaaacgccag | 8520 |
| caacgcggcc ttttacggt tcctggcctt ttgctggcct tttgctcaca tgttctttcc | 8580 |
| tgcgttatcc cctgattctg tggataaccg tattaccgcc tttgagtgag ctgataccgc | 8640 |
| tcgccgcagc cgaacgaccg agcgcagcga gtcagtgagc gaggaagcgg aagagcgccc | 8700 |
| aatacgcatg c | 8711 |

<210> SEQ ID NO 39
<211> LENGTH: 6124
<212> TYPE: DNA
<213> ORGANISM: Artificial Sequence
<220> FEATURE:
<223> OTHER INFORMATION: Sequence of vector pHyal_sk

<400> SEQUENCE: 39

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcgggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |

-continued

```
ttttgattta aagggatttt tgccgatttc ggcctattgg ttaaaaaatg agctgattta      420
acaaaaattt aacgcgaatt ttaacaaaat attaacgttt acaatttcag gtggcacttt      480
tcggggaaat gtgcgcggaa cccctatttg tttattttc taaatacatt caaatatgta      540
tccgctcatg agacaataac cctgataaat gcttcaataa tattgaaaaa ggaagagtat      600
gagtattcaa catttccgtg tcgcccttat tccctttttt gcggcatttt gccttcctgt      660
ttttgctcac ccagaaacgc tggtgaaagt aaaagatgct gaagatcagt tgggtgcacg      720
agtgggttac atcgaactgg atctcaacag cggtaagatc cttgagagtt ttcgccccga      780
agaacgtttt ccaatgatga gcacttttaa agttctgcta tgtggcgcgg tattatcccg      840
tattgacgcc gggcaagagc aactcggtcg ccgcatacac tattctcaga atgacttggt      900
tgagtactca ccagtcacag aaaagcatct tacggatggc atgacagtaa gagaattatg      960
cagtgctgcc ataaccatga gtgataacac tgcggccaac ttacttctga caacgatcgg     1020
aggaccgaag gagctaaccg cttttttgca caacatgggg gatcatgtaa ctcgccttga     1080
tcgttgggaa ccggagctga atgaagccat accaaacgac gagcgtgaca ccacgatgcc     1140
tgcagcaatg gcaacaacgt tgcgcaaact attaactggc gaactactta ctctagcttc     1200
ccggcaacaa ttaatagact ggatggaggc ggataaagtt gcaggaccac ttctgcgctc     1260
ggcccttccg gctggctggt ttattgctga taaatctgga gccggtgagc gtgggtctcg     1320
cggtatcatt gcagcactgg ggccagatgg taagccctcc cgtatcgtag ttatctacac     1380
gacggggagt caggcaacta tggatgaacg aaatagacag atcgctgaga taggtgcctc     1440
actgattaag cattggtaac tgtcagacca agtttactca tatatacttt agattgattt     1500
aaaacttcat ttttaattta aaaggatcta ggtgaagatc ctttttgata atctcatgac     1560
caaaatccct taacgtgagt tttcgttcca ctgagcgtca gaccccgtag aaaagatcaa     1620
aggatcttct tgagatcctt ttttttctgcg cgtaatctgc tgcttgcaaa caaaaaaacc     1680
accgctacca gcggtggttt gtttgccgga tcaagagcta ccaactcttt ttccgaaggt     1740
aactggcttc agcagagcgc agataccaaa tactgtcctt ctagtgtagc cgtagttagg     1800
ccaccacttc aagaactctg tagcaccgcc tacatacctc gctctgctaa tcctgttacc     1860
agtggctgct gccagtggcg ataagtcgtg tcttaccggg ttggactcaa gacgatagtt     1920
accggataag cgcagcggt cgggctgaac ggggggttcg tgcacacagc ccagcttgga     1980
gcgaacgacc tacaccgaac tgagatacct acagcgtgag ctatgagaaa gcgccacgct     2040
tcccgaaggg agaaaggcgg acaggtatcc ggtaagcggc agggtcggaa caggagagcg     2100
cacgagggag cttccagggg gaaacgcctg gtatctttat agtcctgtcg ggtttcgcca     2160
cctctgactt gagcgtcgat ttttgtgatg ctcgtcaggg gggcggagcc tatggaaaaa     2220
cgccagcaac gcggcctttt tacggttcct ggccttttgc tggccttttg ctcacatgtt     2280
ctttcctgcg ttatccctg attctgtgga taaccgtatt accgcctttg agtgagctga     2340
taccgctcgc cgcagccgaa cgaccgagcg cagcgagtca gtgagcgagg aagcggaaga     2400
gcgcctgatg cggtattttc tccttacgca tctgtgcggt atttcacacc gcatatatgg     2460
tgcactctca gtacaatctg ctctgatgcc gcatagttaa gccagtatac actccgctat     2520
cgctacgtga ctgggtcatg gctgcgcccc gacacccgcc aacacccgct gacgcgccct     2580
gacgggcttg tctgctcccg gcatccgctt acagacaagc tgtgaccgtc tccgggagct     2640
gcatgtgtca gaggttttca ccgtcatcac cgaaacgcgc gaggcagctg cggtaaagct     2700
catcagcgtg gtcgtgaagc gattcacaga tgtctgcctg ttcatccgcg tccagctcgt     2760
```

```
tgagtttctc cagaagcgtt aatgtctggc ttctgataaa gcgggccatg ttaagggcgg    2820 tttttttcctg tttggtcact gatgcctccg tgtaagggg atttctgttc atggggtaa     2880 tgataccgat gaaacgagag aggatgctca cgatacgggt tactgatgat gaacatgccc   2940
ggttactgga acgttgtgag ggtaaacaac tggcggtatg gatgcggcgg gaccagagaa   3000
aaatcactca gggtcaatgc cagcgcttcg ttaatacaga tgtaggtgtt ccacagggta   3060
gccagcagca tcctgcgatg cagatccgga acataatggt gcagggcgct gacttccgcg   3120
tttccagact ttacgaaaca cggaaaccga agaccattca tgttgttgct caggtcgcag   3180
acgttttgca gcagcagtcg cttcacgttc gctcgcgtat cggtgattca ttctgctaac   3240
cagtaaggca accccgccag cctagccggg tcctcaacga caggagcacg atcatgcgca   3300 cccgtgggc cgccatgccg gcgataatgg cctgcttctc gccgaaacgt ttggtggcgg    3360
gaccagtgac gaaggcttga gcgagggcgt gcaagattcc gaataccgca agcgacaggc   3420
cgatcatcgt cgcgctccag cgaaagcggt cctcgccgaa aatgacccag agcgctgccg   3480
gcacctgtcc tacgagttgc atgataaaga agacagtcat aagtgcggcg acgatagtca   3540
tgccccgcgc ccaccggaag gagctgactg ggttgaaggc tctcaagggc atcggtcgag   3600
atcccggtgc ctaatgagtg agctaactta cattaattgc gttgcgctca ctgcccgctt   3660
tccagtcggg aaacctgtcg tgccagctgc attaatgaat cggccaacgc gcggggagag   3720
gcggtttgcg tattgggcgc cagggtggtt tttcttttca ccagtgagac gggcaacagc   3780
tgattgccct tcaccgcctg gccctgagag agttgcagca agcggtccac gctggtttgc   3840
cccagcaggc gaaaatcctg tttgatggtg gttaacggcg ggatataaca tgagctgtct   3900
tcggtatcgt cgtatcccac taccgagata tccgcaccaa cgcgcagccc ggactcggta   3960
atggcgcgca ttgcgcccag cgccatctga tcgttggcaa ccagcatcgc agtgggaacg   4020
atgccctcat tcagcatttg catggtttgt tgaaaaccgg acatggcact ccagtcgcct   4080
tcccgttccg ctatcggctg aatttgattg cgagtgagat atttatgcca gccagccaga   4140
cgcagacgcg ccgagacaga acttaatggg cccgctaaca gcgcgatttg ctggtgaccc   4200
aatgcgacca gatgctccac gcccagtcgc gtaccgtctt catgggagaa aataatactg   4260
ttgatgggtg tctggtcaga gacatcaaga ataacgccg gaacattagt gcaggcagct    4320
tccacagcaa tggcatcctg gtcatccagc ggatagttaa tgatcagccc actgacgcgt   4380
tgcgcgagaa gattgtgcac cgccgcttta caggcttcga cgccgcttcg ttctaccatc   4440
gacaccacca cgctggcacc cagttgatcg gcgcgagatt taatcgccgc gacaatttgc   4500
gacggcgcgt gcagggccag actggaggtg gcaacgccaa tcagcaacga ctgtttgccc   4560
gccagttgtt gtgccacgcg gttgggaatg taattcagct ccgccatcgc cgcttccact   4620 tttcccgcg tttttcgcaga acgtggctg gcctggttca ccacgcggga aacggtctga    4680
taagagacac cggcatactc tgcgacatcg tataacgtta ctggtttcac attcaccacc   4740
ctgaattgac tctcttccgg gcgctatcat gccataccgc gaaaggtttt gcgccattcg   4800
atggtgtccg ggatctcgac gctctcccct atgcgactcc tgcattagga agcagcccag   4860
tagtaggttg aggccgttga gcaccgccgc cgcaaggaat ggtgcatgca aggagatggc   4920
gcccaacagt cccccggcca cggggcctgc caccatacccc acgccgaaac aagcgctcat   4980
gagcccgaag tggcgagccc gatcttcccc atcggtgatg tcggcgatat aggcgccagc   5040
aaccgcacct gtggcgccgg tgatgccggc cacgatgcgt ccggcgtaga ggatcgagat   5100
ctcgatcccg cgaaattaat acgactcact ataggggaat tgtgagcgga taacaattcc   5160
```

```
cctctagaaa taattttgtt taactttaag aaggagatat acatatgaaa tacctgctgc    5220
cgaccgctgc tgctggtctg ctgctcctcg ctgcccagcc ggcgatggcc atggccgggg    5280
agaacggcgc gacgacgacc ttcgacggcc cggtggccgc cgagaggttc agcgcggaca    5340
ccacactgga ggccgccttc ctcaagacga cctcggagac gaaccacgcg gcgaccatct    5400
accaggccgg tacgtcgggc gacggcgcgg cgctgaacgt gatctccgac aacccgggca    5460
cctcggccat gtacctctcc ggcaccgaga ccgcgcgcgg caccctgaag atcacccacc    5520
gcgggtacgc cgacggctcc gacaaggacg ccgccgccct gtcgctcgac ctccgcgtgg    5580
ccggcaccgc cgcccagggc atctacgtca cggcgacgaa cggcccgacc aagggcaacc    5640
tgatcgccct gcgcaacaac acgggcctgg acgacttcgt cgtcaagggc accggccgca    5700
tcggcgtcgg catcgaccgc gcggccacgc cccgcgccca gtccacatc gtccagcggg    5760
gcgacgccct cgccgcgctc ctggtggagg gctcggtacg catcgggaac gccgcgacgg    5820
taccgacgtc ggtggacagc tcgggcggcg gcgccctgta cgcgtcgggc ggcgccctgc    5880
tgtggcgcgg ctccaacggc acggtcacga cgatcgcacc ggcgtgagaa ttcgagctcc    5940
gtcgacaagc ttgcggccgc actcgagcac caccaccacc accactgaga tccggctgct    6000
aacaaagccc gaaaggaagc tgagttggct gctgccaccg ctgagcaata actagcataa    6060
ccccttgggg cctctaaacg ggtcttgagg ggttttttgc tgaaaggagg aactatatcc    6120
ggat                                                                6124

<210> SEQ ID NO 40
<211> LENGTH: 6058
<212> TYPE: DNA
<213> ORGANISM: Artificial Sequence
<220> FEATURE:
<223> OTHER INFORMATION: Sequence of vector pHyal_sk_SL

<400> SEQUENCE: 40
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tcccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttt tgccgatttc ggcctattgg ttaaaaaatg agctgattta     420
acaaaaattt aacgcgaatt ttaacaaat attaacgttt acaatttcag gtggcacttt     480
tcggggaaat gtgcgcggaa cccctatttg tttattttc taaatacatt caaatatgta     540
tccgctcatg agacaataac cctgataaat gcttcaataa tattgaaaaa ggaagagtat     600
gagtattcaa catttccgtg tcgcccttat tcccttttt gcggcatttt gccttcctgt     660
ttttgctcac ccagaaacgc tggtgaaagt aaaagatgct gaagatcagt tgggtgcacg    720
agtgggttac atcgaactgg atctcaacag cggtaagatc cttgagagtt ttcgccccga    780
agaacgtttt ccaatgatga gcactttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataacac tgcggccaac ttacttctga caacgatcgg   1020
aggaccgaag gagctaaccg cttttttgca caacatgggg gatcatgtaa ctcgccttga   1080
```

```
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct taacgtgagt tttcgttcca ctgagcgtca gaccccgtag aaaagatcaa    1620
aggatcttct tgagatcctt tttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag cgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggccttttt tacggttcct ggccttttgc tggccttttg ctcacatgtt    2280
ctttcctgcg ttatccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaaggggg atttctgttc atgggggtaa    2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg gcgataatgg cctgcttctc gccgaaacgt ttggtggcgg    3360
gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
```

```
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagata tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat atttatgcca gccagccaga    4140
cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga aataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg gatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccataccc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
ctcgatcccg cgaaattaat acgactcact ataggggaat tgtgagcgga taacaattcc    5160
cctctagaaa taattttgtt taactttaag aaggagatat acatatggcc ggggagaacg    5220
gcgcgacgac gaccttcgac ggcccggtgg ccgccgagag gttcagcgcg acaccacac    5280
tggaggccgc cttcctcaag acgacctcgg agacgaacca cgcggcgacc atctaccagg    5340
ccggtacgtc gggcgacggc gcggcgctga acgtgatctc cgacaacccg ggcacctcgg    5400
ccatgtacct ctccggcacc gagaccgcgc gcggcaccct gaagatcacc caccgcgggt    5460
acgccgacgg ctccgacaag gacgccgccg ccctgtcgct cgacctccgc gtggccggca    5520
ccgccgccca gggcatctac gtcacggcga cgaacggccc gaccaagggc aacctgatcg    5580
ccctgcgcaa caacacgggc ctggacgact tcgtcgtcaa gggcaccggc cgcatcggcg    5640
tcggcatcga ccgcgcggcc acgccccgcg cccaggtcca catcgtccag cggggcgacg    5700
ccctcgccgc gctcctggtg gagggctcgg tacgcatcgg gaacgccgcg acggtaccga    5760
cgtcggtgga cagctcgggc ggcggcgccc tgtacgcgtc gggcggcgcc ctgctgtggc    5820
gcggctccaa cggcacggtc acgacgatcg caccggcgtg agaattcgag ctccgtcgac    5880
```

```
aagcttgcgg ccgcactcga gcaccaccac caccaccact gagatccggc tgctaacaaa    5940
gcccgaaagg aagctgagtt ggctgctgcc accgctgagc aataactagc ataacccctt    6000
ggggcctcta acgggtctt gaggggtttt tgctgaaag gaggaactat atccggat        6058
```

<210> SEQ ID NO 41
<211> LENGTH: 654
<212> TYPE: DNA
<213> ORGANISM: Streptomyces koganeiensis

<400> SEQUENCE: 41

```
atggccgggg agaacggcgc gacgacgacc ttcgacggcc cggtggccgc cgagaggttc      60
agcgcggaca ccacactgga ggccgccttc ctcaagacga cctcggagac gaaccacgcg     120
gcgaccatct accaggccgg tacgtcgggc gacggcgcgg cgctgaacgt gatctccgac     180
aacccgggca cctcggccat gtacctctcc ggcaccgaga ccgcgcgcgg caccctgaag     240
atcacccacc gcgggtacgc cgacggctcc gacaaggacg ccgccgccct gtcgctcgac     300
ctccgcgtgg ccggcaccgc cgcccagggc atctacgtca cggcgacgaa cggcccgacc     360
aagggcaacc tgatcgccct gcgcaacaac acgggcctgg acgacttcgt cgtcaagggc     420
accgccgcca tcggcgtcgg catcgaccgc gcggccacgc ccgcgcccca ggtccacatc     480
gtccagcggg gcgacgccct cgccgcgctc ctggtggagg gctcggtacg catcgggaac     540
gccgcgacgg taccgacgtc ggtggacagc tcgggcggcg cgccctgta cgcgtcgggc      600 ggcgccctgc tgtggcgcgg ctccaacggc acggtcacga cgatcgcacc ggcg            654
```

<210> SEQ ID NO 42
<211> LENGTH: 6
<212> TYPE: PRT
<213> ORGANISM: Artificial Sequence
<220> FEATURE:
<223> OTHER INFORMATION: N-terminal amminoacidic sequence following to
      conpHyal_sk_SL transformation

<400> SEQUENCE: 42

Ala Gly Glu Asn Gly Ala
1               5

<210> SEQ ID NO 43
<211> LENGTH: 7
<212> TYPE: PRT
<213> ORGANISM: Artificial Sequence
<220> FEATURE:
<223> OTHER INFORMATION: The more represented N-terminal sequence from
      E.coli sample transformed with vector pHyal_sk

<400> SEQUENCE: 43

Met Ala Gly Glu Asn Gly Ala
1               5

<210> SEQ ID NO 44
<211> LENGTH: 13
<212> TYPE: PRT
<213> ORGANISM: Artificial Sequence
<220> FEATURE:
<223> OTHER INFORMATION: The least represented N-terminal sequence in
      E.coli sample transformed with vector pHyal_sk

<400> SEQUENCE: 44

Ala Gln Pro Ala Met Ala Met Ala Gly Glu Asn Gly Ala
1               5                   10

-continued

```
<210> SEQ ID NO 45
<211> LENGTH: 7
<212> TYPE: PRT
<213> ORGANISM: Artificial Sequence
<220> FEATURE:
<223> OTHER INFORMATION: N-terminal of partially mature protein  from
      E.coli transformed with vector pHyal_sk

<400> SEQUENCE: 45

Ala Gln Pro Ala Met Ala Met
1               5

<210> SEQ ID NO 46
<211> LENGTH: 129
<212> TYPE: PRT
<213> ORGANISM: Streptomyces koganeiensis

<400> SEQUENCE: 46

Phe Asp Gly Pro Val Ala Ala Glu Arg Phe Ser Ala Asp Thr Thr Leu
1               5                   10                  15

Glu Ala Ala Phe Leu Lys Thr Thr Ser Glu Thr Asn His Ala Ala Thr
            20                  25                  30

Ile Tyr Gln Ala Gly Thr Ser Gly Asp Gly Ala Ala Leu Asn Val Ile
        35                  40                  45

Ser Asp Asn Pro Gly Thr Ser Ala Met Tyr Leu Ser Gly Thr Glu Thr
    50                  55                  60

Ala Arg Gly Thr Leu Lys Ile Thr His Arg Gly Tyr Ala Asp Gly Ser
65                  70                  75                  80

Asp Lys Asp Ala Ala Ala Leu Ser Leu Asp Leu Arg Val Ala Gly Thr
                85                  90                  95

Ala Ala Gln Gly Ile Tyr Val Thr Ala Thr Asn Gly Pro Thr Lys Gly
            100                 105                 110

Asn Leu Ile Ala Leu Arg Asn Asn Thr Gly Leu Asp Asp Phe Val Val
        115                 120                 125

Lys

<210> SEQ ID NO 47
<211> LENGTH: 30
<212> TYPE: PRT
<213> ORGANISM: Streptomyces koganeiensis

<400> SEQUENCE: 47

Met Pro Val Ala Arg Arg Leu Phe Leu Gly Ser Phe Thr Ala Gly Ala
1               5                   10                  15

Val Thr Val Ala Thr Ala Ala Ala Thr Gly Thr Ala Ser Ala
            20                  25                  30

<210> SEQ ID NO 48
<211> LENGTH: 246
<212> TYPE: PRT
<213> ORGANISM: Streptomyces pristinaespiralis

<400> SEQUENCE: 48

Met Ser Val Ser Arg Arg Leu Phe Leu Gly Gly Phe Thr Ala Gly Ala
1               5                   10                  15

Val Thr Val Ala Ala Gly Ala Ala Ala Thr Pro Ala Ala Ala Ala Glu
            20                  25                  30

Ala Asp Gly Pro Thr Thr Thr Phe Asp Gly Pro Val Val Ala Glu Gly
        35                  40                  45
```

```
Phe Arg Thr Asp Ser Thr Val Lys Ser Ala Phe Phe Lys Thr Thr Ser
     50                  55                  60

Thr Thr Glu His Ala Val Thr Ala Tyr Gln Ala Gly Thr Ser Gly Ser
 65                  70                  75                  80

Gly Val Ala Leu Asn Val Val Ser Lys Asn Pro Gly Asp Ser Ala Met
                 85                  90                  95

Tyr Leu Ser Gly Thr Glu Lys Ala His Gly Thr Leu Lys Ile Ser His
            100                 105                 110

Thr Gly His Ala Asp Gly Ser Asp Glu Lys Ala Ser Ala Leu Ser Ile
        115                 120                 125

Asp Leu Leu Thr Ala Gly Thr Ala Ala Gln Gly Ile Phe Val Lys Ala
130                 135                 140

Gly Asn Gly Pro Thr Thr Gly Asn Leu Ile Cys Leu Arg Asn Asn Ala
145                 150                 155                 160

Arg Asp Asp Phe Val Val Lys Gly Ser Gly Arg Val Gly Ile Gly Met
                165                 170                 175

Gly Val Gly Gly Asn Pro Trp Ser Gln Leu His Val Val Gln Gln Pro
            180                 185                 190

Gly Thr Asp Ser Ala Leu Met Val Glu Gly Thr Val Arg Val Val Asp
        195                 200                 205

Val Ala Ser Ala Pro Thr Gly Val Asp Ser Arg Gly Gly Val Leu
210                 215                 220

Tyr Ala Glu Asn Gly Ala Leu Lys Trp Arg Gly Ser Asp Asn Thr Val
225                 230                 235                 240

Thr Thr Ile Ala Pro Ala
                245

<210> SEQ ID NO 49
<211> LENGTH: 245
<212> TYPE: PRT
<213> ORGANISM: Streptomyces tsukubaensis

<400> SEQUENCE: 49

Met Ala Val Asn Arg Arg Leu Phe Leu Gly Gly Phe Thr Ala Gly Ala
 1               5                  10                  15

Val Thr Val Ala Ala Gly Thr Ala Thr Pro Ala Ala Ala Ala Ala Ala
                20                  25                  30

Gln Gly Pro Thr Thr Thr Phe Asp Gly Pro Val Ala Glu Arg Phe
            35                  40                  45

Ser Thr Asn Ser Thr Val Asn Ser Ala Phe Leu Lys Thr Thr Ser Thr
 50                  55                  60

Thr Glu His Ala Ala Thr Val Tyr Gln Ala Gly Thr Ser Gly Ser Gly
 65                  70                  75                  80

Val Ala Leu Asn Ile Val Ser Asp Asn Pro Asp Asn Ser Ala Val Tyr
                 85                  90                  95

Leu Thr Gly Arg Glu Lys Thr Arg Gly Thr Leu Lys Ile Ser His Ile
            100                 105                 110

Gly His Ala Asp Gly Ser Asp Ala Ala Ala Val Ser Ile Asp
        115                 120                 125

Leu Lys Thr Ala Gly Thr Ala Thr Gln Gly Ile Phe Leu Thr Ala Thr
130                 135                 140

Asp Gly Ala Thr Thr Gly Asn Leu Ile Cys Leu Arg Asn Asn Gly Arg
145                 150                 155                 160

Asp Asp Phe Val Val Lys Gly Ser Gly Arg Val Gly Ile Gly Leu Ala
                165                 170                 175
```

```
Val Gly Ser Ala Pro Trp Ser Gln Leu His Val Val Gln Arg Pro Gly
            180                 185                 190

Ala Asp Ser Ala Leu Met Val Glu Gly Ala Val Arg Ile Val Asp Ala
            195                 200                 205

Ala Thr Val Pro Thr Ala Val Asp Ser Lys Gly Gly Thr Leu Tyr
            210                 215                 220

Ala Gln Gly Gly Glu Leu Met Trp Arg Ser Ala Asn Gly Asn Val Thr
225                 230                 235                 240

Arg Ile Ala Ser Ala
                245

<210> SEQ ID NO 50
<211> LENGTH: 125
<212> TYPE: PRT
<213> ORGANISM: Streptomyces pristinaespiralis

<400> SEQUENCE: 50

Phe Asp Gly Pro Val Val Ala Glu Gly Phe Arg Thr Asp Ser Thr Val
1               5                   10                  15

Lys Ser Ala Phe Phe Lys Thr Thr Ser Thr Thr Glu His Ala Val Thr
            20                  25                  30

Ala Tyr Gln Ala Gly Thr Ser Gly Ser Gly Val Ala Leu Asn Val Val
            35                  40                  45

Ser Lys Asn Pro Gly Asp Ser Ala Met Tyr Leu Ser Gly Thr Glu Lys
        50                  55                  60

Ala His Gly Thr Leu Lys Ile Ser His Thr Gly His Ala Asp Gly Ser
65                  70                  75                  80

Asp Glu Lys Ala Ser Ala Leu Ser Ile Asp Leu Leu Thr Ala Gly Thr
                85                  90                  95

Ala Ala Gln Gly Ile Phe Val Lys Ala Gly Asn Gly Pro Thr Thr Gly
            100                 105                 110

Asn Leu Ile Cys Leu Arg Asn Asn Ala Arg Asp Asp Phe
            115                 120                 125

<210> SEQ ID NO 51
<211> LENGTH: 131
<212> TYPE: PRT
<213> ORGANISM: Streptomyces tsukubaensis

<400> SEQUENCE: 51

Phe Asp Gly Pro Val Val Ala Glu Arg Phe Ser Thr Asn Ser Thr Val
1               5                   10                  15

Asn Ser Ala Phe Leu Lys Thr Thr Ser Thr Thr Glu His Ala Ala Thr
            20                  25                  30

Val Tyr Gln Ala Gly Thr Ser Gly Ser Gly Val Ala Leu Asn Ile Val
            35                  40                  45

Ser Asp Asn Pro Asp Asn Ser Ala Val Tyr Leu Thr Gly Arg Glu Lys
        50                  55                  60

Thr Arg Gly Thr Leu Lys Ile Ser His Ile Gly His Ala Asp Gly Ser
65                  70                  75                  80

Asp Ala Asp Ala Ala Val Ser Ile Asp Leu Lys Thr Ala Gly Thr
                85                  90                  95

Ala Thr Gln Gly Ile Phe Leu Thr Ala Thr Asp Gly Ala Thr Thr Gly
            100                 105                 110
```

-continued

```
Asn Leu Ile Cys Leu Arg Asn Asn Gly Arg Asp Asp Phe Val Val Lys
        115                 120                 125
Gly Ser Gly
    130

<210> SEQ ID NO 52
<211> LENGTH: 5
<212> TYPE: PRT
<213> ORGANISM: Streptomyces koganeiensis

<400> SEQUENCE: 52

Phe Asp Gly Pro Val
1               5
```

BACTERIAL HYALURONIDASE AND PROCESS FOR ITS PRODUCTION

CROSS REFERENCE TO RELATED APPLICATIONS

This application is a Divisional of copending application Ser. No. 14/899,219, filed on Dec. 17, 2015, which was filed as PCT International Application No. PCT/IB2014/062193 on Jun. 13, 2014, which claims the benefit under 35 U.S.C. § 119(a) to Patent Application No. MI2013A000992, filed in ITALY on Jun. 17, 2013, all of which are hereby expressly incorporated by reference into the present application.

The present invention relates to a hyaluronidase derived from *S. koganeiensis*, its applications and a method for the production thereof.

Currently, the hyaluronidase used in the clinical field is of animal origin. While this product is suitably purified, it contains a number of contaminants that can induce immunogenic or allergic responses.

Hyaluronic acid is an essential component of the extracellular matrix and a quantitatively significant constituent of the interstitial barrier. Hyaluronidase is a hydrolytic enzyme that cleaves hyaluronic acid in D-glucuronic acid and N-acetyl glucosamine, increasing the permeability of the interstitial matrix. In a variable manner, it is also capable of degrading other acid mucopolysaccharides of the connective tissue. High concentrations of hyaluronidase can be found, for example, in the oral apparatus of leeches, in poison of snakes, bees, scorpions and in the culture supernatant of pathogenic bacteria such as pneumococci, haemolytic streptococci and *Staphylococcus aureus*. In human body, hyaluronidase is found in cornea, in ciliary body, in spleen, in skin and in testicles. High amounts of hyaluronidase are also found in spermatozoa, to which the enzyme allows to go beyond the barrier of hyaluronic acid that protects the ovule.

Hyaluronidase is used in medicine in the treatment of edema, local inflammation, hemorrhoids and chilblains. Furthermore, it is used in the pharmaceutical field to facilitate the transport and increase the dispersion and diffusion of certain high molecular weight active ingredients (antibodies, drug carrier nanoparticles, DNA for gene therapy, recombinant proteins) administered locally by subcutaneous injection, increasing the bioavailability thereof in amounts comparable to intravenous administration. [1] Previous studies have shown that nanoparticles with diameters up to 200 nm may undergo a strong increase in their transport through the interstitial space when administered concurrently or sequentially with the hyaluronidase enzyme [1]. The studies so far considered show how nanoparticles are able to express, in vitro, their functions, thus showing great potential in the therapeutic and diagnostic fields. However, one should consider, in vivo, the ability of nanoparticles to go beyond barriers due to the type of administration to be used in clinical practice (subcutaneous or gastrointestinal administration or toxicity by intravenous administration), their volume of distribution and their toxicity. The use of nanoparticle and hyaluronidase formulations could therefore represent an excellent and innovative starting point for the therapeutic and diagnostic future with the prospect that the drug carrier nanoparticles may finally be used in common clinical practice by local administration subcutaneously for treatment, for example, in oncology, ophthalmology and osteoarthritis.

Some types of cancer, including pancreas, breast, colon and prostate cancer, have been shown to accumulate high levels of hyaluronic acid (HA). This accumulation of HA in an abnormal way generates a protection network that surrounds certain types of cancers and supports them. This pathological accumulation of HA with other components of the matrix also increases the pressure of the interstitial fluid of the tumor, tumor vessel constriction, and creates a unique microenvironment that favors the growth of cancer cells as compared to normal cells. These mechanisms generate obstacles to the administration of drugs, inhibiting the potential effectiveness of many anti-cancer agents. By dismantling the HA component that determines the architecture of the tumor, hyaluronidase destroys this tumor microenvironment by opening previously restricted vessels that increase the blood flow to the tumor. This can allow anti-cancer therapeutic agents to be transported more efficiently to the tumor target, increasing their therapeutic efficacy. Hyaluronidase is also used in cosmetics for the treatment of granulomatous reactions or incorrect collocations, i.e. undesired, of hyaluronic acid, caused by fillers, and to dramatically improve the fibrosis condition present in cellulite.

Hyaluronidase, by segmenting the fibrotic component of cellulite, makes it softer with reduction of the orange peel effect, thus giving a more natural and pleasing appearance to the portion of skin subjected to the treatment. To date, hyaluronidase is the only real treatment, with therapeutic or non-therapeutic purposes, that can fight cellulite with satisfactory results. Previous studies have shown the efficacy of hyaluronidase in the treatment of cardiovascular diseases such as atherosclerosis [2], but the potential that hyaluronidase can have on blood pressure was unknown so far [3].

Clinical studies have demonstrated with electrocardiographic tests that these applications are scientifically supported, leading to study the effects that the human serum has on the activity of Wydase, a bovine testicular hyaluronidase that has been widely used in many clinical studies.

The following conclusions emerged from these clinical studies:

Only the use of a highly purified hyaluronidase has a high clinical value for the reduction of the extent of myocardial infarction [4].

Many groups have demonstrated that human blood contains a thermolabile inhibitor of bovine hyaluronidase [5,6].

These conclusions, despite the clinical studies have demonstrated the efficacy of hyaluronidase, have not led so far to the development of a hyaluronidase and/or new therapeutic agents based on hyaluronidase capable of ensuring an intravenous administration for the management of cardio-cerebrovascular diseases, limiting the use to some cardiovascular therapies, due to the high value of impurities, with those already available on the market. In the veterinary field, hyaluronidase is used in solutions comprising antibiotic substances for the treatment of animal diseases, such as bovine mastitis. To date, the production of bacterial or animal hyaluronidase on an industrial scale has been difficult, both for the low production and for the fact that the enzyme becomes unstable in aqueous solution and loses activity following purification.

In addition, many of the hyaluronidases produced industrially come from animal extracts (from bovine and ovine testicles) with a high risk of transmitting animal spongiform encephalopathy (the so-called "Mad Cow Disease"). Other industrial productions have produced hyaluronidase (human PH20) in soluble recombinant form starting from mammalian cells, improving the purity and reducing the risk of viral infections. [7] The object of the present invention is to provide a bacterial recombinant hyaluronidase having high purity for pharmaceutical and/or cosmetic applications.

An object of the present invention is to provide an enzyme that is stable in an aqueous solution even for long times and in the presence of proteolytic enzymes, that is completely devoid of the risk of transmitting animal spongiform encephalopathy and that has a high hyaluronidase activity also in the bloodstream without possibility of inhibition or viral or bacterial contamination, so as to allow its use also intravenously. Another object of the present invention is to provide a method for the preparation of hyaluronidase that is efficient, in a high yield and is applicable without difficulty on an industrial scale.

According to the present invention, these objects and others that will be better apparent hereinafter, are achieved by a method for the production of hyaluronidase isolated from *Streptomyces koganeiensis* ATCC 31394 comprising the amino acid sequence shown in SEQ. ID. No. 21 comprising the following steps:

a) inoculating a bacterial culture medium in a bioreactor with a inoculum of recombinant cells that contain at least one vector comprising the sequence shown as SEQ ID No. 41;

b) subjecting the content of the bioreactor of step a) to fermentation at a pH between 6.7 and 7.1 in the presence of a nourishment solution;

c) adding an inducer of the lac genes to the mixture of step b);

d) subjecting the mixture of step b) to an induction period of between 8 and 24 hours;

e) centrifuging the bacterial cells obtained in step d);

f) re-suspending the pellets obtained in step e) and subjecting the resulting suspension to osmotic shock;

g) extracting the periplasmic proteins by centrifugation of the suspension of step f);

h) purifying the protein fraction having hyaluronidase enzymatic activity obtained in step g) by a sequence of:

i. strong ion-exchange chromatography and isolation of the hyaluronidase enzymatic activity fraction;

ii. weak cation-exchange chromatography and isolation of the hyaluronidase enzymatic activity fraction; and iii. aromatic hydrophobic interaction chromatography and isolation of the hyaluronidase enzymatic activity fraction.

The objects of the invention are also achieved by a hyaluronidase from *Streptomyces koganeiensis* ATCC 31394 comprising the sequence SEQ ID No: 21, obtainable by said method.

The objects of the invention have also been achieved by a hyaluronidase from *Streptomyces koganeiensis* ATCC 31394 in a purified form and comprising the amino acid sequence shown in SEQ. ID. No. 21.

The objects of the invention have also been achieved by a polynucleotide comprising the nucleotide sequence shown in SEQ. ID. No. 17, encoding a bacterial hyaluronidase comprising the amino acid sequence in SEQ. ID. No. 21.

The objects of the invention have also been achieved by a genetically engineered recombinant vector comprising said polynucleotide.

The objects of the invention have been achieved by a host cell comprising said genetically engineered recombinant vector.

The objects of the invention are also achieved by a composition suitable for pharmaceutical or cosmetic use comprising said hyaluronidase from *Streptomyces koganeiensis* ATCC 31394 in a purified form and comprising the N-terminal amino acid sequence shown in SEQ. ID. No. 21, said hyaluronidase for use in the treatment and/or prevention of a disorder or disease, optionally in combination with at least another active ingredient, and non-therapeutic use thereof for cosmetic applications and/or for improving the aesthetic appearance.

Within the scope of the present invention, by "composition suitable for pharmaceutical or cosmetic use" means a solid, semisolid or liquid preparation, such as suspension or solution, comprising at least one active ingredient and at least one excipient as is known to the man skilled in the art.

Within the scope of the present invention, the definition of "polypeptide sequence" or "polynucleotide sequence" also includes sequences with a high degree of homology with the sequence indicated. As non-limiting examples, included within the scope of the invention are polypeptides that have at least 65%, 70%, 75%, 80%, 85%, 90%, 95%, 96%, 97%, 98%, 99% or more identity with the sequence shown in SEQ. ID. NO: 21, polynucleotides that have at least 70%, 75%, 80%, 85%, 90%, 95%, 96%, 97%, 98%, 99% or more identity with the sequence shown in SEQ. ID. NO: 17, and polynucleotides that have at least 70%, 75%, 80%, 85%, 90%, 95%, 96%, 97%, 98%, 99% or more identity with the sequence shown in SEQ. ID. NO: 41.

Within the scope of the present invention, by "hyaluronidase from *Streptomyces koganeiensis* ATCC 31394" it is meant hyaluronidase with a high degree of homology with the hyaluronidase originally isolated from the *Streptomyces koganeiensis* ATCC 31394 organism, that can be produced through biotechnological techniques also from micro-organisms other than *Streptomyces koganeiensis* ATCC 31394 (such as *E. coli* or *B. subtilis*).

If not otherwise stated, within the scope of the present invention the percentages are referred to the weight of a component on the total weight of the composition.

The following figures are provided to better describe the invention, without intending to limit the scope thereof.

FIGURES

FIG. 1: production curve of hyaluronidase from supernatant of *Streptomyces koganeiensis* culture relative to the time interval (T). Assay in 1% agarose gel of the profile of total RNA and DNA extracted from *S. koganeiensis* cells during the production step.

FIG. 2: sequence of the amplicon of about 550 bp obtained with internal primers MesFor2 and MesRev2 and in silico translation of the nucleotide sequence obtained in protein sequence.

Figure 3A:
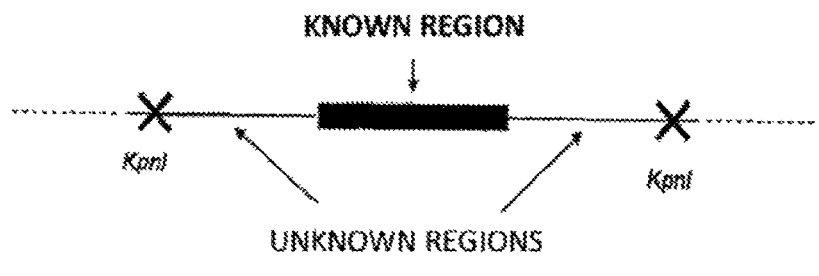
Figure 3B:
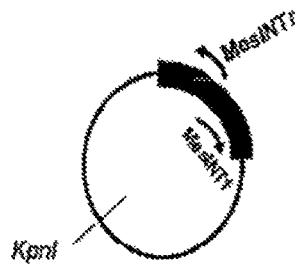
Figure 3C:
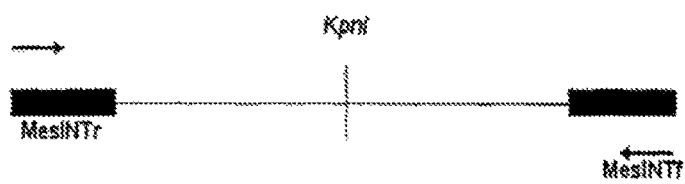

FIG. 3A, FIG. 3B, FIG. 3C: diagram of the Inverse Polymerase Chain Reaction (IPCR) method used to identify the sequences flanking in 5' and 3' the internal region of the *S. koganeiensis* gene encoding the hyaluronidase.

FIG. 4: complete identification of the entire nucleotide sequence of the gene encoding the CDS hyaluronidase portion of *S. koganeiensis*.

FIG. 5: sequence of the entire gene encoding the CDS hyaluronidase portion *S. koganeiensis* as cloned in the pCR-BluntII-MOUSE vector (Invitrogen).

Figure 6B:
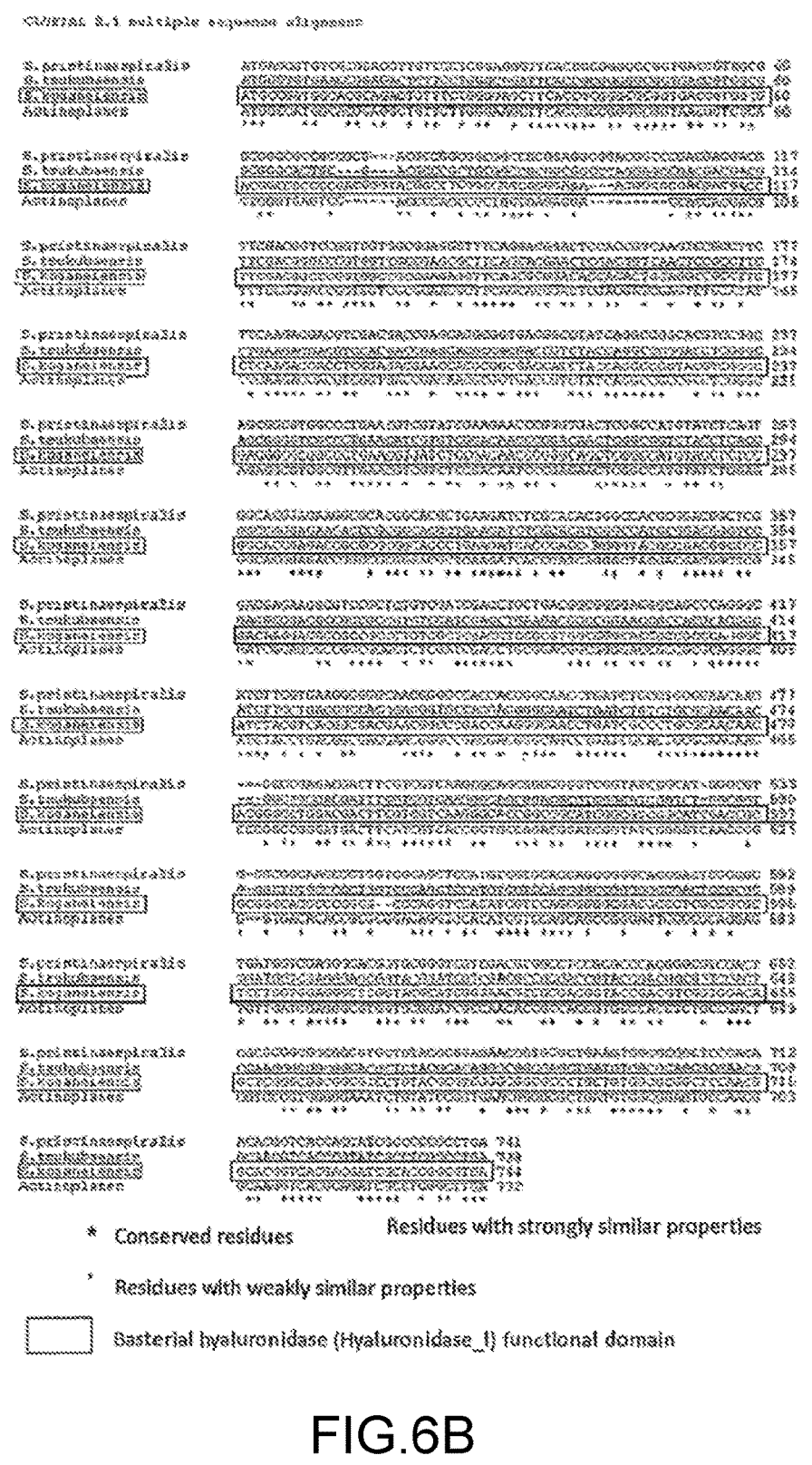

FIG. 6A: BLAST assay for sequence homologies between the amino acid sequence determined by the *S. koganeiensis* ATCC 31394 hyaluronidase and the amino acid sequences reported in web database. The sequences highlighted by the rectangle describe a functional domain of the bacterial hyaluronidase family. FIG. 6B: BLAST assay for sequence homologies between the nucleotide sequence determined by the *S. koganeiensis* ATCC 31394 hyaluronidase and the nucleotide sequences reported in web database.

FIG. 7A: functional characterization on the protein sequence of the hyaluronidase from *S. koganeiensis*. FIG.

7B: functional characterization on the protein sequence of the hyaluronidase from *Actinoplanes* sp. SE 50/110, *Streptomyces pristinaespiralis* ATCC 25486, *Streptomyces tsukubaensis* NRRL18488.

Figure 8A:
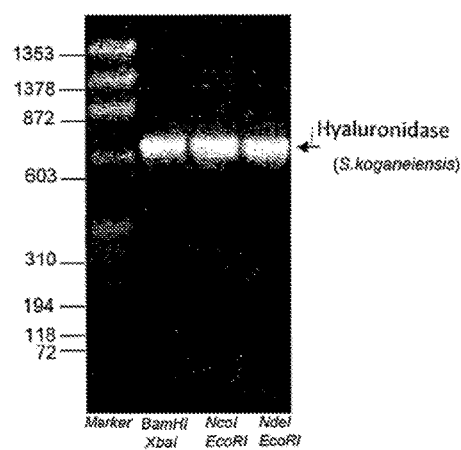
Figure 8B:

FIG. 8A, FIG. 8B: DNA fragment encoding hyaluronidase and expression plasmids thereof used for cloning were both cut with established restriction enzymes. The fragments obtained were analyzed in 1% agarose gel and stained with ethidium bromide. After staining, the gel was acquired by a laboratory image capturing device ImageQuant 300 TL (GE Healthcare) while (quantitative and qualitative) assays were performed using the image analysis software ImageQuant TL (GE Healthcare).

Figure 9A:
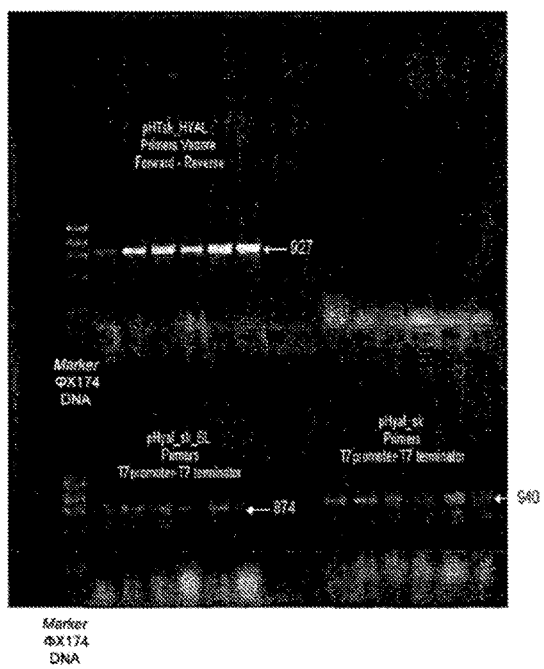
Figure 9B:
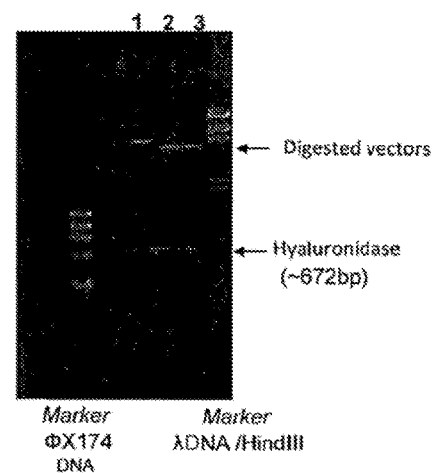

FIG. 9A, FIG. 9B: Screening by PCR and digestion with restriction enzymes, of the DNA fragment encoding the hyaluronidase cloned into expression plasmids. The fragments obtained were analyzed in 1% agarose gel with the image analysis software ImageQuant TL (GE Healthcare) after staining with ethidium bromide and acquisition.

Figure 10:
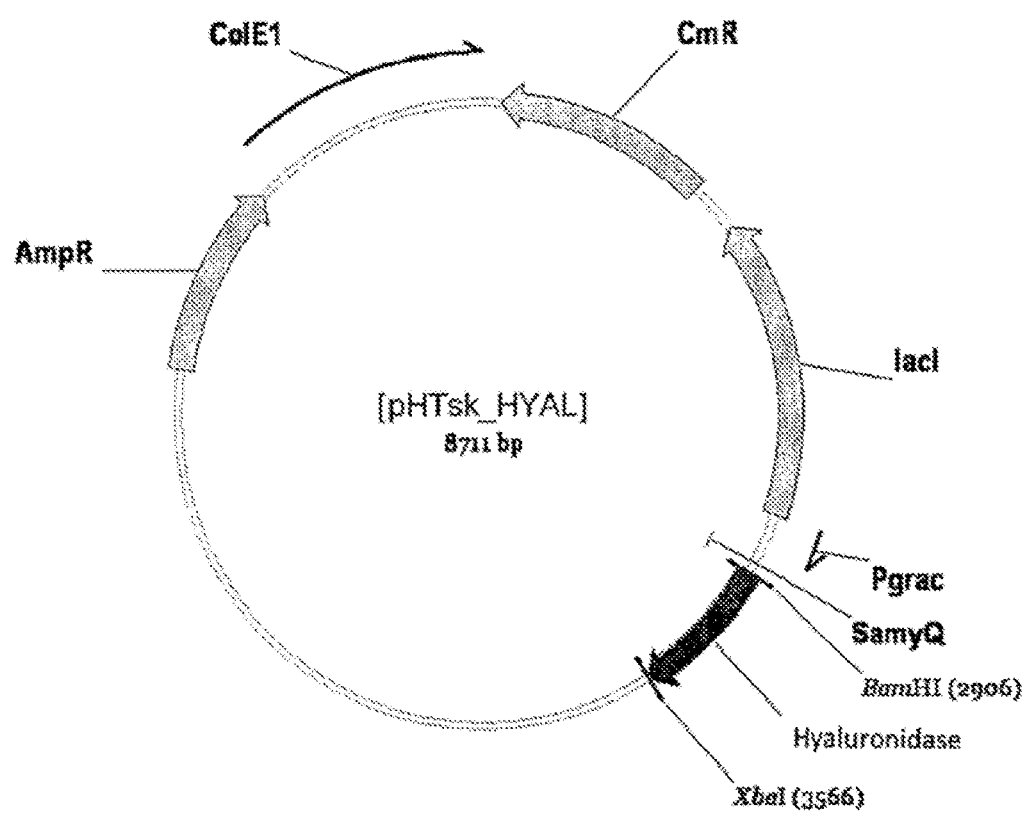

FIG. 10: the figure shows the map of the pHTsk HYAL plasmid: Pgrac promoter, laI gene (lacI repressor), $Amp^R$ gene for resistance to ampicillin, $Cm^R$ gene for resistance to chloramphenicol, ColE1 origin of replication of *E. coli*, SamyQ signal peptide of amyQ and hyaluronidase gene encoding the *S. koganeiensis* hyaluronidase, BamHI and XbaI unique restriction sites used for cloning hyaluronidase.

Figure 11:
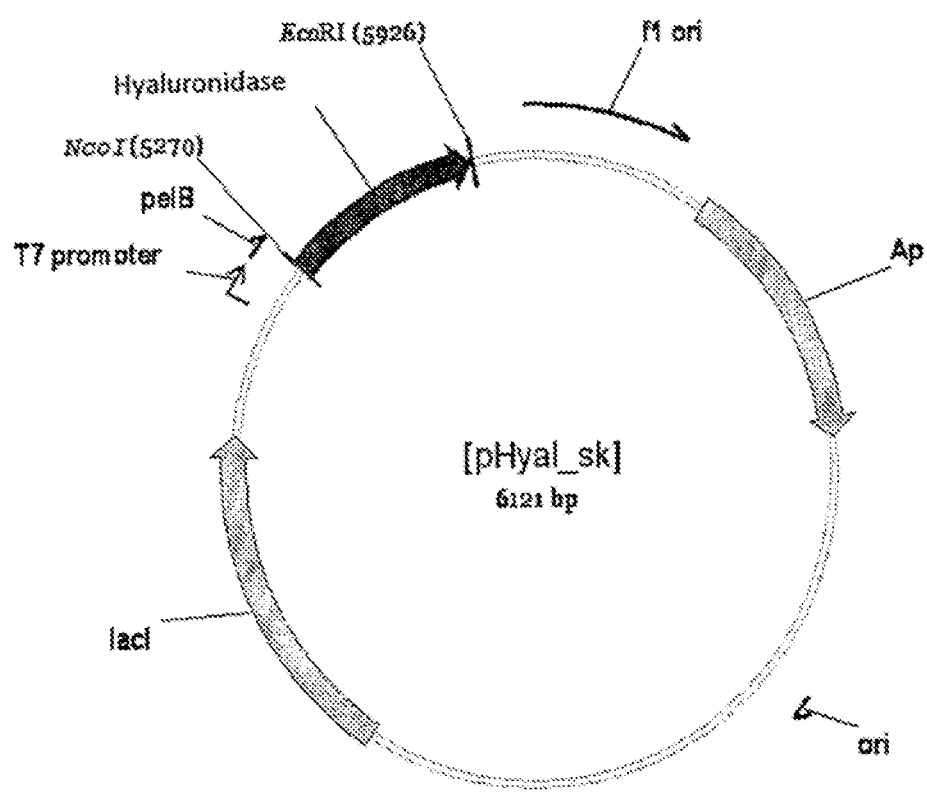

FIG. 11: the figure shows the map of the pHyal_sk plasmid: ori origin of replication of *E. coli*, Ap gene for ampicillin resistance, T7 promoter, laI gene (lacI repressor), pelB signal peptide, hyaluronidase gene encoding the *S. koganeiensis* hyaluronidase, NcoI and EcoRI unique restriction sites used for cloning the hyaluronidase.

Figure 12:
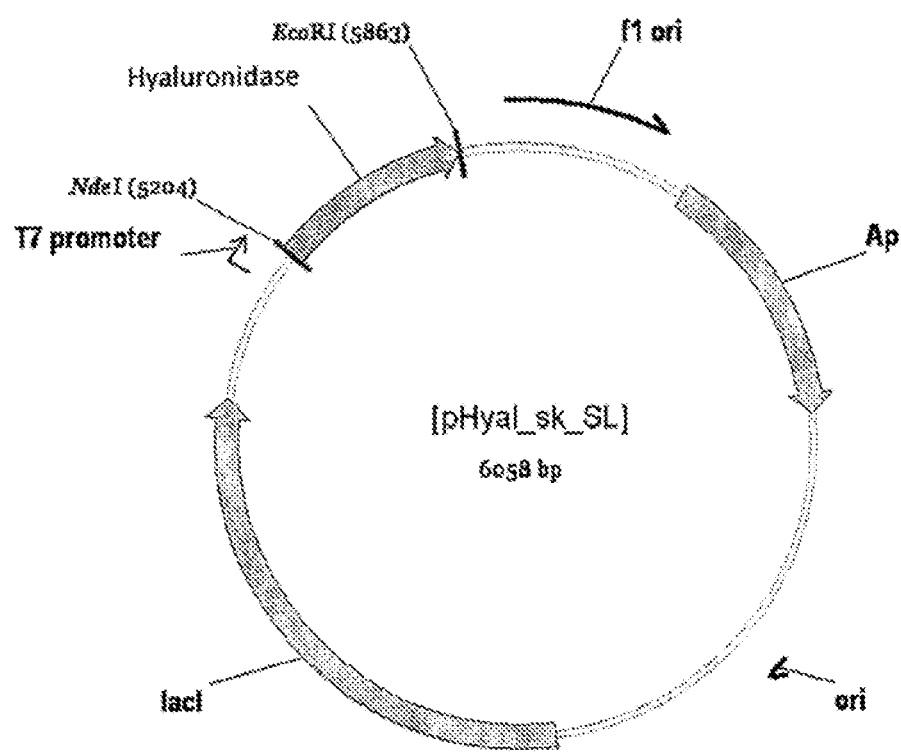

FIG. 12: the figure shows the map of the pHyal_sk_SL plasmid: ori origin of replication of *E. coli*, Ap gene for ampicillin resistance, T7 promoter, laI gene (lacI repressor), hyaluronidase gene encoding the *S. koganeiensis* hyaluronidase, NdeI and EcoRI unique restriction sites used for cloning the hyaluronidase.

Figure 13A:
Figure 13B:

FIG. 13A: the figure shows the nucleotide sequence of the Open Reading Frame (ORF) encoding the hyaluronidase protein of *S. koganeiensis* cloned into vector pHT43 (MO-BITEC). FIG. 13B: the figure shows the nucleotide sequence of the ORF encoding the hyaluronidase protein of *S. koganeiensis* cloned into vector pET22b(+) (Novagen).

Figure 13C:
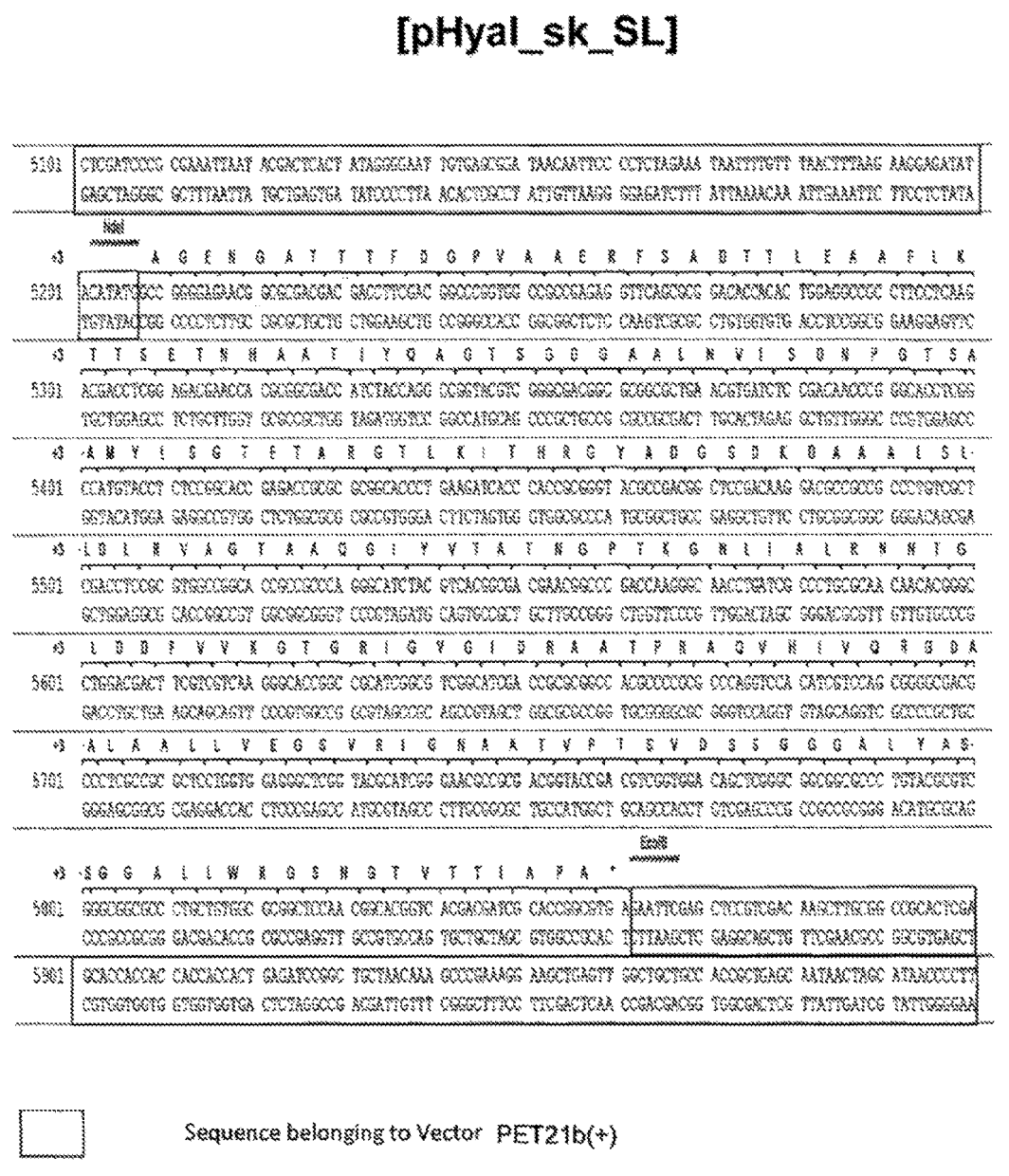

FIG. 13C: the figure shows the nucleotide sequence of the ORF encoding the hyaluronidase protein of *S. koganeiensis* cloned into vector pET21b(+) (Novagen).

Figure 14:
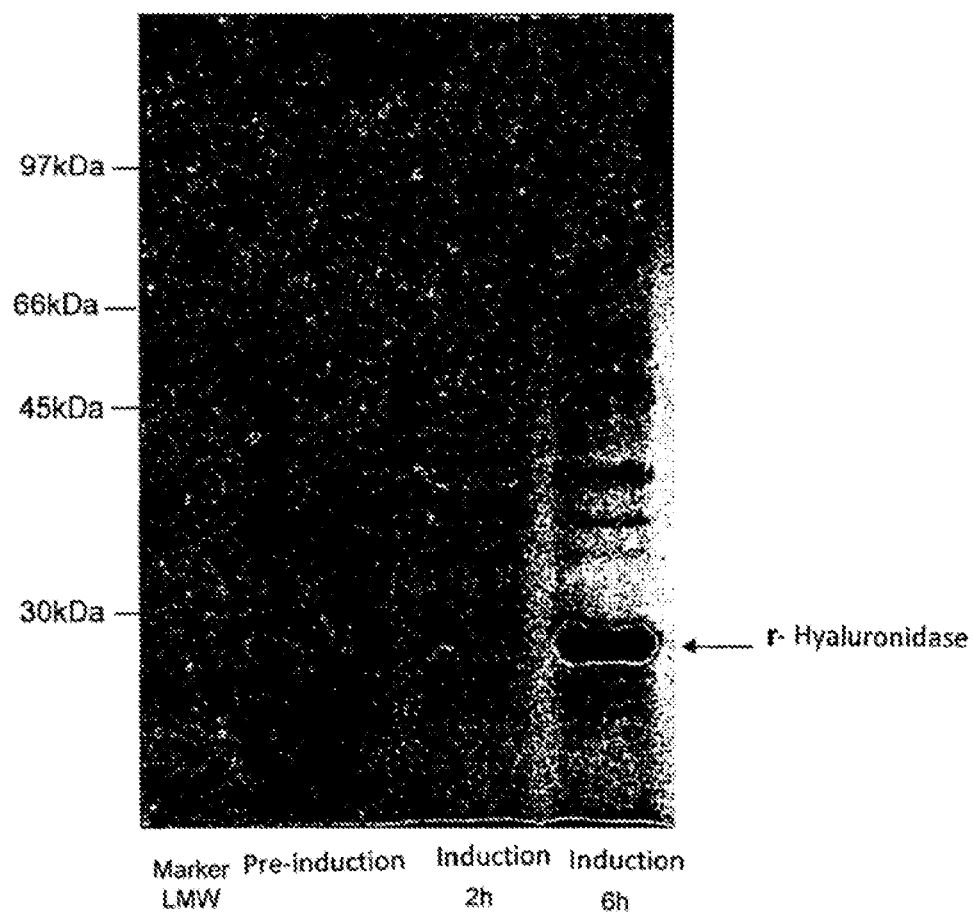

FIG. 14: assessment in SDS-PAGE at 12% of the expression of the hyaluronidase recombinant (*E. coli*, BL21 (DE3) containing plasmid pHyal_sk) after induction with 1 mM IPTG compared to the protein profile of the pre-induced sample.

Figure 15:
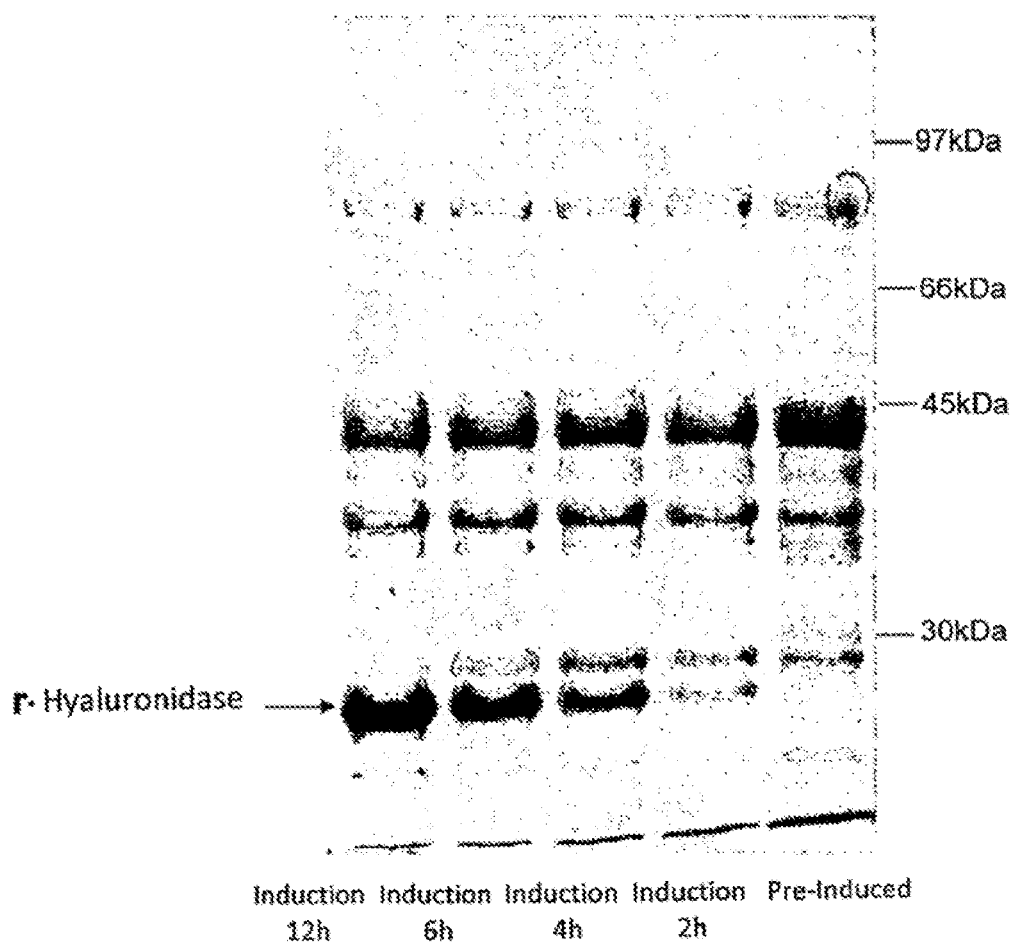

FIG. 15: assessment in SDS-PAGE at 12% of the expression of the hyaluronidase recombinant (*E. coli*, BL21 (DE3) containing plasmid pHyal_sk_SL) after induction with 1 mM IPTG compared to the protein profile of the pre-induced sample.

Figure 16:
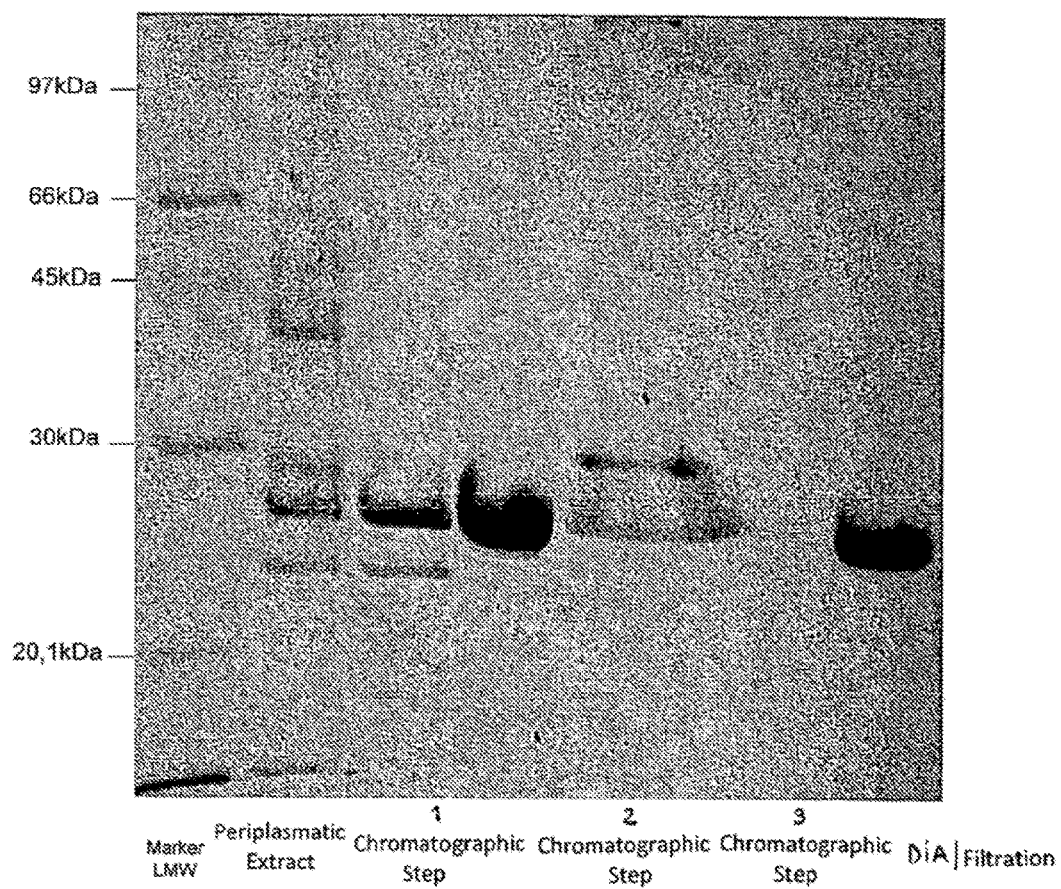

FIG. 16: protein profile in SDS-PAGE at 12% of the fractions obtained after each purification step according to the invention.

Figure 17A:
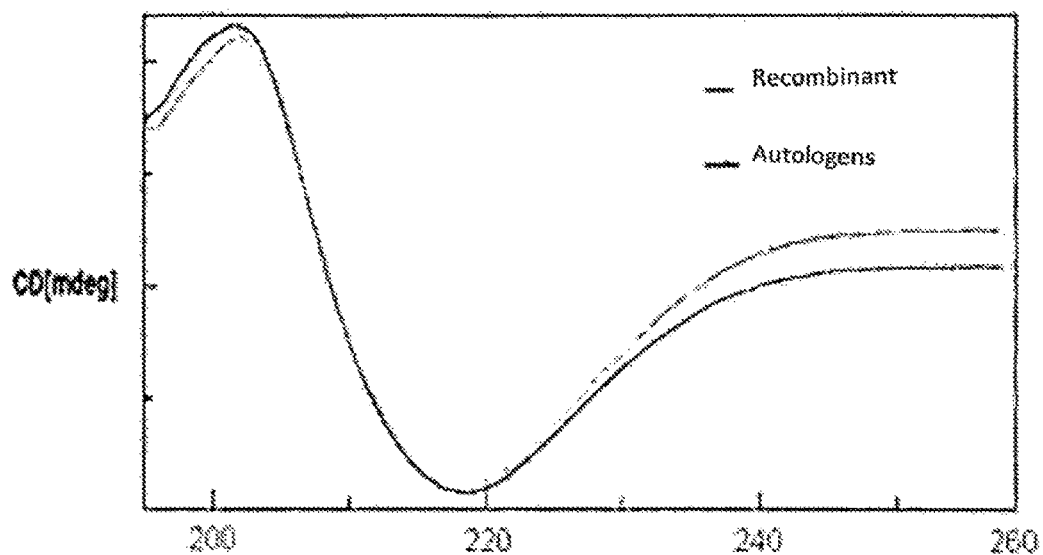
Figure 17B:
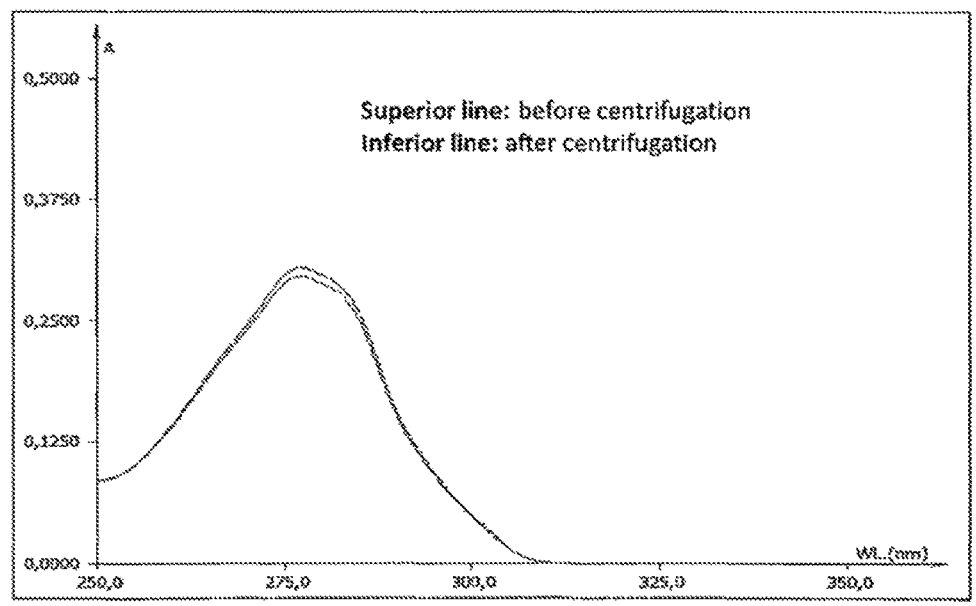

FIG. 17A: comparison of spectra at the circular dichroism of autologous and recombinant hyaluronidase. FIG. 17B: the respective UV spectra for the purified recombinant is shown. The UV spectra were analyzed before (upper line) and after (lower line) centrifugation in order to remove any aggregates present.

Figure 18:
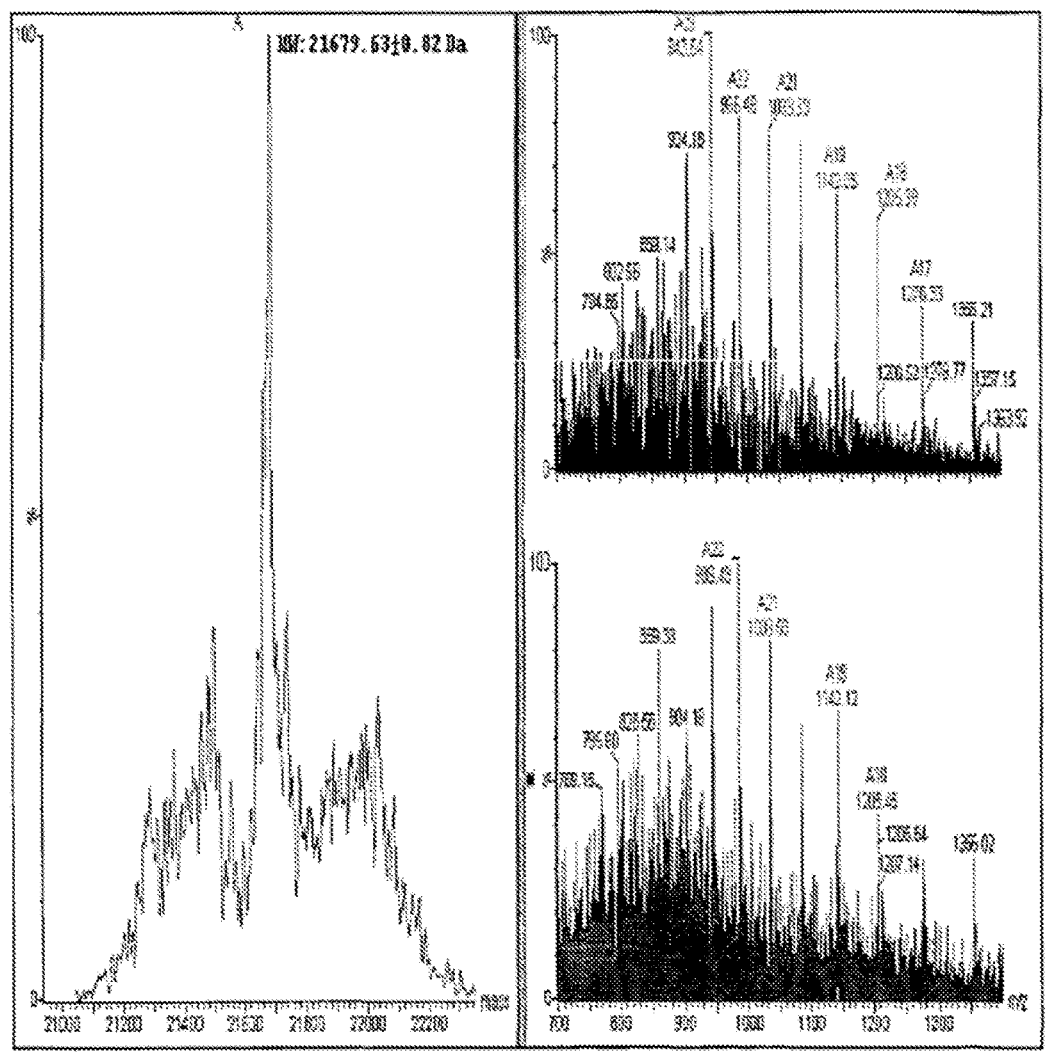

FIG. 18: molecular weight determination by mass spectrometry of the recombinant hyaluronidase obtained according to invention.

Figure 19:
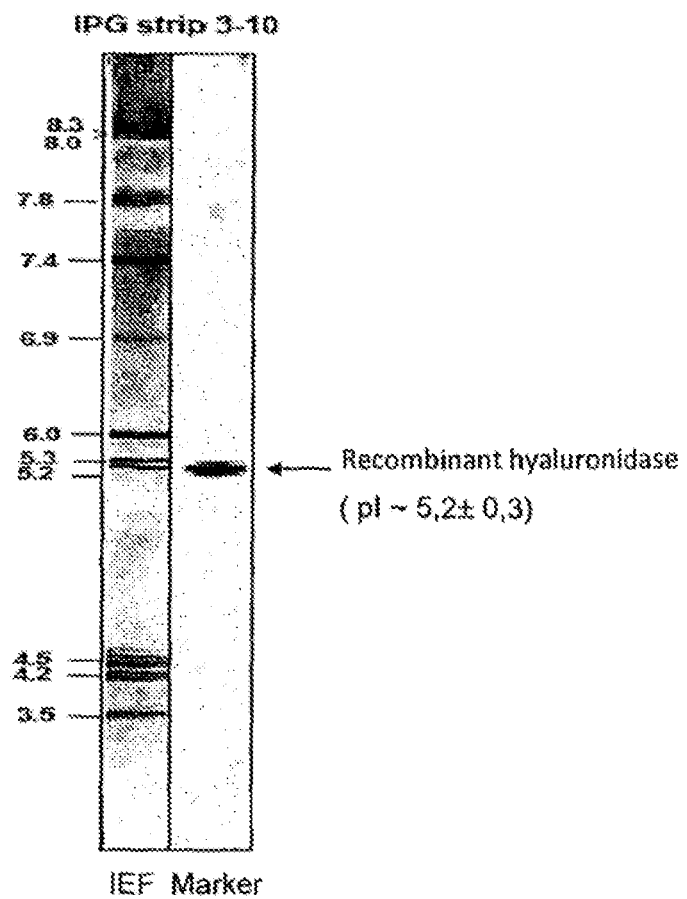

FIG. 19: determination of the isoelectric point of the recombinant hyaluronidase obtained according to the invention.

Figure 20:
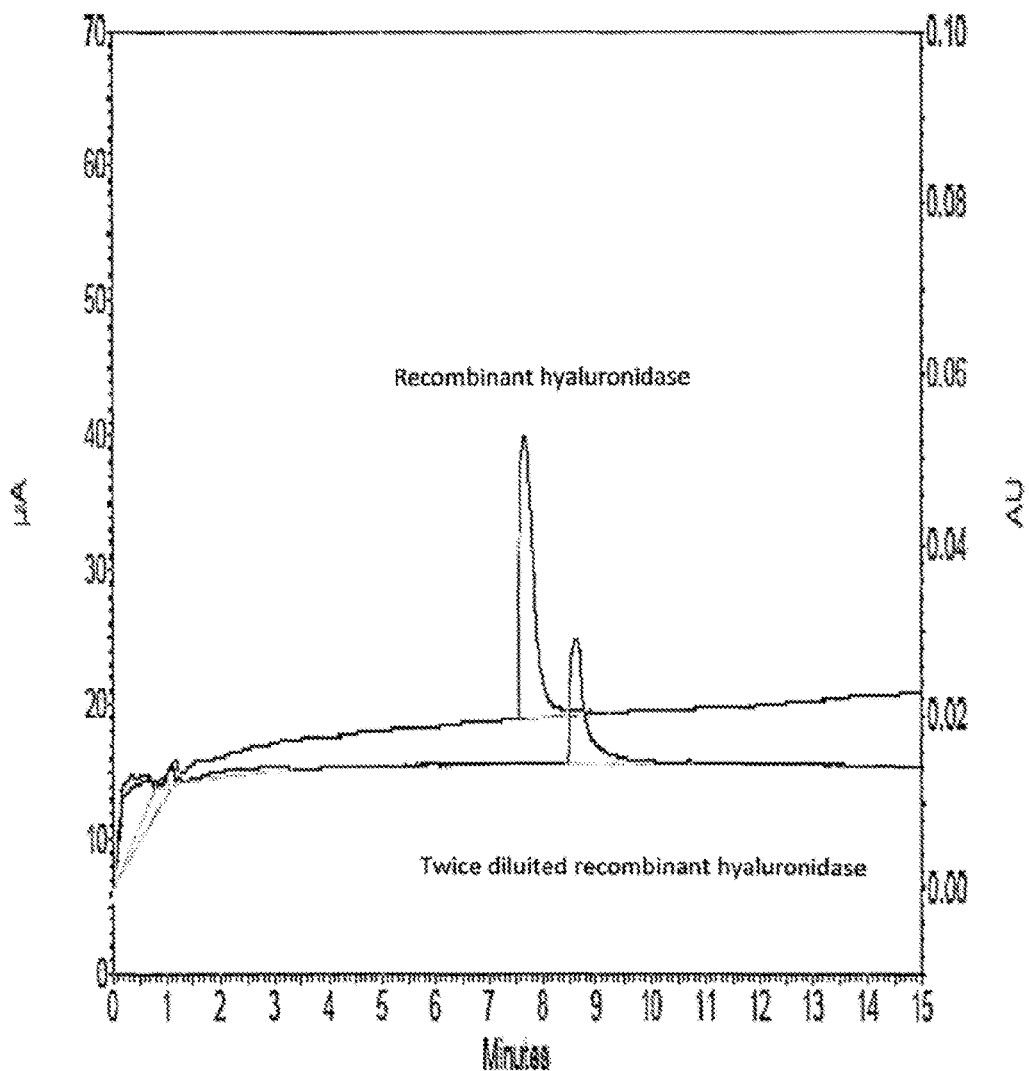

FIG. 20: capillary electrophoresis electropherogram of the sample of purified recombinant hyaluronidase according to the invention. The calculated concentration was approximately 1 mg/ml with 100% purity.

Figure 21A:
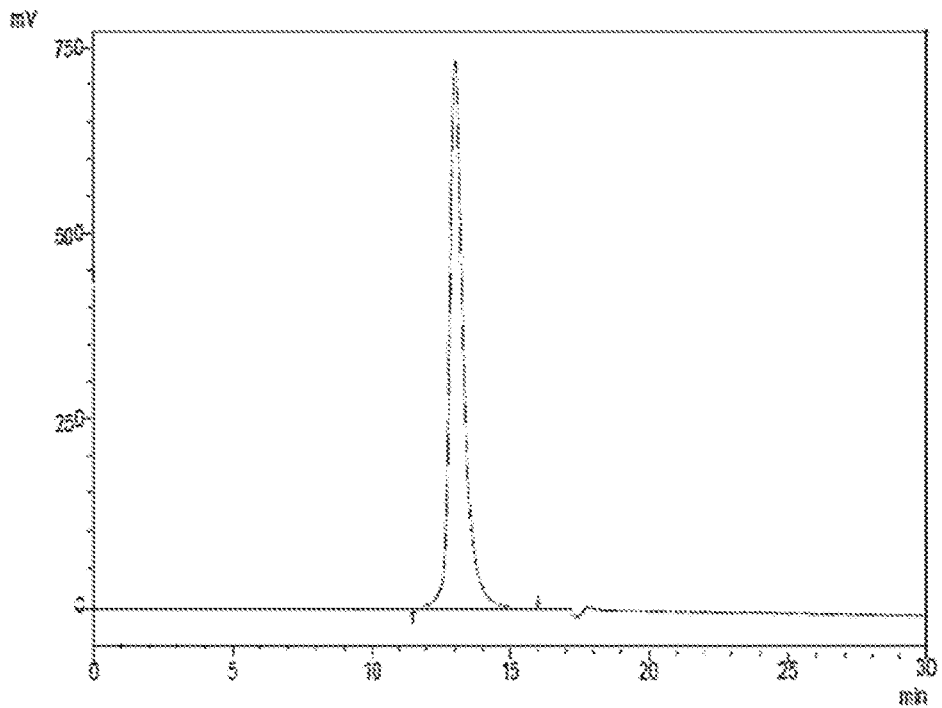
Figure 21B:
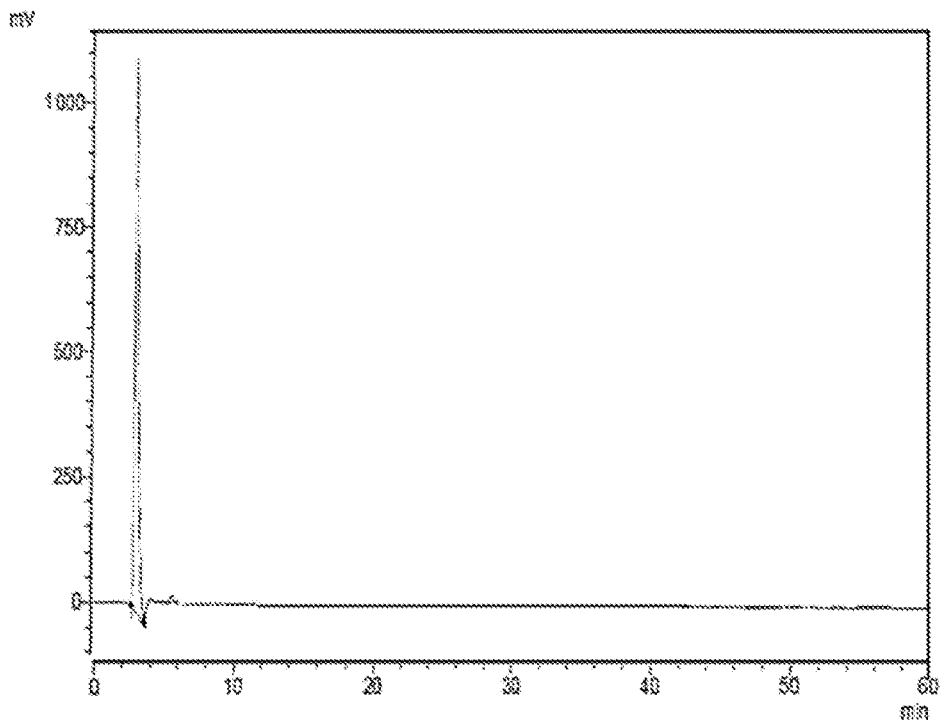

FIG. 21A and FIG. 21B: analysis of the purity of the purified recombinant hyaluronidase according to the invention by means of FIG. 21A: HPLC on gel filtration column Bio-Sil SEC, FIG. 21B: RP-HPLC on a hydrophobic phase (reversed) column.

Figure 22:
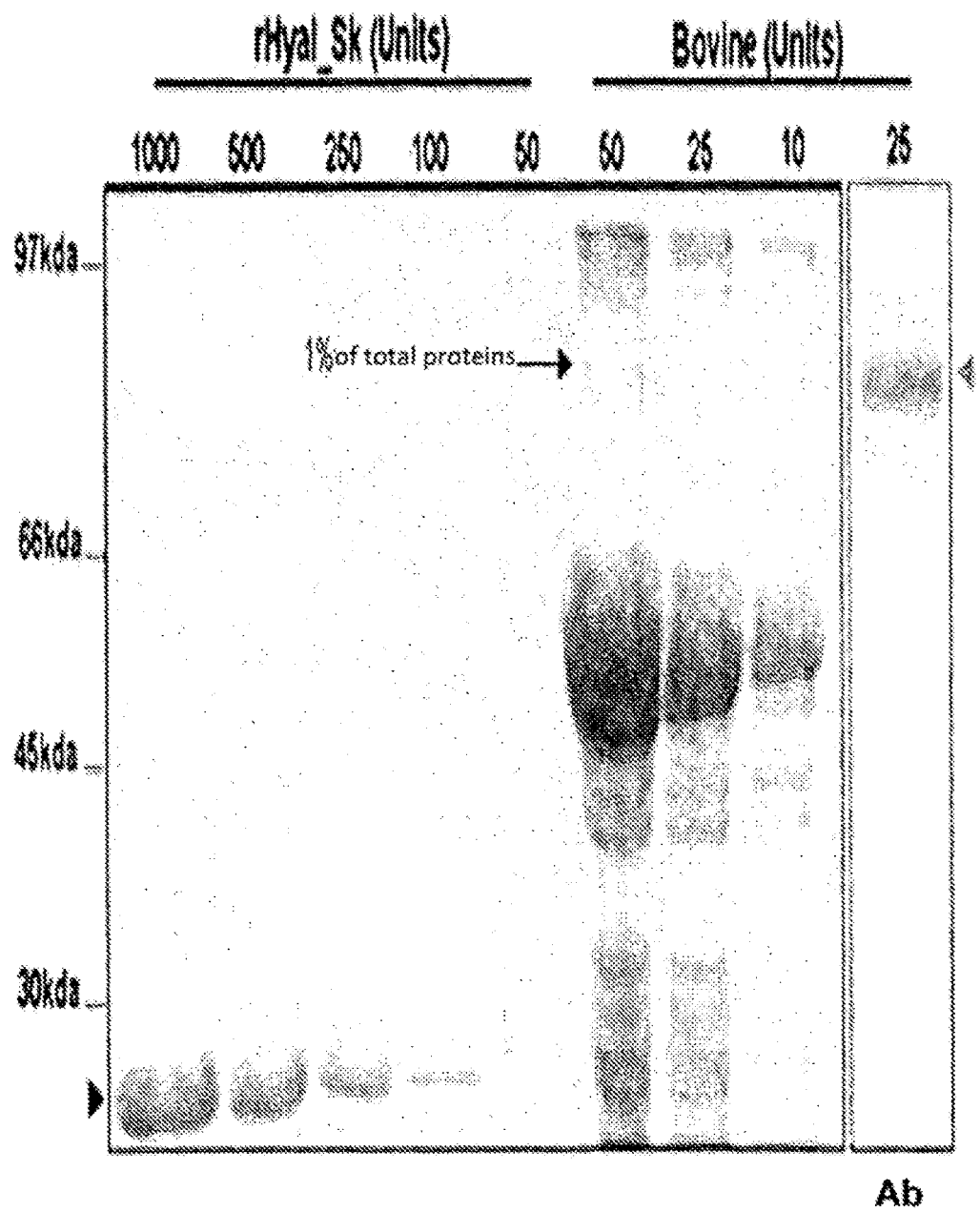

FIG. 22: SDS-PAGE 12%—the recombinant hyaluronidase produced and purified according to invention was charged with 1000, 500, 250, 100, and 50 units per lane and compared with 50, 25 and 10 units per lane of hyaluronidase from bovine testicles. Western blot analysis on the preparation of 25 units of the bovine hyaluronidase using the anti-hyaluronidase polyclonal antibody (Abnova), that revealed a single immunoreactive hyaluronidase band.

Figure 23:
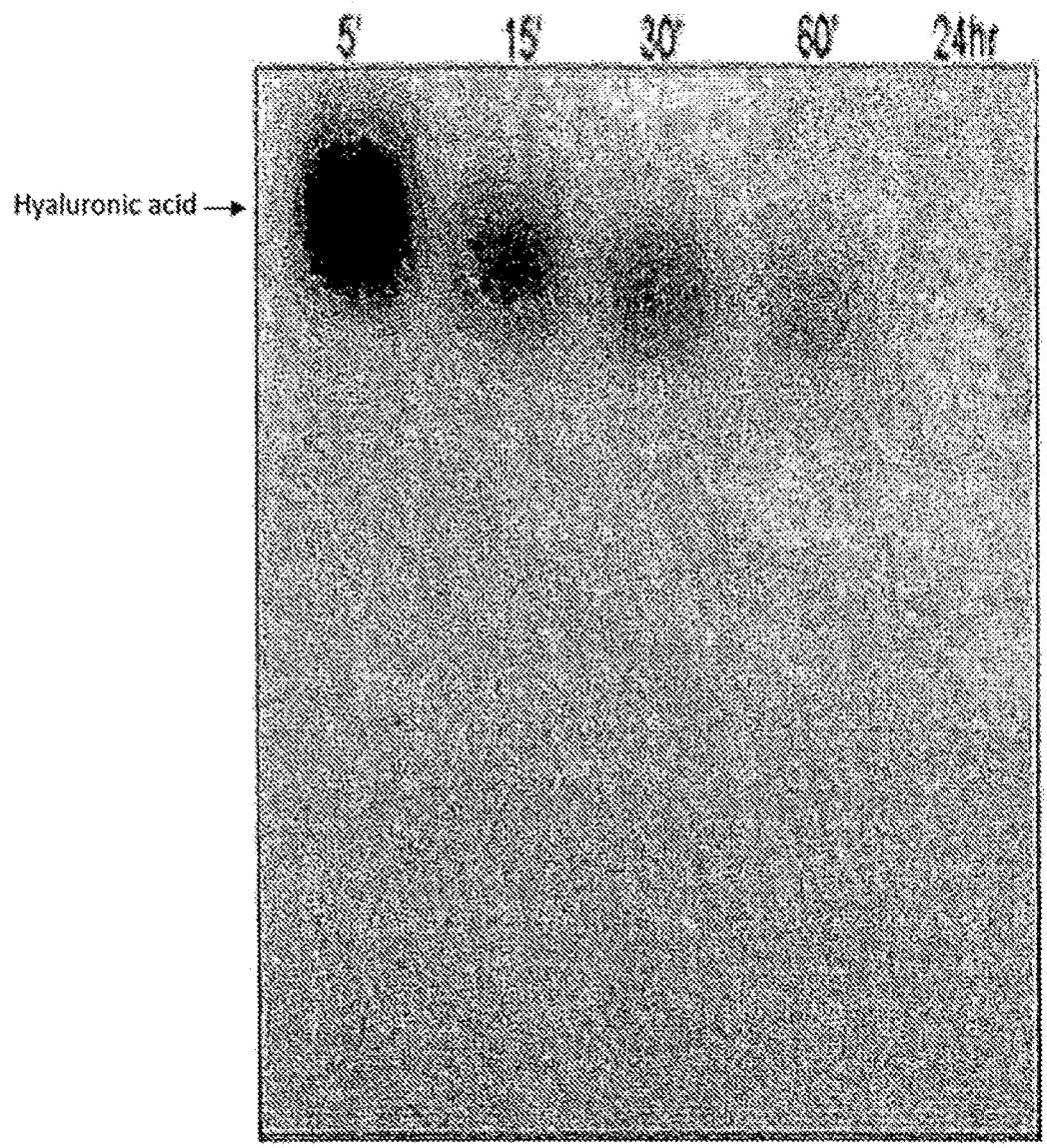

FIG. 23: electrophoresis in 1% agarose gel shows the depolymerization of the hyaluronic acid purified with 1 unit of recombinant hyaluronidase produced according to the invention at the times indicated ranging from 5 minutes to 24 hours.

Figure 24A:
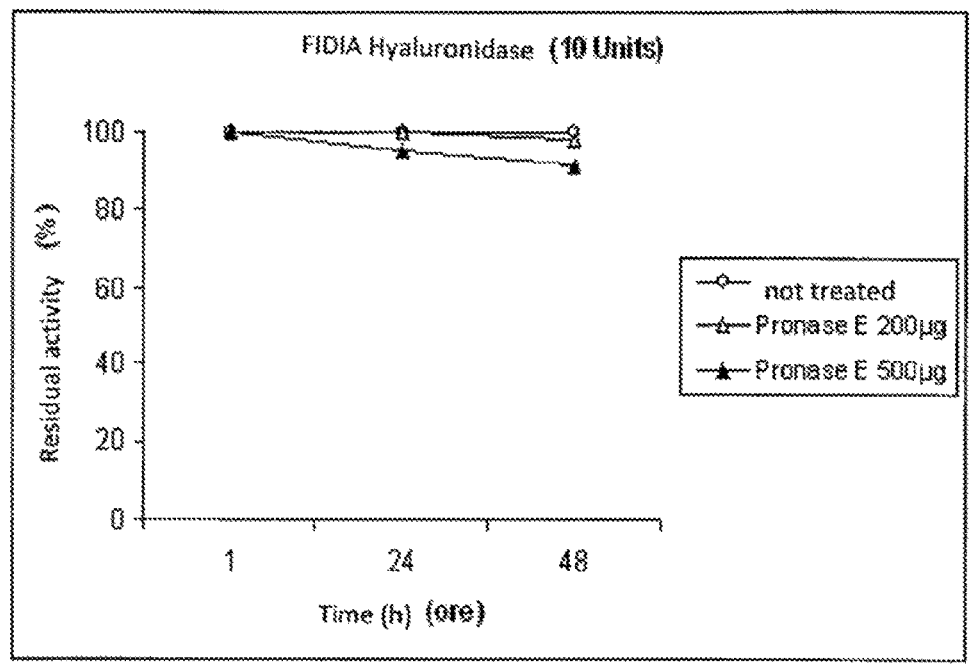
Figure 24B:
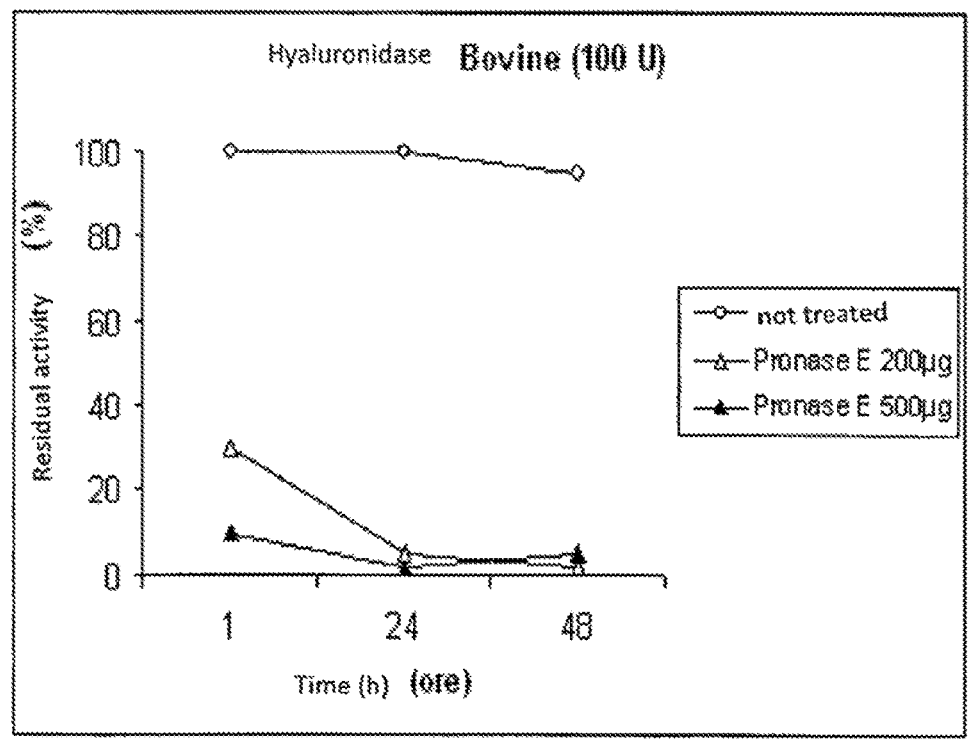

FIG. 24A and FIG. 24B: Stability of the recombinant hyaluronidase produced according to the invention and of the hyaluronidase from bovine testicles, against proteolytic enzymes.

Figure 25A:
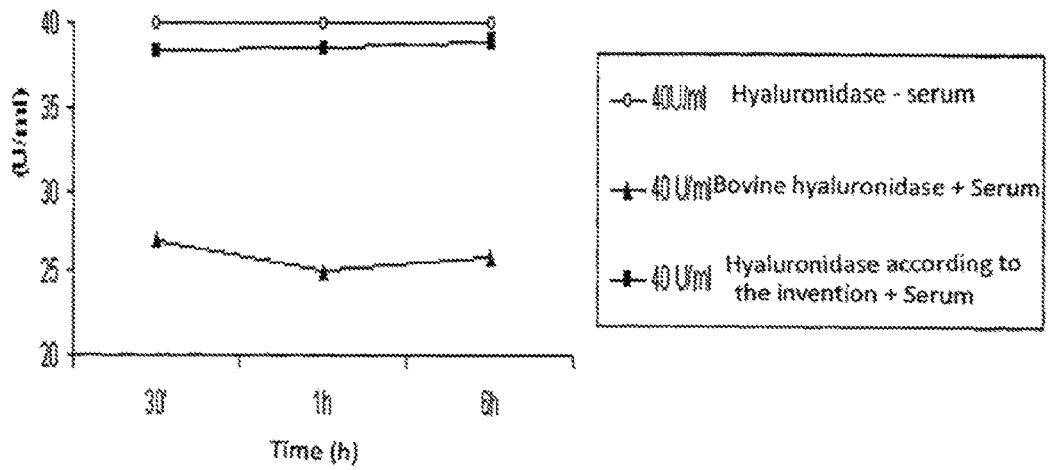
Figure 25B:
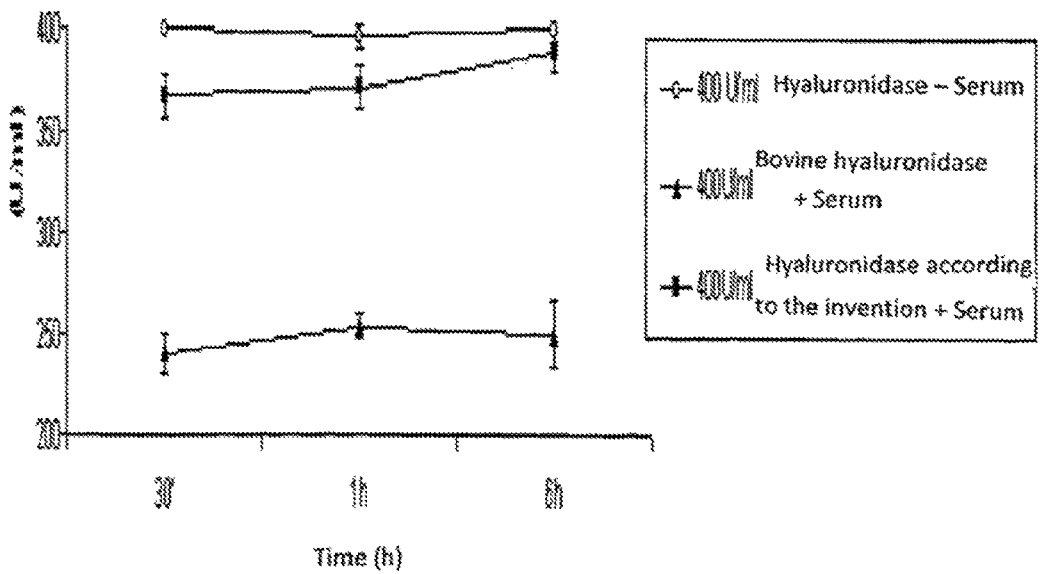

FIG. 25A and FIG. 25B: in vitro evaluation of the inhibition effect that the human and animal serum has on the enzyme activity of hyaluronidase (recombinant produced according to this invention and bovine hyaluronidase).

In one embodiment, the present invention relates to a method for the production of hyaluronidase isolated from *Streptomyces koganeiensis* ATCC 31394 comprising the amino acid sequence shown in SEQ. ID. No. 21 comprising the following steps:

a) inoculating a bacterial culture medium in a bioreactor with an inoculum of recombinant cells that contain at least one vector comprising the sequence shown as SEQ ID No. 41;

b) subjecting the content of the bioreactor of step a) to fermentation at a pH between 6.7 and 7.1 in the presence of a nourishment solution;

c) adding an inducer of the lac genes to the mixture of step b);

d) subjecting the mixture of step b) to an induction period of between 8 and 24 hours;

e) centrifuging the bacterial cells obtained in step d);

f) re-suspending the pellets obtained in step e) and subjecting the resulting suspension to osmotic shock;

g) extracting the periplasmic proteins by centrifugation of the suspension of step f);

h) purifying the protein fraction having hyaluronidase enzymatic activity obtained in step g) by a sequence of:
   i. strong ion-exchange chromatography and isolation of the hyaluronidase enzymatic activity fraction;
   ii. weak cation-exchange chromatography and isolation of the hyaluronidase enzymatic activity fraction; and
   iii. aromatic hydrophobic interaction chromatography and isolation of the hyaluronidase enzymatic activity fraction.

To completely eliminate the risk of transmission of animal spongiform encephalopathy, and since limited sources of hyaluronidase of a microbial origin are available, a bacterial strain was selected and isolated in previous studies capable of producing a high hyaluronidase enzyme activity [8].

The same bacterial strain was successfully used ([9]) for the production of hyaluronidase having all of the peculiar enzymatic features, but above all a degree of purity (>98%) much higher than that described in [8]. Comparative studies have in fact shown that what is obtained from [8] is actually a mixture of 68 different fractions, of which only one has a hyaluronidase activity. The higher purity of [9] is accompanied by a greater enzymatic activity, evaluated at the same concentration and values of T and pH.

Moreover, additional comparative studies have shown that the hyaluronidase described in [9], in contrast to what described in [8], retains its stability over time up to 24 months, even at different temperatures (5° C. and −20° C.), and is virtually unaffected by the activity of proteolytic enzymes with which it comes in contact after administration.

In order to ensure a better safety in the use of this bacterial enzyme in pharmaceutical applications, the isolated and characterized hyaluronidase from the original bacterial strain in [9] was produced in recombinant form using a non-pathogenic bacterial strain as a host cell defined as Generally Regarded as Safe (GRAS). The production of the bacterial recombinant from the "GRAS" micro-organism retains efficacy comparable to that of autologous hyaluronidase but with a higher amount of production per liter and with a substantially better profile of purity and safety, including the complete absence of the risk of viral transmission.

The method of the present invention allows to obtain high amounts of a high quality recombinant bacterial hyaluronidase for pharmaceutical applications. The high production of recombinant hyaluronidase in non-pathogenic microorganisms has the same efficacy as the traditional hyaluronidase but with a significantly better safety and profile, including the complete absence of the risk of transmitting animal spongiform encephalopathy.

The present invention describes the isolation of the entire gene encoding the hyaluronidase from the gram-positive bacterium *Streptomyces koganeiensis*, with the subsequent cloning and expression of the CDS fragment (encoding sequence, SEQ ID NO: 22). Furthermore, the present invention provides a method for the preparation in the fermenter, the purification and characterization of the recombinant hyaluronidase encoded and secreted in the periplasmic cell portion in a soluble form.

The recombinant protein thus obtained has a high hyaluronidase activity and has a high stability to proteolytic enzymes, is able to perform the total activity with its maximum bioavailability in the bloodstream without possibility of inhibition and bacterial and viral contamination. In its recombinant soluble form, it proves to be effective for use in applications not only for the preparation of pharmaceutical compositions in facilitating the subcutaneous administration of active ingredients or injectable fluids but also in therapeutic applications, for example in the treatment of pathologies such as hypertension, myocardial infarction, thrombotic events, cardio- and cerebro-vascular events and tumors, since it is unique with the features described by the invention with reference to all other hyaluronidases available to date.

The productions of known hyaluronidase originate from animal sources having a high risk of transmitting animal spongiform encephalopathy; due to this risk, and to the high instability of the animal-derived hyaluronidase, a bacterial strain is researched, selected and isolated capable of producing a hyaluronidase with a high enzyme activity.

In one aspect, the present invention relates to the isolation of the entire gene encoding the bacterial hyaluronidase (SEQ ID NO: 17) having amino acid sequence SEQ ID NO: 21, coming from the gram-positive bacterium *S. koganeiensis*, the consequent cloning and expression of the nucleotide sequence SEQ ID NO: 22 encoding the mature protein having the sequence SEQ ID NO: 21 in a specific bacterial host (e.g. *E. coli*), recognized to be an organism selected for the expression of recombinant proteins used in therapeutic, diagnostic and industrial applications. The invention describes the production of the protein using the fed-batch method for obtaining, in a fermenter, a high amount of recombinant hyaluronidase secreted in the periplasmic cell portion in a soluble form. The recombinant hyaluronidase thus produced is subjected to purification using three reproducible chromatographic steps (two ion exchange and one hydrophobic exchange). The enzyme is an innovative suitably purified soluble recombinant bacterial enzyme with a high hyaluronidase activity produced by fermentation of safe bacteria without the use of animal-derived cells and raw materials. Furthermore, the enzyme according to this invention is characterized by a sequence of 217 amino acids, by an isoelectric point (pI) of 5.2±0.5, by a high stability to proteolytic enzymes, by in vitro stability towards animal and human blood, by a high degree of purity and safety, and by the complete absence of the possibility of viral contamination. The hyaluronidase according to the invention can be obtained as follows: initially, the strain of *S. koganeiensis* was subjected to fermentation and the extracellular material was obtained from bacterium cells as previously described [9]. During the fermentation process, cell fractions are collected every 3-4 hours to assess the levels of DNA and RNA produced by standard methods (FIG. 1), while the other part of the fraction is stored at −80° C. in RNAprotect™ Bacteria Reagent (Qiagen), after being analyzed. At the end of fermentation, the supernatant containing the hyaluronidase was clarified, concentrated, dialyzed, purified and then enriched with the sole hyaluronidase component as previously described [9].

Hyaluronidase from *S. koganeiensis* thus isolated was digested with proteolytic enzymes (trypsin, chymotrypsin, Glu-C) and the fragments obtained after digestion were separated by HPLC. In this way, the information concerning the primary structure of the isolated hyaluronidase was obtained by sequencing the N-terminal portion of the fragments obtained after enzymatic digestion.

The following amino acid sequences were obtained from the N-terminal sequencing performed:

```
                                                (SEQ ID NO: 1)
        AGENGATTTFDGPVA (SEQ ID NO: 2)
        RFSADTTIEAAFIKTTSETIHAATIYK (SEQ ID NO: 3)
        GYADGSDKDAAALSLDLR (SEQ ID NO: 4)
        AQVHIVQR (SEQ ID NO: 5)
        IGNAATVPTSVDSSGGG
```

From the research done in a database, the homology of hyaluronidase from *S. koganeiensis* ATCC 31394 with an aforesaid protein (protein_id=ZP_06911952.1) of *Streptomyces pristinaespiralis* ATCC 25486 was identified. On the basis of the N-terminal sequence of the peptides obtained from the isolated protein according to this invention, it was possible to synthesize the corresponding oligonucleotides, that served to isolate the gene encoding hyaluronidase from the genome of *S. koganeiensis*.

The pellets of bacterial cells from fermentation [9] in the period of exponential production of hyaluronidase (FIG. 1) were treated for extraction and purification of DNA and RNA. The products thus obtained are analyzed qualitatively using a spectrophotometer and quantitatively by electrophoresis in agarose gels [12].

The identified and identical amino acid regions between *S. koganeiensis* and *S. pristinaespiralis* served for designing the oligonucleotides used to isolate an internal portion of the gene encoding the hyaluronidase from the genomic DNA used as template, yielding a PCR product with a single specific band of approximately 550 bp. The nucleotide sequencing of the fragment provided the sequence (SEQ ID NO: 8) shown in FIG. 2.

The inverse PCR technique (IPCR) was developed and performed to identify the nucleotide regions flanking the gene sequence thus identified (FIG. 3). The IPCR method using the pair of primers SEQ ID NO: 11 and SEQ ID NO: 12 allowed obtaining PCR products, respectively of about 700 and 1400 bp, which, once sequenced, provided accurate information on the entire gene encoding the hyaluronidase of *S. koganeiensis*. With this step, the identification of the nucleotide sequence of interest (SEQ ID NO: 13), shown in (FIG. 4) is completed.

A pair of primers designed on the non-coding sequences (SEQ ID NO: 14 and SEQ ID NO: 15) and flanking the entire gene encoding the hyaluronidase are used for the amplification of the entire gene (SEQ ID NO: 16) and the PCR product (FIG. 5) was cloned directly into the pCR®-BluntII-TOPO® (Invitrogen) vector in of *E. coli* cells. From the results obtained from the bioinformatics analysis it was observed that the entire length of the gene encoding the hyaluronidase from *S. koganeiensis* was of 744 bp (SEQ ID NO: 17) and that the length of the peptide sequence was estimated to be 247 amino acids (SEQ ID NO: 18). The gene contains a putative domain (SEQ ID NO: 19) of proteins belonging to the hyaluronidase family (Hyaluronidase_1), as evidenced by the search for homologies on a database. Moreover, the analysis of the sequence (SEQ ID NO: 18) using a specific tool indicated the presence of a signal sequence (signal peptide) of 30 amino acids (amino acids 1 to 30 (SEQ ID NO: 47), with the cleavage site between amino acid 30 and 31). The mature protein (SEQ ID NO: 21) therefore is 217 amino acids long (corresponding nucleotide sequence 651 bp (SEQ ID NO: 22)) and its predicted molecular weight (http://web.expasy.org/compute_pi/) is 21679.96 Da.

Finally, BLAST analysis for sequence homologies shows a partial homology between the determined amino acid sequence from hyaluronidase from *S. koganeiensis* ATCC 31394 (SEQ ID NO: 18) with some of the amino acid sequences of hypothetical proteins belonging to the Aactinobacteria phylum reported in web database.

There is sequence homology between a region of the sequence (SEQ ID NO: 27 and SEQ ID NO: 52) of the hyaluronidase from *S. koganeiensis* (according to the invention) and one of the modules present in the amino acid domain of murine CD44 that binds the hyaluronic acid (FIG. 7 (*a*)).

cDNA encoding hyaluronidase from *S. koganeiensis* according to the invention (SEQ ID NO: 41) was amplified by PCR starting from the plasmid pCR-BluntII-TOPO [sk_HYAL] and ligated, after being digested with restriction enzymes, in the different plasmids used according to this invention, for example:

| Vector | Primers used | Restriction enzymes | Length nucleotide cloned from (SEQ ID NO: 41) | Plasmid obtained |
|---|---|---|---|---|
| pHT43 | SEQ ID NO: 28<br>5'-gtaGGATCCGCCGGG<br>GAAACGGCGCGACGACGA-3'<br>SEQ ID NO: 29<br>5'-gacTCTAGATCACGCC<br>GGTGCGATCGTCGTGACC-3' | BamHI<br><br><br>XbaI | 672 bp | pHTsk_HYAL<br>(FIG. 13a) |
| pET22b (+) | SEQ ID NO: 32<br>5'-tggCCATGGCCGGGG<br>AGAACGGCGCGACGACGA+3'<br>SEQ ID NO: 33<br>5'-ctcGAATTCtcaCGCC<br>GGTGCGATCGTCGTGACC-3' | NcoI<br><br><br>EcoRI | 671 bp | pHyal_sk<br>(FIG. 13,b) |
| pET21b (+) | (SEQ ID NO: 36)<br>5'-ataCATATGGCCGGGGA<br>GAACGGCGCGACGACGA-3'<br>(SEQ ID NO: 37)<br>5'-ctcGAATTCtcaCGCCGG<br>TGCGATCGTCGTGACC-3' | NdeI<br><br><br>EcoRI | 672 bp | pHyal_sk_<br>SL<br>(FIG. 13,c) |
| pET24b (+) | (SEQ ID NO: 36)<br>5'-ataCATATGGCCGGGGA<br>GAACGGCGCGACGACGA-3'<br>(SEQ ID NO: 37)<br>5'-ctcGAATTCtcaCGCCGG<br>TGCGATCGTCGTGACC-3' | NdeI<br><br><br>EcoRI | 672 bp | pRH_sk |

After cloning and amplification in cells of *E. coli* strain DH5a, the genetically engineered vectors were extracted and purified to be separately transformed into bacterial expression cells. The vector pHTsk HYAL is transformed into cells, made competent, of *Bacillus subtilis* (WB800N-MOBITEC) while vectors pHyal_sk, pHyal_sk_SL and pRH_sk are transformed into cells, made competent, of *E. coli*, strain BL21 (DE3) and/or MG1655. All transformations were carried out by chemical processing [13]. The clones, both of *B. subtilis* and of *E. coli*, found to be positive for the presence of vectors containing the nucleotide fragment of hyaluronidase having the genetically correct cloned sequence (SEQ ID NO: 41) are tested for the ability to express the recombinant hyaluronidase in 500 ml cultures (example: 10.11).

Preferably, in the method according to the present invention the recombinant cell of step a) is selected from a cell of *Escherichia coli* and one of *Bacillus subtilis*.

Master Cell Bank and Working Cell Bank was developed on the producer recombinant strains and the aliquots of these 2 ml clones with 15% glycerol were introduced into cryogenic vials immediately stored at −80° C.

Hyaluronidase according to the invention can be produced in large amounts starting from small fermenters using both Batch (example 13) and Fed-Batch (example 14) culture methods as described in this invention (table 1).

etate) as an undesirable by-product that has numerous negative effects on the production of recombinant proteins. The amount of acetate which is formed during the fermentation phase is directly related to the amount of glucose consumed by the growing *E. coli* cells [15]. In the present invention, it was found that by using glycerol as a carbon source (non-fermentable low cost carbon source) instead of glucose, an approximately 3-fold increase is obtained in the fed-batch production process for the production of recombinant hyaluronidase. As a non-limiting example, the feed can be provided 6 hours after inoculation up to the nineteenth hour (induction time) with an exponential addition ratio. After induction with Isopropyl β-D-1-thiogalactopyranoside (IPTG), 1 mM final solution, the feed can be administered to the culture every hour and in the same amount as the last addition for 5 hours. The induction takes place 24 hours after inoculation and continues for 8-24 hours, typically 12 hours. The bacterial cells are collected after the the induction period, by centrifugation, and stored at −80° C. The cells of *E. coli* BL21 (DE3) transformed with the vector pHyal_sk_SL produce the recombinant form in the cell periplasm with a maximum concentration reached of about 2 g per liter of culture and an enzymatic activity greater than 87000 U/ml of culture ($7.5 \times 10^7$-$8.7 \times 10^7$ IU/l of culture) obtained after 12 hours of induction with 1 mM IPTG at 37° C. (Table 2).

TABLE 1

Plasmids and cloning strategies used in the present invention

| Strain | Plasmide | Plasmide description/ Cloning Strategy | Protein Localization | Production of soluble Hyaluronidase (g/L) |
|---|---|---|---|---|
| *B. subtilis* WB800N | pHTsk_HYAL | pHT43(+)SamyQ-(BamHI/XBaI)-Hyaluronidase | Supernatant | N.D. |
| *E. Coli* BL21DE3 | pHyal_sk | pET22b(+)-pelB-(NcoI/EcoRI)-Hyaluronidase | Cellular periplasma | ~0.1 |
| *E. Coli* BL21DE3 | pHyal_sk_SL | pET21b(+)-(NdeI/EcoRI)-Hyaluronidase | Cellular periplasma | ≥2 |
| *E. Coli* BL21DE3 | pETsk_Hyal | pET21b(+)-(BamHI/HindIII)-Hyaluronidase-His | Included bodies | ≤0.001 |
| *E. Coli* BL21DE3 | pET22Hyal | pET22b(+)-pelB-(MscI/EcoRI)-Hyaluronidasecellular periplasma | Cellular periplasma | ~0.35 |
| *E. Coli* MG1655 | PHyal_sk | pET22b(+)-pelB-(NcoI/EcoRI)-Hyaluronidase | Cellular periplasma | N.D. |

However the best results in terms of production, stability and repeatability, were found using fermentations with the fed-batch method. Ampicillin, neomycin, kanamycin or chloramphenicol may be used as antibiotic according to the features of the specific vectors.

For example, the clone of *E. coli* "BL21 (DE3)-pHyal_sk_SL" was inoculated starting from a vial (coming from the working cell bank stored at −80° C.) in fresh LB Miller culture medium (ratio 1/20 with respect to the fermentation volume) containing 50 μg/ml ampicillin and incubated at 37° C. at 150 rpm for 16-18 hours. The clone coming from the inoculum was grown in the fermenter on a minimum culture medium at pH 6.8.

A glycerol solution was preferably given as feed. During the fermentation process, *E. coli* generates acetic acid (ac-

TABLE 2

Result of the fermentation batches of clone rHyal_Sk, carried out for the present invention

| | Batch | | | | |
|---|---|---|---|---|---|
| | 5C11 | 7C11 | 9C11 | 10C11 | 11C12 |
| Fermentation method | Batch | Fed-batch | Fed-batch | Fed-batch | Fed-batch |
| Hyaluronidase produced at the end of fermentation (g/L) | 0.5 | 1 | 1.5 | 1.2 | 2.1 |

TABLE 2-continued

Result of the fermentation batches of clone
rHyal_Sk, carried out for the present invention

| | Batch | | | | |
|---|---|---|---|---|---|
| | 5C11 | 7C11 | 9C11 | 10C11 | 11C12 |
| Final Biomass (O.D.$_{600\ nm}$) | 32.7 | 42 | 51.6 | 64 | 55 |
| Fermentation volume | 8 | 10 | 10 | 10 | 10 |
| Cellular Pellets (g/L) | 81.2 | 83 | 116 | 115 | 149 |
| Inoculum volume | 0.4 | 0.5 | 0.5 | 0.5 | 1 |
| Inoculum Biomass (O.D.$_{600\ nm}$) | 3 | 3 | 3 | 2 | 2.2 |
| Feed volume (L) | 0 | 1.5 | 1.5 | 1.5 | 2.5 |
| Feed Start (h) | / | 6 | 6 | 6 | 6 |
| Induction time (h) | 16 | 12 | 12 | 12 | 12 |
| Plasmide stability at the end of fermentation (%) | 100 | 95 | 100 | 100 | 100 |
| Total duration of fermentation (h) | ~22 | 36 | 36 | 36 | 36 |

The amount of hyaluronidase produced according to this invention was about 670-750 times higher than the autologous hyaluronidase produced in the fermenter as described in the previous patent [9].

The recombinant protein expressed by *E. coli*, in the different fermentation parameters, was analyzed by electrophoresis run in SDS-PAGE (12%) after staining with Coomassie Brilliant Blue G-250 (BIO-RAD, 161-0406) having a molecular weight of 24 kDa, while the enzymatic activity was analyzed by turbidimetric assay [16].

Recombinant hyaluronidase produced in the fermenter by the fed-batch method can be purified by a process comprising at least three chromatographic steps. In the preparation of the first purification, pellets stored at −80° C. (coming from the fed-batch fermentation of *E. coli* BL21 (DE3) transformed with the vector pHyal_sk_SL) are placed in an amount equivalent to 0.6 liters of fermentation product (approximately equivalent to the range of 80-90 g of cellular pellets reflecting approximately a production of 1-1.2 g/L of recombinant hyaluronidase) to equilibrate for 45 minutes at room temperature.

Once equilibrated, pellets were treated with a fresh solution (5° C.) for the dispersion of the pellet. The resuspended pellets were treated with a solution for osmotic shock to favour the extraction of periplasmic proteins. After the osmotic shock step, the product obtained was centrifuged and the resulting supernatant, once homogenised, is brought to pH 8 and filtered by gravity filters with 0.65 μm filters. The concentration of the extracted hyaluronidase was evaluated in SDS-PAGE resulting to be about 750-900 mg/total (16-22% of the total periplasmic proteins). The activity of the extracted recombinant hyaluronidase was instead assessed by Dorfman's turbidimetric method.

The protein fraction with hyaluronidase enzymatic activity thus obtained is subjected to strong anion exchange chromatography (example: Q sepharose XL).

The protein fraction with hyaluronidase enzymatic activity thus obtained is concentrated to 100 ml using Polyethersulfone (PES) filters with cut-off 5 kDa and diluted 10 times with 50 mM sodium acetate buffer at pH 4.

The protein fraction with hyaluronidase enzymatic activity thus obtained was subjected to weak cation exchange chromatography (example: CM-Sepharose® Fast Flow).

The protein fraction with hyaluronidase enzymatic activity thus obtained was concentrated to 100 ml using Polyethersulfone (PES) filters with cut-off 5 kDa and diluted 10 times with 50 mM sodium phosphate buffer with 1.5 mM ammonium sulphate, pH 7.

The protein fraction with hyaluronidase enzymatic activity thus obtained is subjected to aromatic hydrophobic interaction chromatography (example: phenylsepharose HP) and the eluted proteins from this last chromatographic step were collected in a single fraction having a volume of about 730 ml and subjected to hyaluronidase activity assay. After the analysis of the enzymatic activity, the eluted fraction was subjected to ultrafiltration and dialysis with 10 volumes of PBS 1× (Sigma-P4417) brought to a concentration of approximately 1 mg/ml and filtered with 0.2 μm filters, the protein concentration is determined by BCA Protein Assay Reagent Kit (PIERCE).

At the end of the purification process applied on approximately 1 L of the fermentation product, approximately 600-650 mg of recombinant hyaluronidase and an enzymatic activity greater than 2.6×10$^7$ U per liter of purified product from fermentation were obtained (Table 3).

TABLE 3

Result of the purified recombinant hyaluronidase according to the present invention

| Sample | | Hyaluronidase (U/ml) | Volume (ml) | Hyaluronidase (total U) | Production (%) | Hyaluronidase Total mg |
|---|---|---|---|---|---|---|
| Fermentation Product | Load | 48000 | 600 | 4.8 × 10$^7$ | 100 | 1000 |
| Periplasmic extraction | Eluted | 7600 | 5000 | 3.8 × 10$^7$ | 80 | 800 |
| Q-Sepharose ® XL | Load | 7600 | 5000 | 3.8 × 10$^7$ | 100 | 800 |
| | Eluted | 23100 | 950 | 2.2 × 10$^7$ | 57.8 | 462 |
| CM- Sepharose ® Fast Flow | Load | 23100 | 1000 | 2.2 × 10$^7$ | 100 | 462 |
| | Eluted | 57900 | 380 | 2.2 × 10$^7$ | 100 | 462 |
| Phenyl Sepharose ® HP | Load | 22000 | 1000 | 2.2 × 10$^7$ | 100 | 462 |
| | Eluted | 26000 | 730 | 1.9 × 10$^7$ | 88.8 | 410 |
| DIA/Filtration | Load | 26000 | 730 | 1.9 × 10$^7$ | 100 | 410 |
| | Conc. and DIA/Filtr. | 48570 | 350 | 1.7 × 10$^7$ | 93 | 381 |
| DIA/Filtration 5k | Load | 45300 | 375 | 1.7 × 10$^7$ | 100 | 381 |
| 0.22 μm Filtr. | Eluted | 45000 | 375 | 1.69 × 10$^7$ | 99.5 | 378 |
| Total production per culture liter (%) | | | | | 35 | |
| Total amounts per culture liter (IU) | | | | | 2.8 × 10$^7$ | |
| Total amounts per culture liter (mg) | | | | | 630 | |
| Total amounts per pellets gram (IU) | | | | | 2.1 × 10$^7$ | |
| Total amounts per pellets gram (mg) | | | | | 4.8 | |

In all fractions with hyaluronidase activity there was a marked protein band at about 24 kDa (FIG. 16), the band was subjected to SDS-PAGE electrophoresis on 12% gel and then to blotting on polyvinylidene difluoride membrane (BIO-RAD) and stained according to the instructions provided by the supplier. The hyaluronidase band was cleaved with a scalpel and loaded into the reaction chamber of the sequencer.

The sequencing of the N-terminal end thus carried out allowed establishing that the recombinant hyaluronidase produced according to the invention from the sample of E. coli transformed with the vector pHyal_sk_SL according to the invention provided chromatograms wherein a single N-terminal amino acid sequence was significantly present, allowing reconstructing the experimental sequence shown below: AGENGA (SEQ ID NO: 42).

The enzymatic potential of the hyaluronidase produced according to the invention (E. coli transformed with the vector pHyal_sk_SL) was evaluated by comparison with the enzyme activity of autologous hyaluronidase [9], using the enzymatic assay described [9] and the activity value was reported to be in both cases greater than $4 \times 10^4$ IU/mg protein.

In addition, in the analysis carried out by circular dichroism (CD), the overlay files black line (autologous hyaluronidase [9]) and gray line (heterologous hyaluronidase according to the invention) have a comparable profile, confirming the same protein structure for both samples (FIG. 17-a).

Compared to the prior art [9], the method according to the present invention allows:
- obtaining hyaluronidase of bacterial origin from a strain of E. coli well characterized as safe, rather than from Streptomyces koganeiensis, by recombinant technology (in place of that by extractive way) suitable for the production on an industrial scale, with production in the periplasm (in place of in extracellular matrix);
- reaching a surprisingly high maximum hyaluronidase activity, higher than 80000 U per milliliter of culture, against, for example, 130 U per milliliter of culture supernatant in the method of [9] and, in any case, clearly higher than those obtainable with other known processes;
- obtaining high-purity (>99%) hyaluronidase with only 3 chromatographic steps (instead of 5), with significant economic benefits and reduced processing times.

In another aspect, the present invention relates to a hyaluronidase from Streptomyces koganeiensis ATCC 31394 in a purified form and comprising the amino acid sequence shown in SEQ. ID. No. 21.

The protein of the present invention can be isolated and produced from Streptomyces koganeiensis or recombinantly produced, for example, from cultures of E. coli or Bacillus subtilis.

It was surprisingly found that, compared to the known protein from Streptomyces koganeiensis [9], the enzyme of the present invention has:
- a higher level of purity (99% versus 98%)
- a lower level of endotoxins (<0.5 U/mg instead of >0.5 U/mg);
- presence of the entire peptide sequence (and the corresponding nucleotide sequence), which does not have cysteine (thus reducing the possibility of yielding aggregates);
- greater stability in solution at 5° C. (100% stability at 24 months versus 94% at 24 months of the protein [9]);
- excellent stability at 20° C. (100% at 24 months), at pH 3-11.5 (tested up to 24 hours);
- maximum activity at physiological pH (around 7) and body temperature (about 37° C.);
- stability in the blood greater than 90%.

The hyaluronidase according to the present invention is a product derived from genetic engineering; so far, there was no availability of the entire protein-encoding gene, since there was no genomic or protein bank of the S. koganeiensis strain. Only with the method developed by the inventors described herein the nucleotide sequence encoding the protein has been identified and isolated. This nucleotide fragment is the first ever isolated and documented DNA sequence from this bacterial strain. At the industrial level, the possibility of being able to obtain the entire sequence of the gene encoding this hyaluronidase with a high enzymatic activity allows its use in different systems such as: vectors, systems of genomic integration and in cells, advantageous for the production and use of the enzyme in the pharmaceutical industry.

A further surprising result of the present invention is the very high yield of the process claimed, which was developed through a complex screening activity with different expression vectors, different types of insertion of the nucleotide fragment encoding the protein into the expression vector (i.e. the insertion of the fragment with some restriction sites with respect to others) and screening of the production in different cell lines. This activity, made even more complex since the nucleotide sequence encoding the protein was not available therefore not allowing to apply what was known to the man skilled in the art, has permitted the identification of the most suitable type of cloning, type of vector and expression cells for obtaining a production so unexpectedly high. The expression and production model for the recombinant protein according to the invention allows to obtain, at the end of the purification process, a pure protein with an endotoxin level of <0.5 U/mg of protein, using only three chromatographic steps instead of 5 as is in the known process (endotoxins >0.5 U/mg protein) [9].

The suitably purified enzyme is characterized by the assays whose results are listed in table 4.

TABLE 4

Result of the characterization assays of the recombinant hyaluronidase produced according to the present invention from clone rHyal_Sk.

| Analysis | Recombinant hyaluronidase |
|---|---|
| N-terminal Sequencing | 1 mg/ml AGENGA |
| Protein Assay (Lowry/BCA)Method | |
| 1SDS-Page | >99% |
| Isoelectric Focusing Theoretical I.P.5.5 | 90% (I.P.5.2 ± 0.4) |
| SEC-HPLC | 100% |
| RP-HPLC | >99% |
| Peptide Mapping (by LC-MS) Identity with reference aminoacid sequence | 94% (<90%) |
| Proprietary HCP Assays for E. coli Limit <100 ppm | 6.5-8.8 ppm |
| Threshold System (Proprietary DNA assays for E. coli Limit <300 pg/mg | 19 pg/mg |
| Chromo-LAL | <0.5 U/mg |
| Molar Extinction Coefficient | 12383 L * mol−1 * cm−1 ABS 280 (=1 g/l)0.570 |
| Mass Spectrometry of Proteins Theoretical MW 21679.96 | 21679.98 ± 0.82 |
| In Capillary (Zone) Purity Electrophoresis | 100% |

TABLE 4-continued

Result of the characterization assays of the
recombinant hyaluronidase produced according to the
present invention from clone rHyal_Sk.

| Analysis | Recombinant hyaluronidase |
|---|---|
| Molecular Aggregates (UV250-350 nm analysis) | No aggregate |
| Solution pH in (1x PBS) | ~7.5 |

Hyaluronidase according to the present invention has those activity and high purity features that are necessary for its use in industrial, diagnostic and therapeutic applications. Furthermore, compared to other hyaluronidases known so far, the hyaluronidase produced according to the present invention has proved to be an enzyme that is able to hydrolyse the hyaluronic acid present in the interstitial matrix, increasing the permeability of the connective tissue and favoring the diffusion and dispersion of the drug, locally administered subcutaneously, into the surrounding tissues with extreme stability without the possibility of being digested by proteolytic enzymes present in the connective tissue, which could easily degrade it, once injected, thus inhibiting its action (FIG. 24).

In this invention, thanks to the provision of an in vitro experimental model using the turbidimetric method, what had already emerged from previous clinical studies was confirmed, that is, the enzymatic activity of bovine hyaluronidase (bovine PH20) is inhibited by human and/or animal blood, but it was however found that human and/or animal blood does not inhibit hyaluronidase from recombinant S. koganeiensis (FIG. 25).

Therefore, from the studies presented here it was found that the recombinant hyaluronidase of the invention (produced according to the method above or from S. koganeiensis) has a high hyaluronidase activity, has a high stability to proteolytic enzymes and is able to perform with its maximum bioavailability the total activity in the bloodstream without possibility of bacterial and viral infections. Therefore, it may find use, alone or in combination with other active principles, in the preparation of pharmaceutical or veterinary compositions destined to the treatment of pathologies where it is necessary or advantageous to degrade the hyaluronic acid present in the organ or tissue affected by the pathology.

Thanks to its high stability in aqueous solution, the hyaluronidase of the invention can also be formulated in the form of water based compositions such as solutions, hydrophilic creams, hydrogels, as well as in the form of lipophilic products such as ointments or oily creams. In one aspect, the present invention relates to a polynucleotide comprising the nucleotide sequence shown in SEQ. ID. No. 17 which encodes the bacterial hyaluronidase from *Streptomyces koganeiensis* ATCC 31394 comprising the amino acid sequence shown in SEQ. ID. No. 21.

In another embodiment, the present invention relates to a genetically engineered recombinant vector comprising said polynucleotide comprising the nucleotide sequence shown in SEQ. ID. No. 17.

Preferably, said vector is a plasmid.

In another embodiment, the present invention provides a host cell comprising said vector.

In another aspect, the present invention relates to a composition suitable for pharmaceutical or cosmetic use comprising the hyaluronidase from *Streptomyces koganeiensis* ATCC 31394 in a purified form and comprising the amino acid sequence shown in SEQ. ID. No. 21, obtainable from the above method or by extraction from *Streptomyces koganeiensis*.

In a further embodiment, the present invention relates to the hyaluronidase from *Streptomyces koganeiensis* ATCC 31394 in a purified form and comprising the amino acid sequence shown in SEQ. ID. No. 21, obtainable by the above method or by extraction from *Streptomyces koganeiensis*, for use in the treatment and/or prevention of a disease or disorder, optionally in combination with at least another active principle.

The hyaluronidase of the present invention can be applied both in the medical field and in the veterinary field. Preferably, hyaluronidase according to the invention is for use in the treatment and/or prevention of at least one among oedemas, inflammatory conditions, chilblains, solid tumors, IgE-mediated allergies, diseases of the oral cavity, spontaneous vitreous haemorrhages, arteriosclerosis, blood pressure disorders, cardio-cerebro vascular disorders such as brain arterial stenosis or stroke or bovine mastitis.

As regards the human use, without intending to be limited to it, the hyaluronidase of the invention can be used for the preparation of pharmaceutical compositions intended for the treatment of edemas, in particular edemas on a traumatic basis, or inflammatory conditions such as the haemorrhoid syndrome; moreover, it can be used for the preparation of compositions intended for the treatment of chilblains. The hyaluronidase of the invention can also be used in combination with other drugs of which it is necessary or advantageous to increase the bioavailability.

For example, for the treatment of oedemas on a traumatic basis, combinations of the hyaluronidase according to the invention with anticoagulant and/or fibrinolytic agents are particularly advantageous. Such combinations may also possibly contain one or more steroidal or non-steroidal anti-inflammatory agents. Moreover, these compositions may be advantageously associated with sulphated hyaluronic acid, which is known to have, in addition to anti-inflammatory properties, also antithrombotic and anti-coagulant properties. Associations of the hyaluronidase according to the invention with other active principles are advantageous also in the case of injectable preparations containing active principles with a particularly high molecular weight, for example monoclonal antibodies, cytokines, enzymes, DNA and drug carrier nanoparticles which are usually administered intravenously; this hyaluronidase allows the administration thereo subcutaneously, according to the so-called EASI (Enzymatically-Augmented Subcutaneous Infusion) procedure, that is used especially for the replacement of fluids in terminal patients, so as to restrict or avoid the nursing care. Hyaluronidase according to the invention can also be used for the preparation of pharmaceutical compositions intended for the treatment of resistant solid tumors. In fact, by degrading the hyaluronic acid, it lowers the pressure of the interstitial fluids into the tumor mass, thus increasing the blood flow to the tumor and thus increasing the efficiency of transport of therapeutic agents towards their target which slow down or inhibit the tumor growth in a more effective way. For the same reason, it also increases the effectiveness of anticancer active ingredients possibly associated thereto. Therefore, a further aspect of the invention relates to pharmaceutical compositions containing hyaluronidase in combination with one or more anticancer active ingredients, such as *Vinca* alkaloids (vinblastine, vincristine, vinorelbine) and taxanes (Paclitaxel).

A further therapeutic use of hyaluronidase according to the invention relates to the use in the treatment of IgE-mediated allergic forms with EPD (Enzyme Potentiated Desensitization), which consists in the administration of very low doses of allergens to desensitize individuals sensitive to them. By associating hyaluronidase with an allergen it is possible to increase the effectiveness of the treatment, since the allergen more easily reaches the site of action. Therefore, a further object of the invention consists in pharmaceutical compositions containing hyaluronidase in association with one or more allergens that induce IgE-mediated allergic reactions. Hyaluronidase is also used as a factor of diffusion of drugs for dental use in the treatment of oral diseases, such as local anaesthetics and antibiotics; therefore, according to a further aspect, the invention relates to pharmaceutical compositions containing hyaluronidase according to the invention in association with one or more local anesthetics or antibiotics.

In ophthalmology, hyaluronidase allows to greatly accelerate the treatment of spontaneous vitreous hemorrhages and can be used, alone or in combination with other active ingredients, in the preparation of pharmaceutical forms for ophthalmic use such as solutions, suspensions, gels, creams and ointments, intended for the treatment of such hemorrhages.

Previous studies have shown the efficacy of hyaluronidase in the treatment of cardiovascular diseases such as atherosclerosis [2] and in the management of blood pressure [3]. Moreover, thanks to the ability of hyaluronidase, produced according to this invention, to perform the total activity in the bloodstream without being inhibited, it can be used also for cardio-cerebro-vascular therapies.

On the other hand, as regards the veterinary use, a disease that can be effectively treated with the hyaluronidase of the invention is bovine mastitis; in this case, the hyaluronidase can be administered in combination with antibiotics, such as Penicillin G, I-IV generation cephalosporins and enhanced amminopenicilline. Thanks to its stability in aqueous solution, the hyaluronidase according to the invention can be formulated in aqueous-based products; the choice between an aqueous-based formulation and an oil-based formulation can be made by a man skilled in the art on the basis of common knowledge in the field of pharmaceutical technology, based on the other ingredients in the composition.

In one embodiment, the present invention relates to the non-therapeutic use of hyaluronidase in a purified form and comprising the amino acid sequence shown in SEQ. ID. No. 21 or obtainable from *Streptomyces koganeiensis* ATCC 31394 or by the method above for cosmetic applications and/or for improving the aesthetic appearance.

Hyaluronidase is also used in cosmetics for the treatment of granulomatus reactions or incorrect, undesired collocations of hyaluronic acid, caused by fillers.

Moreover, today, after studies and investigations, an injectable product based on hyaluronidase has been developed which can dramatically improve the fibrosis condition present in cellulite. Hyaluronidase, by segmenting the fibrotic component of cellulite, makes it softer with reduction of the orange peel effect, thus giving a more natural and pleasing appearance to the portion of skin treated. In this case, hyaluronidase is appropriate for all those people who suffer from cellulite or with little presence of fat mass. And to date, it is the only real therapy capable of opposing cellulite with satisfactory results in aesthetic and/or therapeutic terms.

The present invention includes hyaluronidase as described above for the treatment and/or prevention of cellulite for both therapeutic and non-therapeutic purposes. Finally, the hyaluronidase according to the invention can be used as a reagent in biochemical assays for the qualitative/quantitative determination of hyaluronic acid.

An embodiment of the present invention is described below in an example given for illustrative and not limiting purpose.

EXAMPLE 1: BACTERIAL STRAIN AND CULTURE CONDITIONS

The *S. koganeiensis* strain was obtained from American Type Culture Collection (ATCC 31394). The extracellular material was obtained from cells of the bacterium as previously described [9]. Briefly, a colony of the microorganism was transferred from ISP Medium 2 agar plates and grown in 500 ml of culture medium [(20 g/l of yeast extract (Organotechnie) and 5 g/l of soya peptone (Solabia), at pH 6.9)] at 30° C., STIRRING at 150 rpm for about 16 hours. After growth, the culture was used to inoculate a 20 liter fermenter (Biostat U, B. BRAUN) containing 10 liters of special soil [(10 g/l of yeast extract (Organotechnie), 5 g/l peptone soybean (Solabia), g/l of malt extract (Constantine), 3 g/l of dextrin type I (Sigma), 0.2 g/l of antifoam (Sigma)]. Before carrying out the inoculation, the pH was brought to 7.0 with NaOH; during the fermentation, the pH was monitored but not controlled, and the temperature was maintained at ° C. throughout the fermentation, while stirring was maintained at 300 rpm, with aeration of 1.6 VVM (liters of air/liter of fermentation medium/min). The fermentation had a duration of 48 h, time which coincided with the maximum production of hyaluronidase enzyme activity in the culture supernatant. The culture was sampled daily to assess the growth, viability and concentration of the hyaluronidase produced in the culture supernatant by determination of the enzymatic activity by the Dorfman's method [10]. At various steps, the cell density was determined by counting under a microscope, measuring the optical density at 600 nm and by counting the colonies on plates of ISP Medium 2 agar (Difco).

Cellular fractions are collected every 3-4 hours, where a part is used to assess the levels of RNA and DNA (FIG. 1) by standard methods, using the spectrophotometer T60 UV-Vis (PG Instruments), the other part of the fraction is stored at −80° C. in RNAprotect Bacteria Reagent (Qiagen). At the end of the fermentation, the culture was centrifuged at 5000 rpm for 30 minutes at 4° C. (Sorvall Evolution RC) and filtered with 0.2 μm tangential flow polyethersulfone filters so as to eliminate the biomass of *Streptomyces koganeiensis* (which was in the form of rounded hyphal aggregates of 1-4 mm diameter) and to obtain a clarified supernatant containing hyaluronidase. Subsequently, the supernatant was concentrated and dialyzed by tangential filtration as previously described [9].

EXAMPLE 2: ISOLATION IN FPLC OF AUTOLOGOUS HYALURONIDASE

The concentrated and dialyzed supernatant was purified and enriched with hyaluronidase alone as previously described [9]. Briefly, the isolation and characterization of the protein occurred using a proteomic approach supported by a process based on the use of a combination of ion-exchange chromatography columns (GE Healthcare), in sequence: CM-Sepharose FF, HiTrap Q XL and HiTrap SP FF, Resource Q. The individual fractions eluted from the chromatographic columns were tested for their highest hyaluronidase activity using an enzymatic dosage and analyzed in parallel for their protein content by SDS-PAGE.

Determination of the hyaluronidase activity. The hyaluronidase activity was measured with the modified Dorfman's method [10]. Briefly, the product obtained by the chromatographic process was diluted in 0.03M phosphate buffer, 0.82% NaCl, pH 6.3 and 1 ml of the thus obtained solution was mixed with 1 ml substrate buffer (0.03M phosphate buffer, NaCl 10.82%, pH 6.3) containing 0.5 mg hyaluronic acid. The enzymatic digestion was carried out at 37° C. for 30 minutes and at the end of the incubation process, turbidity was generated by adding a 4 ml horse serum-based acidic solution (SIGMA). The optical density at 640 nm was measured exactly 30 minutes after the addition of the horse serum acidic solution. A standard of hyaluronidase from mammal testicles (EDQM, FIP Hyaluronidase, H1115000) containing 328 IU/mg was used to construct a standard curve and the activity (in units) of the samples was calculated using this curve. Electrophoresis and analysis in SDS-PAGE.

The electrophoretic assays on polyacrylamide gel in the presence of sodium dodecyl sulfate (SDS-PAGE) were carried out using Laemmli's method [11] on 12% polyacrylamide gel, using a Mini-PROTEAN 3 (BIO-RAD) according to the manufacturer's instructions. The molecular weight of the purified protein was assessed by comparison with standard low molecular weight proteins (BIO-RAD). The polyacrylamide gels suitably stained with Silver Stain Plus (BIO_RAD) or Coomassie (BIO-RAD) after the electrophoretic run, were acquired by a laboratory image capturing device ImageQuant 300 TL (GE Healthcare), while (quantitative and qualitative) assays were performed using the image analysis software ImageQuant TL (GE Healthcare).

EXAMPLE 3: N-TERMINAL SEQUENCING OF INTERNAL PROTEIN FRAGMENTS

The N-terminal amino acid sequencing was carried out according to Edman's degradation method using an automated protein sequencer in pulsed liquid phase (ABI-Perkin Elmer Mod. 477A). The searches for homology were performed using the BLAST software (National Center for Biotechnology Information at the National Library of Medicine (Bethesda, Md.) [28], the search server Broad Institute (http://www.broadinstitute.org/) and the ClustalW software (http://www.ebi.ac.uk/clustalw/). The signalP (http://www.cbs.dtu.dk/services/SignalP-2.0/) and Interproscan (http://www.ebi.ac.uk/Tools/pfa/iprscan/) were respectively used to conduct analysis of the signal peptide cleavage site and for the analysis of the protein domain.

The information concerning the primary structure of the isolated hyaluronidase were determined by sequencing the N-terminal portion of the entire protein and fragments obtained after digestion with trypsin, chymotrypsin, Glu-C and separation of the fragments produced by HPLC. From the N-terminal sequencing carried out, the N-terminal amino acid sequence and the amino acid sequence of internal fragments were identified, and they are shown hereafter in a sequence:

```
                            (SEQ ID NO: 1)
AGENGATTTFDGPVA (SEQ ID NO: 2)
RFSADTTIEAAFIKTTSETIHAATIYK (SEQ ID NO: 3)
GYADGSDKDAAALSLDLR (SEQ ID NO: 4)
AQVHIVQR (SEQ ID NO: 5)
IGNAATVPTSVDSSGGG
```

A search was performed in the database with the sequences identified and the homology of hyaluronidase from *S. koganeiensis* ATCC 31394 with a predicted protein (protein_id ZP_06911952.1) of *Streptomyces pristinaespiralis* ATCC 25486 was identified. On the basis of the N-terminal sequence of the peptides obtained from the isolated protein according to this invention, it was possible to synthesize the corresponding oligonucleotides, that served to isolate the gene encoding hyaluronidase from *S. koganeiensis* genome.

EXAMPLE 4: IDENTIFICATION OF THE NOVEL HYALURONIDASE GENE

The gene encoding the hyaluronidase was isolated from the DNA from bacterial cells of *Streptomyces koganeiensis*. Briefly, the pellets of the bacterial cells from the fermentation in the period of exponential production of hyaluronidase (FIG. 1), are treated for the extraction and purification of genomic DNA using DNeasy Tissue Kit (Qiagen), while the RNA was extracted with RNeasy Mini Kit (Qiagen). A cDNA library was obtained starting from total RNA using MICROBExpress kit and Poly (A) Tailing kit (Applied Biosystems) to isolate mRNA (messenger RNA) from total RNA and the SMART RACE cDNA Amplification Kit (Clontech) according to the manufacturer's instructions. The products thus obtained are analyzed quantitatively using a spectrophotometer T60 UV-Vis (PG Instruments) and qualitatively by electrophoresis in agarose gels [12].

As described in the previous paragraph, the identical amino acid regions between *S. koganeiensis* and *S. pristinaespiralis* were identified; the following oligonucleotides were designed on nucleotide regions encoding these identical amino acid residues by the use of online tools and a generic bacterial usage codon: MesFor2 (5'-GGA-GAACGGGGCGACGACGACGTTCG-3'(SEQ ID NO: 6)) corresponding to the peptide present in the N-terminal area (ENGATTTF), the antisense MesRev2 (5'-GTCGGCAC-CGTCGCCGCGTTCCCGAT-3' (SEQ ID NO: 7)) corresponding to the peptide present in the C-terminal area (IGNAATVP).

With these two oligonucleotides, and only on genomic DNA as template, several PCR reactions were performed with KOD polymerase (Toyobo), experimenting different conditions of temperature and using or not DMSO at 4%. At the end of the various processing steps, a specific PCR product was obtained (conditions: initial denaturation 95° C. 5 min, 96° C. 40 sec, 55° C., 30 sec annealing, 72° C. 1 min extension, for 40 cycles and 72° C. 10 min), in fact, the PCR only amplifies a specific band of approximately 550 bp. The contiguous of the two sequencing processes of the fragment gave the sequence (SEQ ID NO: 8) shown in FIG. 2. The PCR products were analyzed by electrophoresis in agarose gel. Given the homology between the nucleotide sequences of *S. koganeiensis* and *S. pristinaespiralis*, attention was paid to the non-coding regions flanking the gene being analyzed.

From the online source http://www.broadinstitute.org/annotation/genome/streptomyces_group/GenomeDescriptions.html, the flanking regions of the *S. pristinaespiralis* gene were identified, on which two oligonucleotides were designed (MesExrF: 5'-cgggagaagggtgaacgc-3'(SEQ ID NO:9) and MesExtR: 5'-ctccgcgaccagttcttcg-3'(SEQ ID NO: 10)) to be used in PCR on the genomic DNA template of *S. koganeiensis*. The PCR conditions were defined from the previous step, maintaining a higher denaturation temperature (96° C.) due to the high GC content of the bacterial genomes.

Given the non-specific results, it was decided to try to use these oligonucleotides in combination with MesFor2 (SEQ ID NO: 6) and MesRev2 (SEQ ID NO: 7) used previously and which gave the expected PCR product. It was found that only the amplification with the oligo MesFor2 and MesExtR gave a clear product of the expected size; by sequencing it with the two primers used in the amplification, the region 3' of the gene being analyzed was identified. The inverse PCR technique (IPCR) was developed and performed to identify the nucleotide regions upstream of the gene sequence identified to date (FIG. 3). The IPCR method was performed by the following processing steps:

a) Digestion of the genomic DNA with restriction enzymes. Three different reactions of enzymatic digestion were set up with the enzymes KpnI NARI, and NotI, of approximately 100 ng of genomic DNA of S. koganeiensis.

b) Ligation of the digested DNA.

c) Amplification by PCR using the ligation reactions as template, with oligonucleotides that anneal within the region known to date encoding the hyaluronidase of S. koganeiensis.

The oligonucleotides used are the following:

```
MesINTf
(5'-GGCATCTACGTCACGGCGACGAAC-3' (SEQ ID NO: 11))
and the antisense MesINTr
(5'-CGTACCCGCGGTGGGTGATCTTCAG-3' (SEQ ID NO: 12)).
```

The preparations digested with KpnI and Nari gave PCR products, respectively, of about 700 and 1400 bp, which once sequenced provided accurate information on the region 5' flanking the gene of hyaluronidase of S. koganeiensis. With this step, the identification of the nucleotide sequence of interest (SEQ ID NO: 13), shown in (FIG. 4) is completed.

A pair of primers designed on the non-coding sequences (forward: 5'-accattcggagttgatcgttg-3'(SEQ ID NO: 14) Reverse: 5'-gtcaactgcactgttctctcc-3' (SEQ ID NO: 15)) and flanking the entire gene encoding the hyaluronidase are used for the amplification of the entire gene. The PCR product obtained whose sequence obtained after sequencing (SEQ ID NO: 16) is shown in (FIG. 5), is cleaved from the gel after electrophoresis run, purified using the Wizard SV Gel and PCR Clean-Up System (Promega) and cloned directly into the vector pCR®-BluntII-TOPO® (Invitrogen) in E. coli cells. Subsequently, the clones which were found to be positive (pCR-BluntII-TOPO[sk_HYAL]) at PCR for the presence of the plasmid containing the hyaluronidase gene were analyzed by sequencing.

Analysis of the deduced protein sequence.

BLAST software was used for conducting homology searches on the GenBank database. While the software ExPASy Translate Tool, available on the web, was used to allow the translation in silico of the nucleotide sequence of the isolated gene encoding the hyaluronidase from S. koganeiensis in the protein sequence. Finally, the conserved domain for the hyaluronidase activity was verified by the InterProScan software available on the website (http://www.ebi.ac.uk/Tools/InterProScan/) (FIG. 7 (a)). From the results obtained it was observed that the entire length of the gene encoding the hyaluronidase from S. koganeiensis was of 744 bp (SEQ ID NO: 17) and the length of the peptide sequence was estimated to be 247 amino acids (SEQ ID NO: 18). The gene contains a putative domain (SEQ ID NO: 19) of proteins belonging to hyaluronidase family (Hyaluronidase_1), as evidenced by the search for homologies on the Pfam database. Moreover, the analysis of the sequence (SEQ ID NO: 18) using the specific tool http://www.cbs.dtu.dk/services/SignalP-1.1/indicated the presence of a signal sequence (signal peptide) of 30 amino acids (amino acids 1 to 30 (SEQ ID NO: 47), with the cleavage site between amino acid 30 and 31). The mature protein (SEQ ID NO: 21) then is 217 amino acids long (corresponding to the nucleotide sequence 651 bp (SEQ ID NO: 22)) and its molecular weight is predicted (using the tools available on the site http://web.expasy.org/compute_pi/) is 21679.96 Da. Finally, BLAST analysis for sequence homologies shows homology between the amino acid sequence determined for the hyaluronidase S. koganeiensis ATCC 31394 (SEQ ID NO: 18) and the amino acid sequences reported in the database on the web: homology with the amino acid sequence of the protein Hyaluronoglucosaminidase (predicted from the analysis of the open reading frames starting from the genomic locus described on the web with code YP_006266806.1) from Actinoplanes sp. showing 68% identity/78% similarity, homology with the amino acid sequence of the predicted protein ZP_06911952.1 (predicted by the analysis of the open reading frames starting from the genomic locus described on the web code ZP_06911952.1) of Streptomyces pristinaespiralis ATCC 25486 with 66% identity/77% similarity (SEQ ID NO: 23 and SEQ ID NO: 48) and homology with the amino acid sequence of the hypothetical protein STSU_30255 (predicted from the analysis of the open reading frames starting from the genomic locus described on the web with code ZP_10072726.1) of Streptomyces tsukubaensis NRRL18488 (SEQ ID NO: 24 and SEQ ID NO: 49) with 66% identity/80% similarity (FIG. 6 a,b). Given the significant similarity of the functional domain (SEQ ID NO: 25 and SEQ ID NO: 50, SEQ ID NO: 26 and SEQ ID NO: 51) observed with hyaluronidase described by this invention (SEQ ID NO: 19), the entire CDS nucleotide sequence encoding these proteins, which are defined on the web with the terminology of "hypothetical or "predicted", was isolated from the original genomic locus and characterized, permitting to identify them, for the first time, in this invention as hyaluronidase (FIG. 7 (b)). However, none of these analyses found the entire exact nucleotide sequence and the amino acid sequence of the hyaluronidase isolated according to the patent reported in the literature. A sequence homology was present between a region of the sequence (SEQ ID NO: 27 and SEQ ID NO: 52) of hyaluronidase from S. koganeiensis according to the invention and one of the modules present in the amino acid domain of murine Cd44 that binds hyaluronic acid (FIG. 7 (a)).

EXAMPLE 5: CLONING OF GENE ENCODING HYALURONIDASE IN PHT43 (+)

The cDNA encoding the hyaluronidase from S. koganeiensis (SEQ ID NO: 41) was amplified by PCR starting from the plasmid pCR-BluntII-TOPO[sk_HYAL] extracted and purified from cells of E. coli with DNA Purification System Wizard Plus SV Minipreps and using the following primers: sense (5'-gtaGGATCCGCCGGGGAGAACG-GCGCGACGACGA-3' SEQ ID NO: 28); antisense (5'-gacTCTAGATCACGCCGGTGCGATCGTCGTGACC-3' SEQ ID NO: 29). The PCR cycles performed for the amplification were: initial denaturation 96° C. for 5 minutes;

30 cycles of annealing 55° C. for 30 seconds, extension at 72° C. for 1 minute, and following denaturation 96° C. for 40 seconds. The Taq DNA polymerase used for the amplification was DyNAzyme II DNA Polymerase (Finnzymes) (FIG. 8). The amplified product (672 bp) was purified by the Kit Wizard SV Gel and PCR Clean-Up System (Promega), digested with BamHI (BioLabs) and XbaI (BioLabs), and ligated using T4 ligase (Ambion) with the vector pHT43 (+) previously digested with BamHI and XbaI (FIG. 8). Once the ligase took place, the vector was transformed inside *E. coli* strain DH5a cells (Invitrogen code 12297-016) by chemical processing. The cells after transformation are plated in LB agar containing ampicillin (50 µg/ml) and incubated at 37° C. for 16 h. The colonies obtained were analyzed to verify the correct ligase occurred between the hyaluronidase gene fragment and the vector by PCR (initial denaturation at 94° C. for minutes, for 30 cycles: annealing at 55° C. for 30 seconds, extension at 72° C. for 60 seconds, and following denaturation at 94° C. for 1 minute), thanks to the aid of vector-specific primers (Forward: 5'-TGTGGAAT-TGTGAGCGGATA-3' (SEQ ID NO:30), Reverse: 5'-TTTCAACCATTTGTTCCAGGT-3'(SEQ ID NO:31)). The PCR product obtained (927 bp) together with the products obtained by digestion of the vector pHTsk_HYAL [vector with insert] (FIG. 10) with restriction enzymes (BamHI, XbaI), was analyzed by electrophoresis in 1% agarose gel (FIG. 9), using the reference standards for the molecular weight (ΦX174 DNA and λDNA/HindIII of Fermentas). For the analysis of the correct frame of the gene encoding the hyaluronidase after being ligated with the vector, the sequence of the PCR product is sequenced. The nucleotide sequence obtained (SEQ ID NO: 38) after sequencing (FIG. 13,*a*) is analyzed using bioinformatics tools such as ClustalW, Traslate (ExPASy) and Chromas life.

EXAMPLE 6: CLONING OF THE GENE ENCODING THE HYALURONIDASE IN PET22B (+)

The cDNA encoding the hyaluronidase from *S. koganeiensis* (SEQ ID NO: 41) was amplified by PCR starting from the plasmid pCR-BluntII-TOPO[sk_HYAL] extracted and purified from cells of *E. coli* with DNA Purification System Wizard Plus SV Minipreps and using the following primers: sense (5'-tggCCATGGCCGGGGAGAACG-GCGCGACGACGA-3'(SEQ ID NO: 32)); antisense (5'-ctcGAATTCtcaCGCCGGTGCGATCGTCGTGACC-3' (SEQ ID NO: 33)). PCR cycles performed for the amplification were: initial denaturation at 96° C. for 5 minutes; 30 cycles of annealing at 55° C. for 30 seconds, extension at 72° C. for 1 minute, and following denaturation at 96° C. for 40 seconds. The Taq DNA polymerase used for the amplification was DyNAzyme II DNA Polymerase (Finnzymes) (FIG. 8). The amplified product (671 bp) was purified by the Kit Wizard SV Gel and PCR Clean-Up System (Promega), digested with NcoI (BioLabs) and EcoRI (BioLabs), and ligated using T4 ligase (Ambion) with the vector pET22b (+) previously digested with NcoI and EcoRI (FIG. 8). Once the ligase took place, the vector was transformed into *E. coli* strain DH5a cells (Invitrogen code 12297-016) by chemical processing. The cells after transformation are plated in LB agar containing ampicillin (50 µg/ml) and incubated at 37° C. for 16 h. The colonies obtained were analyzed to verify the correct ligase occurred between the hyaluronidase gene fragment and the vector by PCR (initial denaturation at 94° C. for 5 minutes, for 30 cycles: annealing at 55° C. for 30 seconds, extension at 72° C. for 60 seconds, and following denaturation 94° C. for 1 minute), thanks to the aid of vector-specific primers (T7-promoter: 5'-TAATACGACTCACTATAGGG-3'(SEQ ID NO: 34), T7-terminator: 5'-GCTAGTTATTGCTCAGCGG-3'(SEQ ID NO: 35)). PCR product obtained (940 bp) together with the products obtained by digestion of the vector pHyal_sk [vector with insert] (FIG. 11) with restriction enzymes (NcoI, EcoRI), was analyzed by electrophoresis in 1% agarose gel (FIG. 9), using the reference standards for the molecular weight (ΦX174 DNA and λDNA/HindIII of Fermentas). For the analysis of the correct frame of the gene encoding the hyaluronidase after being ligated with the vector, the sequence of the PCR product is sequenced. The nucleotide sequence obtained (SEQ ID NO: 39) after sequencing (FIG. 13,*b*) is analyzed using bioinformatics tools such as ClustalW, Traslate (ExPASy) and Chromas life.

EXAMPLE 7: CLONING OF THE GENE ENCODING THE HYALURONIDASE IN PET21B+

The cDNA encoding the hyaluronidase from *S. koganeiensis* (SEQ ID NO: 41) was amplified by PCR starting from the plasmid pCR-BluntII-TOPO[sk_HYAL] extracted and purified from cells of *E. coli* with DNA Purification System Wizard Plus SV Minipreps and using the following primers: sense (5'-ataCATATGGCCGGGGAGAACG-GCGCGACGACGA-3'(SEQ ID NO:36)); antisense (5'-ctc-GAATTCtcaCGCCGGTGCGATCGTCGTGACC-3'(SEQ ID NO: 37)). PCR cycles performed for the amplification were: initial denaturation at 96° C. for 5 minutes; 30 cycles of annealing at 55° C. for 30 seconds, extension at 72° C. for 1 minute, and following denaturation 96° C. for 40 seconds. The Taq DNA polymerase used for the amplification was DyNAzyme™ II DNA Polymerase (FINNZYME) (FIG. 8). The amplified product (672 bp) was purified by the Kit Wizard SV Gel and PCR Clean-Up System (Promega), digested with NdeI (BioLabs) and EcoRI (BioLabs), and ligated using T4 ligase (Ambion) with the vector pET21b (+) (Novagen) previously digested with NdeI and EcoRI (FIG. 8). Once the ligase took place, the vector was transformed inside *E. coli* strain DH5a cells (Invitrogen code 12297-016) by chemical processing. The cells after transformation are plated in LB agar containing ampicillin (50 µg/ml) and incubated at 37° C. for 16 h. The colonies obtained were analyzed to verify the correct ligase occurred between the hyaluronidase gene fragment and the vector by PCR (initial denaturation at 94° C. for 5 minutes, for 30 cycles: annealing at 55° C. for 30 seconds, extension at 72° C. for 60 seconds, and following denaturation at 94° C. for 1 minute), thanks to the aid of vector-specific primers (T7-promoter: 5'-TAATACGACTCACTATAGGG-3'(SEQ ID NO:34), T7-terminator: 5'-GCTAGTTATTGCTCAGCGG-3'(SEQ ID NO:35)). The PCR product obtained (874 bp) together with the products obtained by digestion of the vector pHyal_sk_SL [vector with insert] (FIG. 12) with restriction enzymes (NdeI, EcoRI), was analyzed by electrophoresis in 1% agarose gel (FIG. 9), using the reference standards for the molecular weight (ΦX174 DNA and λDNA/HindIII of Fermentas). For the analysis of the correct frame of the gene encoding the hyaluronidase after being ligated with the vector, the sequence of the PCR product is sequenced. The nucleotide sequence obtained (SEQ ID NO: 40) after sequencing (FIG. 13,c) is analyzed using bioinformatics tools such as ClustalW, Traslate (ExPASy) and Chromas life.

EXAMPLE 8: HOST BACTERIAL STRAINS USED FOR CLONING AND THE EXPRESSION OF THE HYALURONIDASE GENE FROM S. KOGANEIENSIS

*Escherichia coli* strain DH5a (Invitrogen, Genotype: F-φ801acZΔM15 Δ(lacZYA-argF)U169 recA1 endA1 hsdR17(rk−, mk+) phoA supE44 thi-1 gyrA96 recA1 tonA (confers resistance to phage T1) [22], was used as host for the plasmid amplification of the cloning system. This strain is provided by Invitrogen (One Shot Max Efficiency DH5α-T1R chemically competent *E. coli*, 12297-016). The cells were thawed and cultured in solid medium LB agar (10 g/l peptone from casein, 5 g/l yeast extract, 10 g/l NaCl, 15 g/l bacteriological agar) containing 10 mM MgSO4 and grown for 18 h at 37° C. From the resulting culture, a single colony is taken and grown in TYM broth (tryptone 20 g/l, Yeast Extract 5 g/l, 20 ml 5M NaCl, 1 mM MgSO4) at ° C. From the culture, the resulting cells are chemically treated to obtain chemically competent cells. The cells obtained are portioned and stored at −80° C. in an appropriate storage buffer containing 15% glycerol. The transformations are carried out on this stock of aliquots.

*B. subtilis* WB800N (Genotype: nprE aprE epr bpr mpr:: ble nprB::bsr.vpr wprA::hyg cm::neo; NeoR [23]), provided by MOBITEC, is a gram-positive bacterial strain characterized by a deficit of eight proteases, as a result it is a bacterial strain that is used for the production of secreted heterologous proteins. The neomycin resistance gene was also inserted in this gene, taking the nomenclature of WB800N. The cells of this bacterial strain after an appropriate production were made competent, portioned and stored at −80° C. in an appropriate storage buffer containing 15% glycerol. The transformations are carried out on this stock of aliquots.

*Escherichia coli* strain MG1655 (ATCC number: 12297-016, Genotype: F-lambda-[24,25]), was used as a host in the expression system of the hyaluronidase gene from *S. koganeiensis*. The bacterial strain is provided by the American Type Culture Collection (ATCC). The freeze-dried cells were first cultured in few ml of liquid medium and then in solid medium LB agar (10 g/l peptone from casein, 5 g/l yeast extract, 10 g/l NaCl) containing 10 mM MgSO4 and grown for 18 h at 37° C. From the resulting culture, a single colony is taken and grown in TYM broth at 37° C. From the culture, the resulting cells are chemically treated to obtain chemically competent cells. The cells obtained are portioned and stored at −80° C. in an appropriate storage buffer containing 15% glycerol. The transformations are carried out on this stock of aliquots.

*Escherichia coli* strain BL21 (DE3) (*E. coli* BF-dcm ompT HSDS (rB−mB−) gal λ (DE3) [26,27]), was used as host for the expression system of the gene encoding the hyaluronidase from *S. koganeiensis*. The bacterial strain is provided by Novagen with code 69450-3. The cells were first cultured in few ml of liquid medium and then in solid medium LB agar (10 g/l peptone from casein, 5 g/l yeast extract, 10 g/l NaCl) containing 10 mM MgSO4 and grown for 18 h at 37° C. From the resulting culture, a single colony is taken and grown in TYM broth at 37° C. From the culture, the resulting cells are chemically treated to obtain chemically competent cells. The cells obtained are portioned and stored at −80° C. in an appropriate storage buffer containing 15% glycerol. The transformations are carried out on this stock of aliquots.

EXAMPLE 9: TRANSFORMATION OF PLASMIDS PHTSK_HYAL, PHYAL_SK AND PHYAL_SK_SL IN EXPRESSION CELLS

DH5a cells respectively containing the vectors pHTsk_HYAL, pHyal_sk and pHyal_sk_SL were put in culture in about 6 ml of LB broth with ampicillin (50 µg/ml) and grown for 16-18 h. The respective cultures after the growth of the engineered cells are centrifuged at approximately 5000 g for 10 minutes. The respective plasmids pHTsk_HYAL, pHyal_sk and pHyal_sk_SL were extracted and purified from the pellet obtained using the kit Wizard Plus SV minipreps DNA Purification System (Promega). The purified vectors pHTsk_HYAL, pHyal_sk and pHyal_sk_SL are separately transformed in expression cells. The first vector is transformed into cells, made competent, of *Bacillus subtilis* (WB800N-MOBITEC) while the other two vectors are transformed into cells, made competent, of *E. coli*, strain BL21 (DE3) and/or MG1655. All transformations were carried out by chemical processing [13]. The cells of *B. subtilis* and *E. coli* after transformation, respectively, are plated in LB agar containing chloramphenicol (10 µM) plus neomycin (10 µM), and in LB agar containing ampicillin (50 µg/ml) to develop resistance to the antibiotic, and incubated at 37° C. for 16 h. The colonies obtained after the respective transformations were analyzed to verify the presence of the correct plasmid within the expression cells, by PCR (initial denaturation at 94° C. for 5 minutes, for 30 cycles: annealing at 55° C. for 30 seconds, extension at 72° C. for 60 seconds and following denaturation at 94° C. for 1 minute), thanks to the aid of species-specific primers (Forward: 5'-TGTGGAATTGTGAGCGGATA-3'(SEQ ID NO: 30), Reverse: 5' TTTCAACCATTTGTTCCAGGT-3' (SEQ ID NO: 31)) for the analysis of the successful transformation into *B. subtilis* and to verify the successful transformation in *E. coli*. (T7-promoter: 5'-TAATACGACTCACTATAGGG-3'(SEQ ID NO:34), T7-terminator: 5'-GCTAGTTATTGCTCAGCGG-3' (SEQ ID NO: 35)) The PCR products obtained for the cells transformed with pHTsk_HYAL (927 bp), pHyal_sk (940 bp) and pHyal_sk_SL (874 bp) were analyzed by electrophoresis in 1% agarose gel using reference standards for the molecular weight (ΦX174 DNA and λDNA/HindIII by Fermentas). For the analysis of the correct frame of the gene encoding the hyaluronidase after being bound to the vector, the sequence of the PCR products is sequenced. The nucleotide sequence obtained after sequencing is analyzed using bioinformatics tools such as Vector NTI Advance 9 (Invitrogen), ClustalW, Traslate (ExPASy) and Chromas life. (FIG. 13 a,b,c).

EXAMPLE 10: ASSESSMENT OF THE EXPRESSION LEVEL OF THE RECOMBINANT HYALURONIDASE

The clones of *B. subtilis* found to be positive for the presence of vectors containing the nucleotide fragment of hyaluronidase found genetically with the frame sequence for correct expression (SEQ ID NO: 41), are tested for the expression level, and then the cells thus engineered are inoculated into flasks containing 500 ml of LB broth with chloramphenicol (10 µM, Sigma) and neomycin (10 µM, Sigma), and incubated at 37° C. at 250 rpm. When the cell growth value reaches OD600 nm 0.8, they are brought with IPTG (Sigma, I6758) to a final concentration of 1 mM. After 12 hours of induction, the bacterial culture is centrifuged at 7500 rpm for 10 minutes and the culture supernatant is collected to evaluate the expression in *B. subtilis*.

Subsequently, the supernatant from the expression tests in *B. subtilis* was concentrated (20 times) and dialyzed in phosphate buffer 1× by ultrafiltration on special polyethersulfone filters with cut-off of 5 kD.

In SDS-PAGE, the expressed recombinant had a molecular weight of about 24 kDa with the maximum expression after induction with 1 mM IPTG at OD600 nm 0.8 after 12 hours at 37° C.

The expression and localization of the expression of hyaluronidase in the cells of *B. subtilis* (SEQ ID NO: 21), in the different clones analyzed, was determined by electrophoresis in SDS-PAGE (12%) after staining with Coomassie Brilliant Blue G-250 (BIO-RAD, 161-0406) and with an appropriate enzyme assay, for example Dorfman's assay.

EXAMPLE 11: ASSESSMENT OF THE EXPRESSION LEVEL OF RECOMBINANT HYALURONIDASE IN *E. COLI*

The clones of *E. coli* found to be positive for the respective presence of vectors containing the nucleotide fragment of hyaluronidase found genetically with the frame sequence (SEQ ID NO: 41) for the correct expression (SEQ ID NO: 21) are tested for the expression level, inoculated into flasks containing 500 ml of LB broth with ampicillin (50 µg/ml, Sigma) and incubated at 37° C. at 250 rpm. When the cell growth value reaches OD600 nm 0.8, they are brought with IPTG (Sigma, I6758) to a final concentration of 1 mM. The bacterial cells are harvested after 3-4 hours of induction, by centrifugation at 7500 rpm for 10 minutes. After centrifugation, the bacterial pellet is collected for the assessment of the expression in engineered cells of *E. coli* and to verify in what portion of the cell the recombinant is produced.

Subsequently, the pellets coming from the *E. coli* cells induced with IPTG were treated with B-PER Bacterial Protein (PIERCE) according to the instructions provided by the supplier, to assess the expression of hyaluronidase in the periplasmic and/or cytoplasmic portion and/or forming inclusion bodies. Both clones of *E. coli* respectively containing the plasmids pHyal_sk and pHyal_sk_SL expressed the recombinant in soluble form in the periplasmic portion:

*E. coli* BL21 (DE3) containing pHyal_sk. In SDS-PAGE, the expressed recombinant has a molecular weight of about 24 kDa, constituting about 40% of the total bacterial proteins after induction at OD600 nm 0.8 with 1 mM IPTG for 3-4 hours at 37° C. However, of the amount of expressed recombinant, only 18% (only 7.2% overall) is present in soluble form in the periplasm, the remaining 82% has inclusion bodies (only 32.8% overall). The periplasmic soluble portion turns out to be present at a maximum concentration of 52 µg/ml culture, with an enzymatic activity equal to about 2100 U/ml culture.

*E. coli* BL21 (DE3) containing pHyal_sk_SL. In SDS-PAGE, the expressed recombinant has a molecular weight of about kDa, constituting about 15% of the total bacterial proteins after induction at OD 600 nm 0.8 with 1 mM IPTG for 3-4 hours at 37° C. Moreover, all the expressed protein is present in soluble form in the periplasm. The periplasmic soluble portion turned out to be present at a concentration of about 125 µg/ml culture, with an enzymatic activity greater than 5000 U/ml culture.

Both the expression and localization of the expression of hyaluronidase in the cells of *E. coli* in the different clones analyzed, was determined by electrophoresis in SDS-PAGE (12%) after staining with Coomassie Brilliant Blue G-250 (BIO-RAD, 161-0406) and with an appropriate enzyme assay, for example Dorfman's assay.

EXAMPLE 12: DEVELOPMENT OF THE MASTER CELL BANK AND WORKING CELL BANK OF RECOMBINANT STRAINS

Master Cell Bank (MCB)

Under sterility, a single colony was taken from the colonies belonging to the producer strain and resuspended in a sterile flask containing 10 ml of liquid medium (LB broth with chloramphenicol (10 µM, Sigma) and neomycin (10 µM, Sigma) as regards the recombinant cells of *B. subtilis* and LB broth with ampicillin (50 µg/ml, Sigma) as regards the recombinant cells of *E. coli*) and incubated at 200 rpm at 37° C. for about 16 hours. After the incubation period and after suitable checks on the sterility of the culture, 10 ml of each culture were respectively transferred in 100 ml of liquid medium (LB broth with chloramphenicol (10 µM, Sigma) and neomycin (10 µM, Sigma) as regards the recombinant cells of *B. subtilis* and LB broth with ampicillin (50 µg/ml, Sigma) as regards the recombinant cells of *E. coli*) and incubated for 5-6 hours at 37° C. at 200 rpm. Again, after the incubation period and after appropriate checks on the sterility of the culture, an amount of sterile glycerol was added cold to each culture until reaching a final concentration of glycerol equal to 15%. The mixture is stirred and 2 ml aliquots are introduced into cryogenic vials (CORNING, 430659) which are immediately placed at −80° C.

The development of the Master Cell Bank was performed under sterile conditions for strains: strain *B. subtilis* (WB800N-MoBitec) containing the plasmid engineered with pHTsk_HYAL (clone 105), strain *E. coli* (DH5a) containing the plasmid engineered with pHTsk_HYAL (clone 105), strain *E. coli* (DH5a) and *E. coli* (BL21 (DE3)) containing the plasmid engineered with pHyal_sk (clone 413), strain *E. coli* (DH5a) and *E. coli* (BL21 (DE3)) containing the plasmid engineered with pHyal_sk_SL (clone 225) and strain E. (DH5a) and *E. coli* (BL21 (DE3)) containing the plasmid engineered with pRH_sk (clone 600).

Working Cell Bank (WCB)

Under sterility, an aliquot was taken from a vial from the Master Cell Bank and tested in solid medium LB broth with chloramphenicol (10 µM, Sigma) and neomycin (10 µM, Sigma) as regards the recombinant cells of *B. subtilis* and LB broth with ampicillin (50 µg/ml, Sigma) or kanamycin (30 µg/ml, SIGMA) as regards the recombinant cells of *E. coli*) and incubated at 200 rpm at 37° C. for about 18 hours. Under sterile hood, a single colony was taken from the colonies belonging to the producer strain and resuspended in a sterile flask containing 10 ml of liquid medium (LB broth with chloramphenicol (10 µM, Sigma) and neomycin (10 µM, Sigma) as regards the recombinant cells of *B. subtilis* and LB broth with ampicillin (50 µg/ml, Sigma) or kanamycin (30 µg/ml, SIGMA) as regards the recombinant cells of *E. coli*) and incubated at 200 rpm at 37° C. for about 16 hours. After the incubation period and after suitable checks on the sterility of the culture, 10 ml of each culture were respectively transferred in 100 ml of liquid medium (LB broth with chloramphenicol (10 µM, Sigma) and neomycin (10 µM, Sigma) as regards the recombinant cells of *B. subtilis* and LB broth with ampicillin (50 µg/ml, Sigma) or kanamycin (30 µg/ml, SIGMA) as regards the recombinant cells of *E. coli*) and incubated for 5-6 hours at 37° C. at 200 rpm. Again, after the incubation period and after appropriate checks on the sterility of the culture, an amount of sterile glycerol was added cold to each culture until reaching a final concentration of glycerol equal to 15%. The mixture is stirred and 2 ml aliquots are introduced into cryogenic vials (CORNING, 430659) which are immediately placed at −80° C.

The development of Working Cell Bank was carried out under maximum sterility and for the strains: strain *B. subtilis* (WB800N-MoBitec) containing the plasmid engineered with pHTsk_HYAL (rhyaluronidase clone 105), *E. coli* (BL21 (DE3)) containing the plasmid engineered with pHyal_sk (hyaluronidase clone 413), strain *E. coli* (BL21 (DE3) containing the plasmid engineered with pHyal_sk_SL (clone rHyal_Sk) and for strain *E. coli* (BL21 (DE3) containing the plasmid engineered with pRH_sk (clone rH_sk).

The following tests were performed both on MCB and on WCB to assess their purity: assessment of the number of copies of the plasmid from the cells of MCB and WCB, analysis of the plasmid by restriction enzymes and separation of the digested fragments by 1% agarose gel, assessment of the conservation of glycerol in cells containing the expression plasmid in the MCB and WCB, evaluation of the stability of the cells containing the expression plasmid in the MCB and WCB, viability of recombinant cells in LB plates, identity of the strains *E. coli*, purity of the culture, Coli phage assay, evaluation of the expression product in SDS-PAGE, sequencing of the region encoding the recombinant protein.

EXAMPLE 13: BATCH FERMENTATIONS OF RECOMBINANT HYALURONIDASE

The ability of clones of *E. coli* BL21 (DE3)—pHyal_sk and BL21 (DE3)-pHyal_sk_SL to produce the recombinant hyaluronidase was evaluated by growth in fermenters by batch culture.

The inoculum is prepared by inoculating a vial (from the working cell bank stored at −80° C.) in 400 ml of fresh LB medium (ratio 1/20 with respect to the fermentation volume) containing 50 µg/ml ampicillin and incubated at 37° C. at 150 rpm for 16-18 hours. The clones from the respective inocula (*E. coli* BL21 (DE3)-pHyal_sk and BL21 (DE3)—pHyal_sk_SL), were separately grown in the fermenter on a minimum culture medium whose composition per liter was given by: 2 g $Na_2HPO_4*2H_2O$, 2 g $KH_2PO_4$, 4 g $K_2HPO_4$, 3.8 g citric acid, 3.3 g $(NH_4)_2SO_4$, 40 ml glycerol, 0.6 ml PPG 2000 antifoam (Fluka Code 81380). The pH was corrected after sterilization at 121° C. to 6.8 with a 25% solution of ammonium hydroxide % (SIGMA), and only adding the following components per liter of medium, sterilized by filtration through 0.2 µm filters: 0.49 g $MgSO_4*7H_2O$, 0.0147 g $CaCl_2$, 1 ml $FeCl2$ (0.2M), 2 ml trace elements (trace elements per liter: 0.96 g citric acid, 0.25 g $CoCl2*6H2O$, 1.5 g $MnCl_2*4H_2O$, 0.15 g $CuCl_2*2H_2O$, 1.5 g $H_3BO_3$, 0.25 g $Na_2MoO_4*2H2O$, 1.3 g $Zn(CH_3COO)_2*2H_2O$), 0.01 g thiamine, 5 g glucose, 3 g yeast extract.

The induction with Isopropyl β-D-1-thiogalactopyranoside (IPTG) occurs 4-6 hours after inoculation and continued for about 16-18 hours. The fermentation parameters developed were as follows: temperature 37° C., agitation 600 rpm, air flow 5-10 liters air per minute and head pressure of about 0.8 bar.

The bacterial cells are harvested after the induction period of about 16 hours by centrifugation at 7500 rpm for 25 minutes. After collection, the bacterial cells are stored at −80° C., ready to be used for the extraction and purification o recombinant hyaluronidase. The recombinant protein expressed by *E. coli*, in the different fermentation parameters, is analyzed by electrophoresis run in SDS-PAGE (12%) after staining with Coomassie Brilliant Blue G-250 (BIO-RAD, 161-0406), while the enzyme activity is analyzed by turbidimetric assay [16]. The cells of *E. coli* BL21 (DE3) transformed with the vector pHyal_sk are induced to express the soluble heterologous protein in the periplasm, in the fermenter with 8 L of medium. In SDS-PAGE, the expressed recombinant had a molecular weight of about 24 kDa and an amount of protein expressed in the cell periplasm of about 0.1-0.15 g/L of culture, the maximum quantity reached after 16 hours of induction with 1 mM IPTG at 37° C.

The cells of *E. coli* BL21 (DE3) transformed with the vector pHyal_sk_SL are induced to express the soluble heterologous protein in the periplasm, in the fermenter with 8 L of medium. The periplasmic soluble portion turned out to be present at a concentration of about 0.35-0.5 g/L culture, with an enzymatic activity greater than 15050-21495 U/ml culture. In SDS-PAGE, the recombinant expressed had a molecular weight of about 24 kDa, constituting about 18% of the total bacterial proteins, after induction with 1 mM IPTG at the sixteenth hour at 37° C.

For both clones, the stability of the plasmid during fermentation was found to be 100% (Table 2). The stability of the plasmid is monitored until the end of the fermentation by screening with the replica plating technique [29] which allows replication of the colonies on plates containing the antibiotic.

EXAMPLE 14: FED-BATCH FERMENTATIONS OF RECOMBINANT HYALURONIDASE

The ability of clones of *E. coli* BL21 (DE3)—pHyal_sk and BL21 (DE3)—pHyal_sk_SL to produce the recombinant hyaluronidase was evaluated by growth in fermenters by fed-batch culture.

The inoculum is prepared by inoculating a vial (from the working cell bank stored at −80° C.) in 500 ml of fresh LB medium (ratio 1/20 with respect to the fermentation volume) containing 50 µg/ml ampicillin and incubated at 37° C. at 150 rpm for 16-18 hours. The clones from the respective inocula (*E. coli* BL21 (DE3)-pHyal_sk and BL21 (DE3)—pHyal_sk_SL), were separately grown in the fermenter on a minimum culture medium whose composition per liter was given by: 2 g $Na_2HPO_4*2H_2O$, 2 g $KH_2PO_4$, 4 g $K_2HPO_4$, 3.8 g citric acid, 3.3 g $(NH4)_2SO_4$, 0.6 ml PPG 2000 antifoam (Fluka Code 81380). The pH was corrected after sterilization at 121° C. to 6.8 with a 25% solution of ammonium hydroxide % (SIGMA), and only after having added the following components per liter of medium, sterilized by filtration through 0.2 µm filters: 0.49 g $MgSO_4*7H_2O$, 0.0147 g $CaCl_2$, 1 ml $FeCl_2$ (0.2M), 2 ml trace elements (trace elements per liter: 0.96 g citric acid, 0.25 g $CoCl2*6H2O$, 1.5 g $MnCl_2*4H_2O$, 0.15 g $CuCl_2*2H_2O$, 1.5 g $H_3BO_3$, 0.25 g $Na_2MoO_4*2H_2O$, 1.3 g $Zn(CH_3COO)2*2H_2O$), 0.01 g thiamine, 5 g glucose, 3 g yeast extract.

A solution of glycerol (~1.2 kg per 10 L fermentation) sterilized in an autoclave was given as a feed and the following components, previously filtered with 0.2 µm filters, were then added per liter of feed: 2 g $Na_2HPO_4*2H_2O$, 3 g $KH_2PO_4$, 5.4 g $K2HPO4$, 3.8 g citric acid, 4 g $(NH4)_2SO_4$, 9 g $MgSO_4*7H_2O$, 0.047 g $CaCl_2$, 1 ml $FeCl_2$ (solution 0.2M), 2 ml trace elements (trace elements per liter: 0.96 g citric acid, 0.25 g $CoCl_2*6H_2O$, 1.5 g $MnCl_2*4H_2O$, 0.15 g $CuCl_2*2H_2O$, 1.5 g $H_3BO_3$, 0.25 g $Na_2MoO_4*2H_2O$, 1.3 g $Zn(CH_3COO)2*2H_2O$) and 0.01 g thiamine. The feed is given 6 hours after inoculation until the nineteenth hour with an exponential ratio of addition. The choice to use glycerol as a carbon source is due to the fact that the expression cells of E. coli used generate acetic acid (acetate) as an undesired by-product that has numerous adverse effects on the production of recombinant proteins [14]. In particular, the cells of E. coli produce acetic acid as an extracellular co-product of the aerobic fermentation, the rate of formation of acetate is directly related to the rate at which the cells grow or to the rate at which they consume the solid substrate as a carbon source, glucose. In common fed-batch fermentation systems, the growth rate of the culture is determined by the speed of feeding of the "glucose" limiting nutrient resulting in cell growth above the threshold which leads to a consequent production of acetate and thus to a reduction of expression of recombinant proteins.

In this invention, various strategies have been developed to limit the accumulation of acetate in order to reduce the negative effects and increase the productivity of the recombinant protein. A strategy that has allowed us to obtain excellent results was to use glycerol as a carbon source. Glycerol, unlike glucose, is not fermented to acetic acid. The results obtained showed that the use of glycerol, rather than glucose, in the fed-batch fermentation process developed in this invention has improved the yield of the soluble recombinant protein hyaluronidase of about 2-3 times [15]. Moreover, unlike glucose which has an inhibitory effect on the promoter that regulates the synthesis of the recombinant protein of this invention, the glycerol can be given to fermentation also after induction with IPTG, allowing the reduction not only of the formation of acetate but also the increase of the soluble formation of recombinant hyaluronidase. Furthermore, the low cost of glycerol compared with glucose makes it preferential as a carbon source for the fermentation of E. coli, in the industrial field.

After induction with Isopropyl β-D-1-thiogalactopyranoside (IPTG), 1 mM final solution, the feed is administered to the culture every hour and in the same amount as the last addition for 5 hours. The induction started 24 hours after inoculation and continued for 12 hours. The fermentation parameters developed are as follows: temperature 37° C., agitation 600 rpm, air flow 5-10 liters air per minute and head pressure of about 0.8 bar.

The bacterial cells are harvested after the induction period of 12 hours by centrifugation at 7500 rpm for 25 minutes. After collection, the bacterial cells are stored at −80° C., ready to be used for the extraction and purification of the recombinant hyaluronidase. The recombinant protein expressed by E. coli, in the different fermentation parameters, is analyzed by electrophoresis run in SDS-PAGE (12%) after staining with Coomassie Brilliant Blue G-250 (BIO-RAD, 161-0406), while the enzyme activity is analyzed by turbidimetric assay [16].

The cells of E. coli BL21 (DE3) transformed with the vector pHyal_sk are induced to express the soluble heterologous protein in the periplasm, in the fermenter with 10 L of medium. In SDS-PAGE, the recombinant expressed had a molecular weight of about 24 kDa and an amount of protein expressed in the periplasm of about 0.4 g/L of culture, the maximum quantity reached after 6 hours of induction with 1 mM IPTG at 37° C. (FIG. 14). The cells of E. coli BL21 (DE3) transformed with the vector pHyal_sk_SL are induced to express the soluble heterologous protein in the periplasm, in the fermenter with 10 L of medium. The periplasmic soluble portion turned out to be present at a concentration of about 1.2 g/L culture, with an enzymatic activity greater than 48000 U/ml culture. In SDS-PAGE, the recombinant expressed had a molecular weight of about 24 kDa, constituting about 16-18% of the total bacterial proteins, after induction with 1 mM IPTG at the twelfth hour at 37° C. (FIG. 15).

EXAMPLE 15: FEDBATCH FERMENTATION OF E. COLI BL21 (DE3) TRANSFORMED WITH THE VECTOR PHYAL_SK_SL ON 20 L MEDIUM

Briefly, the cells of E. coli BL21 (DE3) transformed with the vector pHyal_sk_SL are induced to express the soluble heterologous protein in the periplasm, in the fermenter with 20 L of medium. The periplasmic soluble portion was found to be present at a concentration of about 2 g/L of culture (Table 2) with an enzymatic activity greater than 87000 U/ml culture ($7.5 \times 10^{7-8}$, $7 \times 10^7$ IU/l of culture), approximately 670-750 times higher compared to the autologous hyaluronidase produced in the fermenter as described in the above patent [9]. In SDS-PAGE, the expressed recombinant had a molecular weight of about 24 kDa, constituting about 16-18% of the total bacterial proteins, after induction with 1 mM IPTG at the twelfth hour at 37° C.

The stability of the plasmid during the fermentation phase, for all clones tested with the fed-batch method, was 100% (Table 2). The stability of the plasmid is monitored until the end of the fermentation by screening with the replica plating technique [29] which allows replication of the colonies on plates containing the antibiotic.

Finally, clones genetically engineered in a different way, were tested for their capacity to produce, in the fermenter, the recombinant hyaluronidase encoded by the gene isolated according to this invention. The results are summarised in Table 1.

EXAMPLE 16: ANALYSIS OF RECOMBINANT HYALURONIDASE ACTIVITY IN THE FERMENTATION BROTH

From 0.1 ml of culture from specific induction times or from the final product, the pellet was obtained after centrifugation at 7500 RPM centrifuge (Eppendorf centrifuge 5402, rotor F-45-18-11) for 10 minutes. The cell pellet was resuspended in 500 μl of B-PER Bacterial Protein Extraction Reagent (PIERCE) and mixed by vortexing (Heidolph Reax top) at maximum speed for about 1 minute or until complete resuspension of the pellet. The suitably resuspended pellet was centrifuged at 13000 RPM for 10 minutes to separate the soluble proteins from insoluble proteins. The collected supernatant (soluble proteins) was tested for the presence of hyaluronidase activity using the turbidimetric method described by Di Ferrante [16] modified for analysis on 96-well plates. Briefly, for single well, 31 μl of incubation buffer [17], 8 μl of BSA (0.2 mg/ml), 8 μl of hyaluronic acid (2 mg/ml), 13 μl of $H_2O$ and 10 μl of the supernatant (soluble proteins) diluted 10, 100 and 1000 times with 1×PBS (Sigma-P4417), were set up. The plate is incubated at 37° C. for an hour. After one hour of incubation, 200 μl of CTAB alkaline solution (2.5% (w/v) in 0.5 M NaOH) were added to each well to precipitate the undigested hyaluronic acid and the plate is incubated for 20 minutes at room temperature. The extent of precipitation was measured at an optical density of 640 nm.

Subsequently, the activity per ml of recombinant protein in the culture broth was obtained using the following calculation: activity of ml obtained from the test/2×dilution factor×10=activity on ml of product from fermentation.

A Hyaluronidase standard (FIP) was used to construct a standard curve and the activity of the recombinant hyaluronidase in the periplasmic portion was calculated using this curve.

EXAMPLE 17: LARGE-SCALE EXTRACTION OF THE SOLUBLE FRACTION

From pellet stored at −80° C. (deriving from the fermentation of E. coli BL21(DE3) transformed with the pHyal_sk_SL vector) an amount equivalent to 0.6 liters of fermentation product (approximately equivalent to the range of 80-90 g cell pellet, reflecting approximately a production of 1-1.2 g/L recombinant hyalurodinase) is placed to equilibrate for 45 minutes at room temperature. First method: Once equilibrated, the pellet was treated with 210 ml fresh solution (5° C.) for the dispersion of pellet (205.2 g/L glucose, 5.6 g/L EDTA). The pellet is resuspended, with the dispersion solution, under magnetic stirring for 15 minutes at room temperature and subsequently for about 1 hour at 5° C., using a magnetic stirrer Heidolph type MR2002 at a speed of 500 rpm. After about 1 hour the resuspended pellet is added cold in a 4.5 L solution for osmotic shock (1.2 g/L TRIS, 4 ml/L HCl 2N, 0.1 g/L MgCl2) for the extraction of the periplasmic protein. The mixture obtained is stirred for 4 hours at 4° C., using a magnetic stirrer Heidolph type MR2002 at a speed of 500 rpm.

After the osmotic shock step, the product obtained containing the dispersed E. coli cells was centrifuged at 5° C. for 45 minutes at speeds of about 7500 rpm using a Sorval Evolution Rc centrifuge with SLC-6000 rotor. After centrifugation, the supernatant is collected while the pellet is eliminated. At this point, the supernatant was homogenized using the "Ultra Turrax" system with speed level 2 for 15 seconds.

The supernatant, after treatment with "Ultra Turrax", was brought to pH 8 and filtered by gravity with 0.65 μm filters. After filtration, the concentration of Tris in the filtrate was brought from 10 mM to 50 mM with a 3M Tris-HCl solution and later brought to pH 8. The concentration of the extracted hyaluronidase was assessed in SDS-PAGE and found to be of about 750-850 mg/total (22-24% of total periplasmatic proteins). The activity of the extracted recombinant hyaluronidase is instead assessed by Dorfman's turbidimetric method.

Second method: Once equilibrated, the pellet was treated with the 500 ml B-PER Bacterial Protein Extraction Reagent (PIERCE) solution for the release of the periplasmatic proteins in the medium. The pellet is resuspended, with the B-PER solution, under magnetic stirring for 30 minutes at room temperature and subsequently for further 30 minutes at 5° C., using a magnetic stirrer Heidolph type MR2002 at a speed of 1000 rpm. After about 1 hour the resuspended pellet is centrifuged at 5° C. for 45 minutes at a speed of about 11,000 rpm using a Sorval Rc-5B centrifuge with Sorvall rotor. After centrifugation, the resulting supernatant was added cold in a 5 L 50 mM Tris-HCl solution, pH 8. The solution obtained is stirred for 10 minutes at 4° C., using a magnetic stirrer Heidolph type MR2002 at a speed of 200 rpm. After stirring, the solution was homogenized using the "Ultra Turrax" system with speed level 2 for 15 seconds. The supernatant, after treatment with "Ultra Turrax", was brought to pH 8 and filtered by gravity with 0.65 μm filters. The concentration of the extracted hyaluronidase was assessed in SDS-PAGE and found to be of about 0.9-1.1 g/total (16%-18% of total periplasmic proteins). The activity of the extracted recombinant hyaluronidase is instead assessed by Dorfman's turbidimetric method.

EXAMPLE 18: RECOMBINANT PURIFICATION

The resins and the chromatographic columns were purchased from GE Healthcare Life Sciences and maintained according to the manufacturer's specifications. The balance and elution steps were carried out with a Fast Performance Liquid Chromatography (FPLC; AKTA explorer 100, GE Healthcare) system at a flow of 40-50 ml/min for all 3 chromatographies. At the end of each chromatographic step the hyaluronidase activity was controlled with the modified Dorfman's assay described [9]. Once the soluble fraction is extracted from the periplasmic portion, it is loaded on the first strong ion-exchange chromatography. Strong ion-exchange chromatography (Q sepharose XL): The filtered extract brought to 50 mM Tris-HCl and pH 8 was loaded on 500 ml-600 ml Q sepharose XL resin (GE Healthcare) packed in a XK-50 (GE Healthcare) column and equilibrated with 8 bed volumes (BVs) of Tris-HCl buffer at pH 8. After loading, the column was washed, first with 3 BVs of the same buffer and subsequently with 8 BVs of Tris-HCl buffer at pH 8 with 40 mM NaCl, then the bound proteins were eluted with 5 BVs of a Tris-HCl buffer solution at pH 8 with 110 mM NaCl. The eluted proteins were collected in a single fraction having a volume of about 950 ml and subjected to hyaluronidase activity assay.

Diafiltration and Weak Ion-Exchange Chromatography (CM-Sepharose® Fast Flow):

The fraction obtained is concentrated to 100 ml using the tangential ultrafiltration Labscale TFF System (Millipore) and using Polyethersulfone (PES) filters with cut-off comprised between 3 and 8 kDA, preferably of 5 kDa. After concentration, the sample is diluted 10 times with 50 mM sodium acetate buffer at pH 4. The fraction thus obtained was loaded on 300 ml-400 ml CM-Sepharose® Fast Flow resin (GE Healthcare), packed on a XK-50 column (GE Healthcare) and equilibrated with 6 bed volumes (BVs) of 50 mM sodium acetate buffer at pH 4.0. After loading (preferably at a temperature of 4-5° C.), the column was washed with 3 BVs of the same buffer, then the bound proteins were eluted with 8 BVs of a 50 mM sodium acetate buffer solution at pH 4.5. The eluted proteins were collected in a single fraction having a volume of about 380 ml and subjected to hyaluronidase activity assay. Diafiltration and aromatic hydrophobic interaction chromatography (Phenyl-Sepharose HP).

The fraction obtained and positive to the enzymatic dosage is concentrated to 100 ml using the tangential ultrafiltration Labscale TFF System (Millipore) and using Polyethersulfone (PES) filters with cut-off comprised between 3 and 8 kDA, preferably of 5 kDa. After concentration, the sample is diluted 10 times with 50 mM sodium phosphate buffer with 1.5M ammonium sulphate, pH 7. The fraction thus obtained was loaded on 300 ml-400 ml Phenyl-Sepharose HP resin (GE Healthcare), packed on a XK-50 column (GE Healthcare) and balanced with 8 bed volumes (BVs) of 50 mM sodium phosphate buffer with 1.5M ammonium sulphate, pH 7. After loading, the column was washed with 3 BVs of the same buffer, then the bound proteins were eluted with 5 BVs of a 50 mM sodium phosphate buffer solution with 0.8M ammonium sulphate, pH 7. The eluted proteins were collected in a single fraction having a volume of about 730 ml and subjected to hyaluronidase activity assay. After the enzymatic activity assay, the eluted fraction was subjected to ultrafiltration and dialysis with 10 volume 1×PBS (SIGMA-P4417), using Polyethersulfone (PES) filters with cut-off comprised between 3 and 8 kDA, preferably of 5 kDa, brought to a concentration of about 1 mg/ml and filtered with 0.2 µm filters (protein concentration is determined by BCA Protein Assay Reagent Kit, PIERCE). During the purification steps to obtain a good recovery of the purified product, the recombinant portion is loaded on the chromatographic columns with a maximum ratio of 1.5 mg hyaluronidase per ml of resin. All the eluted protein fractions, both those enzymatically active and those inactive or poorly active, were then analyzed by SDS-PAGE at 12% and then stained with silver stain according to the manufacturer's instructions; in all the fractions having hyaluronidase activity there was a marked protein band of about 24 kDa (FIG. 16). In the different steps of purification, the protein concentration of the recombinant portion was estimated as previously described in SDS-PAGE (12%) and found to be of total 0.45-0.5 g/L in the first chromatography (Q sepharose XL), total 0.45-0.50 g/L in the second chromatography (CM-Sepharose® Fast Flow), total 0.4-0.45 g/L in the third chromatography (Phenyl-Sepharose HP) and total 0.35-0.4 g/L after DIA-filtration. At the end of the purification process applied on about 1 L of fermentation product, about 600-650 mg (Enzymatic activity greater than $2.6 \times 10^7$ U/L purified fermentation product) of recombinant hyaluronidase (Table 3) were obtained.

EXAMPLE 19: ANALYSIS AND CHARACTERIZATION DETERMINATION OF HYALURONIDASE ACTIVITY

The hyaluronidase activity was measured with the modified Dorfman's method [10]. Briefly, the product obtained by the different steps of the process was diluted in 0.03M phosphate buffer, 0.82% NaCl, pH 6.3 and 1 ml of the thus obtained solution was mixed with 1 ml substrate buffer (0.03M phosphate buffer, NaCl 10.82%, pH 6.3) containing 0.5 mg hyaluronic acid. The enzymatic digestion was carried out at 37° C. for 30 minutes and at the end of the incubation process, turbidity was generated by adding a 4 ml horse serum-based acidic solution (SIGMA). The optical density at 640 nm was measured exactly 30 minutes after the addition of the horse serum acidic solution. A standard of hyaluronidase from mammal testicles (EDQM, FIP Hyaluronidase, H1115000) containing 328 IU/mg was used to construct a standard curve and the activity (in units) of the samples was calculated using this curve.

SDS-PAGE Electrophoresis

The electrophoretic assays on polyacrylamide gel in the presence of sodium dodecyl sulfate (SDS-PAGE) were carried out using Laemmli's method [11] on 12% polyacrylamide gel, using a Mini-PROTEAN 3 (BIO-RAD) according to the manufacturer's instructions. The concentration and the molecular weight of the hyaluronidase in the fermentation product and in different purification steps were estimated by comparison with standard low molecular weight proteins (GE Healthcare).

The polyacrylamide gels suitably stained with Coomassie (BIO_RAD) after the electrophoretic run, were acquired by a laboratory image capturing device ImageQuant™ 300 TL (GE Healthcare), while (quantitative and qualitative) assays were performed using the image analysis software ImageQuant TL (GE Healthcare).

N-Terminal End Sequencing

The N-terminal amino acid sequencing was carried out according to Edman's degradation method using an automated protein sequencer in pulsed liquid phase (ABI-Perkin Elmer Mod. 477A). BLAST software [18] was used to conduct homology research in the GenBank database and in that of the human genome project of the *Streptomyces* species available on the web. The fractions, obtained by the purifications of the *E. coli* strain transformed with the pHyal_sk vector and the *E. coli* strain transformed with the pHyal_sk_SL vector according to the invention, were subjected to SDS-PAGE electrophoresis on 12% gel, as described above, then to blotting on polyvinylidene difluoride membrane (BIO-RAD) and stained according to the manufacturer's instructions. The band relating to hyaluronidase for both productions was separated with a scalpel, trying to obtain a piece as small-sized as possible (3 mm×10 mm) and was loaded in the reaction chamber of the sequencer.

The sequencing of the N-terminal end, conducted as described hereinbefore, allows to determine that the two recombinant hyaluronidases produced and coming from two used different genetic engineering and expression systems, contain differences in the N-terminal amino acid sequence. In case of *E. coli* sample transformed with the pHyal_sk_SL vector according to the invention, the assay provided chromatograms in which a single N-terminal amino acid sequence was significantly present, allowing to reconstruct the test sequence reported hereinafter: AGENGA (SEQ ID NO: 42). The above-mentioned experimentally determined sequence corresponds to the N-terminus of the protein isolated in its autologous form described by [9] free from methionine at position 1. In case of the *E. coli* sample transformed with the pHyal_sk vector according to the invention, the assay instead detected the presence of at least two N-terminal amino acid sequences, reported hereinafter is the listing of the N-terminal amino acids detected by the sequencing: Most represented sequence MAGENGA (SEQ ID NO: 43) which corresponds to the N-terminus of the mature protein with methionine at position 1, and a less represented sequence AQPAMAMAGENGA (SEQ ID NO: 44) which corresponds to the partially mature protein (contains sequence AQPAMAM (SEQ ID NO: 45) belonging to the signal peptide apparently not totally deprived of the protein by the cell system). Comparison of hyaluronidase activity between the heterologous and autologous form.

The enzymatic potential of the hyaluronidase according to the invention (*E. coli* transformed with the pHyal_sk_SL vector) was assessed by comparison with the enzymatic activity of the autologous hyaluronidase [9], using the enzymatic assay described [9] and the activity value is reported to be in both cases greater than $4 \times 10^4$ IU/mg (the protein concentration was determined by BCA Protein Assay Reagent Kit, PIERCE).

The result of this assay shows that hyaluronidase according to the invention, in particular of the form coming from the *E. coli* strain engineered with the pHyal_sk_SL plasmid, has the same activity as the autologous form. However, by means of the production and purification methods described in the invention it was possible to accurately assess the value of the enzymatic activity of the recombinant hyaluronidase according to the invention, which was found to be greater than 40,000 U/mg protein.

UV spectra analysis and comparison of spectra of circular Dichroism of the heterologous and the autologous forms.

Circular dichroism (CD) experiments: Spectra at the Far-UV circular dichroism were collected at room temperature on a Jasco spectropolarimeter J-715 model, with quartz cell having path length of 1 millimeter. Other test settings were: scan speed, 10 nm/min, sensitivity, 50 MDEG, time constant, 16 s, bandwidth, 3 nm. The circular dichroism measurements were conducted on protein solutions (autologous hyaluronidase, recombinant hyaluronidase according to the invention) at concentration of $2.10^{-6}$ M. All the samples were diluted at a final concentration of $2.10^{-6}$ M using ultra-pure water. The CD spectra were collected at 260-195 nm blank corrected and adjusted for dilution.

The circular dichroism spectra are reported in FIG. 17. The overlay files match: the lower line corresponds to the autologous hyaluronidase [9] and the upper one corresponds to the heterologous hyaluronidase according to the invention. The two spectra have a superposable profile, confirming the same structure for both the samples (FIG. 17-a). The small difference which is noted may be attributed to the not perfect coincidence of the concentrations of the two solutions.

From the UV spectra, the recombinant hyaluronidase sample does not show aggregation. From this study it may be inferred that the preparation according to the invention has a secondary structure very similar to that of the autologous hyaluronidase [9] and that the protein produced according to the present invention does not show aggregation (FIG. 17-b).

Mass Spectrometry

The mass spectrometry assays for determining the molecular weight were conducted using Quattro micro mass spectrometer (Waters), while the assay of peptide mapping to confirm the identity of the primary structure of the recombinant portion was carried out using the accurate mass values of the peptides determined by means of the MALDI-MS Voyager DE-PRO system (Applied Biosystems, Firmingham Mass., USA) after separation in RP-HPLC.

The fraction obtained after purification of recombinant hyaluronidase according to the invention was subjected to digestion with trypsin, after separation in RP-HPLC, the peptide mixture produced for each sample was analyzed by MALDI-MS in reflector mode. The study and interpretation of the MALDI spectra acquired therefore respectively allowed verifying 97% identity of the primary structure of the reference amino acid sequence [9] and over 94% identity of the primary structure of the theoretical amino acid sequence according to the invention (peptide sequence predicted by http://web.expasy.org/translate/) with the amino acid sequence of the sample produced according to the invention (SEQ ID NO: 21).

Furthermore, the fraction obtained after purification of the recombinant hyaluronidase according to the invention was subjected to determination of molecular weight of the protein by means of mass spectrometry and the result of the assay is reported in FIG. 18.

Isoelectric Focusing

The protein fraction to be analyzed (recombinant hyaluronidase obtained according to the invention) is mixed in a suitable loading buffer and loaded onto IPG strips at pH 3-10 (ReadyStrips 7 cm, BIO-RAD); incubation is performed at 25° C. until absorption of the sample and the strip is loaded onto the PROTEAN IEF Cell (BIO-RAD) for isoelectric focusing (IEF). At the end of the isoelectric focusing run the strip is stained with IEF Gel Staining solution (BIO-RAD) for 45 minutes and then destained with Destain solution (BIO-RAD). The destained IPG strips were acquired by a laboratory image capturing device ImageQuant 300 TL (GE Healthcare) while (quantitative and qualitative) assays were performed using the image analysis software ImageQuant TL (GE Healthcare).

The isoelectric point of the sample was determined by comparison with the isoelectric points of the reference standards (IEF Marker pH 3-10, SERVA). The result of the assay is reported in FIG. 19.

Characterization by capillary electrophoresis of the recombinant hyaluronidase and determination of the molar extinction coefficient.

The qualitative-quantitative assay of the protein fraction to be analyzed (recombinant hyaluronidase obtained according to the invention) was performed by BIOTEKNET (Napoli, Italy) by means of capillary electrophoresis with a P/ACE MDQ Beckman-Coulter instrument equipped with diode-array detector and UV lamp, using a capillary of fused silica (50 cm actual length, 60.2 cm total length, 50 µm inner diameter) and a 20 mM sodium citrate buffer, at pH 2.5, applying an e.p.d. of 25 kV (ensuring a greater stability in the electrophoretic separation process and of the current used) for 15 min and detecting the absorption at 200 nm. Before proceeding with the sample assay, the BSA (bovine serum albumin) was suitably analyzed at three different concentrations (1 mg/mL; 0.8 mg/mL; 0.4 mg/mL), using the above-mentioned method and thereby obtaining a calibration straight line. The assay was carried out on the same sample twice diluted (FIG. 20). In both electropherograms it is possible to identify the presence of a single peak (Purity 100%) having migration time of 7.7±0.9 min and the protein quantification, although affected by a calibration with external standard (BSA), therefore not with the same protein, returns a high purity, and a quantification superimposable to the expected one (~1 mg/ml). The research work on the determination of the molar extinction coefficient of the recombinant hyaluronidase may be divided into four experimental moments: 1. Densitometric assay of the hyaluronidase samples of the invention, 2. Spectrophotometric assay of the hyaluronidase samples of the invention, 3. Identification of theoretical absorbance, 4. Identification of the molar extinction coefficient.

At this point, once collected the information in the preceding steps, the Beer-Lambert law is applied: $A = el*l*C$ where el is referred to as molar absorption coefficient, C is the molar concentration of the solution and l is the optical path. Based on this formula and on our obtained information, the molar absorption coefficient, at a wavelength of 280 nm, is as follows: 12383 $L*mol^{-1}*cm^{-1}$ Abs 0.1%(=1 g/L) 0.570 (Molar extinction coefficient of hyaluronidase produced according to the present invention).

HPLC Assay by Means of Gel Filtration

For the assays by means of gel filtration the LC-10AD HPLC instrument (SHIMADZU) was used with a Bio-Sil SEC column (BIO-RAD), eluting with 0.05M $NaH_2PO_4$, 0.05M $Na_2HPO_4$, 0.15M NaCl, pH 6.6, at 1 ml/min. The absorption wavelength used was 214 nm (SPD-10A, SHIMADZU). The purity of the protein was determined using the software LC solution 1:21 SP1. The fraction obtained after purification of recombinant hyaluronidase as described in the invention was subjected to gel filtration column HPLC as described above. The result of the assay on purity of the recombinant portion is reported by the chromatogram in FIG. 21-a and is of 100%.

Determination of the level of purity by means of RP-HPLC. For the purity assays by means of Reversed-Phase HPLC the LC-10AD HPLC instrument (SHIMADZU) was used with a Vydac 214ATP54 C4 (Grace Davison Discovery Sciences) column, eluting with 50 mM Tris pH 7.5 with 1-propanol, at 0.5 ml/min. The absorption wavelength used was 220 nm (SPD-10A, SHIMADZU). The purity of the protein was determined using the software LC solution 1:21 SP1. The fraction obtained after purification of the recombinant hyaluronidase as described by the invention was subjected to RP-HPLC on a (reversed) hydrophobic-phase column as described above. The result of the assay on purity of the recombinant portion is reported by the chromatogram in FIG. 21-b and is very close to 100%.

Characterization of the bacterial recombinant hyaluronidase by means of electrophoresis on polyacrylamide gel.

The electrophoretic assays on polyacrylamide gel in the presence of sodium dodecyl sulfate (SDS-PAGE) were carried out using Laemmli's method [11] on 12% polyacrylamide gel, using a Mini-PROTEAN 3 (BIO-RAD) according to the manufacturer's instructions. The concentration and the molecular weight of the hyaluronidase in the fermentation product and in different purification steps were estimated by comparison with standard low molecular weight proteins (GE Healthcare).

The polyacrylamide gels, suitably stained with Coomassie (BIO_RAD) after the electrophoretic run, were acquired by a laboratory image capturing device ImageQuant 300 TL (GE Healthcare), while (quantitative and qualitative) assays were performed using the image analysis software ImageQuant TL (GE Healthcare).

On the other hand, for the Western Blot assay, the proteins were fractioned in SDS-PAGE at 12% and transferred to nitrocellulose membranes. The proteins of interest were then identified by incubation with a 1:2000 dilution of anti-hyaluronidase antibody (Abnova) in 10% dry milk/PBS for 12 hours, and the specific reaction was highlighted by means of the addition for 1 hour of mouse anti-IgGs secondary antibodies conjugated with alkaline phosphatase, followed by detection with the BCIP/NBT substrate (BUF045A, SEROTEC).

The production of recombinant hyaluronidase according to the invention from *E. coli* BL21(DE3) engineered cells and therefore without the presence of animal derivatives allowed producing the protein with a high specific enzymatic activity (>40000 Units/mg of protein). The recombinant protein produced according to the invention had a level of purity 100 times higher than that of the hyaluronidase standard from mammal testicles (EDQM, FIP Hyaluronidase, H1115000) as shown in FIG. 22. While recombinant hyaluronidase purified according to the invention after migration on 12% SDS-PAGE gel and GelMate Blue (Euro-Clone) coomassie staining had a single band, the bovine hyaluronidase, available on the market, showed several impurities. A smaller band (at about 75-80 kDa) in the smear of proteins of the bovine hyaluronidase reacted with an anti-hyaluronidase polyclonal antibody (Abnova) by Western Blotting, confirming that enzyme hyaluronidase is a smaller component of hyaluronidase preparations derived from animals (FIG. 22).

Endotoxin Detection

The Limulus Amebocyte Lysate Test (LAL), which uses the reagent prepared from blood of limulus Poliphemus, showed to be the most sensitive and specific test to detect and measure the level of bacterial endotoxins in raw materials used in the production and for the "in-process" monitoring of endotoxin levels. Endotoxins, more commonly known as pyrogens, cause from fever to irreversible shock, from difficulties in blood and tissue exchanges to lethal consequences.

With the recombinant hyaluronidase being produced according to the invention in *E. coli* cells, it was essential to assess the level of endotoxins in the final product. To this end, we used the method of "Chromo-LAL", a kinetic chromogenic test for the quantitative detection of endotoxins produced by Gram-negative bacteria.

Briefly, in the "Chromo LAL (art 32427, PBI S.p.A—Italy)" test, the lysate and the chromogenic reagent substrate co-freeze-dried were mixed with the hyaluronidase sample (produced according to the invention) in a multiwell microplate (96 wells) and incubated at 37±1° C. in a suitable reader (ELX 808 IU, BioTek). The absorbance values read were collected and analyzed by a dedicated software. The time required for hyaluronidase sample to reach a specific absorbance value (optical density) was calculated. Furthermore, a standard calibration curve (CSE, lot.104, art.17078, PBI S.p.A—Italy) was built which shows the linear correlation between the "start time" log and the log of standard endotoxin concentration. The maximum range between the endotoxin concentrations of the standard curve is 0.005 EU/ml-50 EU/ml. The sensitivity [19] of the test was defined from the lowest concentration of endotoxin used to build the standard curve. The maximum sensitivity of this test is 0.005 EU/ml.

The endotoxin concentration for the corresponding "start time" of the hyaluronidase sample was read from the standard curve which is a log-log diagram deriving from the scores obtained calculating the "start times" versus standard concentrations.

At the end, the estimated value of endotoxins in the hyaluronidase sample produced according to the invention was calculated by the Gen5 software (BioTek) resulting to be very low, that is lower than 0.5 endotoxin units per milligram of recombinant hyaluronidase (Table 4). Determination of proteins and DNA deriving from host cells.

As regards the determination of proteins deriving from *E. coli* host cells used for the heterologous expression of recombinant hyaluronidase (as described by the present invention) the ELISA method was used, in particular, the Enzyme Immuno Assay kit "*E. coli* HCP" from *Cygnus* technologies (F010). The assay is based on the sandwiched use of affinity-purified antibodies directed to a mixture of 6 *E. coli* strains commonly used for cloning and expression of recombinant proteins.

The test was performed according to the manufacturer's instructions, on the purified sample of recombinant hyaluronidase, the concentration of proteins deriving from *E. coli* (host strain) is directly proportional to the development of color caused by enzymatic reaction of alkaline phosphatase conjugated to the antibody.

The concentration of proteins deriving from the host strain towards the standard concentrations was estimated (calculation and calibration of the curve were performed by the GEN 5 software, BioTek) in the sample of hyaluronidase produced according to the invention to be lower than 10 ppm as shown in Table 4 (the limit approved by the competent authorities is below 100 ppm).

On the other hand, the determination of the quantity of DNA from the host strain of *E. coli* was carried out in the sample of recombinant hyaluronidase (produced according to the invention), using the DNA Threshold method. This assay was performed at the Charles River Biopharmaceutical services GmbH laboratories, Germany. The studies indicated with the code M1/F07/12 and M2/F07/12 gave as a final result a very low level of DNA deriving from the cell host, calculated to be lower than 20 pg (the limit approved by the competent authorities is lower than or equal to 300 pg/mg of protein) per milligram of recombinant hyaluronidase (Table 4).

EXAMPLE 20: ASSAY ON AGAROSE GEL OF HYALURONIC ACID DEPOLYMERIZATION

For the in vitro assessment of the capability of recombinant hyaluronidase, produced according to the invention, of depolymerizing hyaluronic acid (Hyalgan®; Fidia S.p.A., Italy) in its primary constituents N-acetylglucosamine and glucuronic acid, the electrophoretic assay method in agarose gel [20] was used after hyaluronic acid is digested with 1 unit of recombinant hyaluronidase within the indicated times from 5 minutes to 24 hours.

Briefly, the hyaluronic acid samples (500 kD-730 kD), after reacting with recombinant hyaluronidase within the indicated times (from 5 minutes to 24 hours) were separated using the Sub-CellGT electrophoresis system (BIO-RAD) and gels with 1% agarose (25 cm in length). The samples were migrated in electrophoresis for about 12 hours at a temperature of about 16° C. with a constant voltage of 50 Volts. Staining is carried out as described in previous studies [20].

The results shown in FIG. 23 indicated that the recombinant hyaluronidase, produced according to the invention, is capable of completely digesting the substrate until reaching undetectable levels of hyaluronic acid before 24 hours.

EXAMPLE 21: STABILITY AGAINST PROTEOLYTIC ENZYMES

Hyaluronidase is an enzyme hydrolyzing hyaluronic acid, therefore increasing the permeability of connective tissue enhancing the diffusion and dispersion of the drug, that is administered locally subcutaneously, in the surrounding tissues.

In some treatments, hyaluronidase is administered in low doses (the typical dose used is 15 units), to reduce the damages caused by the leakage of antibiotics, hyperosmotic solutions, acid or basic solutions, or the correction of hyaluronic acid-based fillers to avoid allergic and anaphylactic reactions. Therefore, it is fundamental for the hyaluronidase to be stable at these doses towards the proteolytic enzymes present in connective tissue, which may easy degrade it once injected, inhibiting its action. In order to test and compare the resistance of recombinant hyaluronidase with respect to the bovine one currently used in the market, against proteolytic enzymes, a turbidimetric model for in vitro assays was provided. Briefly, recombinant hyaluronidase (prepared according to the invention) at the concentration of 10 U (<250 ng) and the bovine hyaluronidase 100 U (300 µg) were treated separately with two different doses of Pronase E (200 µg and 500 µg) in a phosphate buffer solution (pH 7.0) at 37° C. for 1 hour, 24 hours and 48 hours. The residual enzymatic activity (expressed as percentage) of the two concentrations of enzymes treated and not treated with Pronase E was measured according to Dorfman's method as described in the patent. The results obtained are placed in a diagram and shown in FIG. 24.

EXAMPLE 22: EFFECT OF HUMAN AND ANIMAL SERUM ON HYALURONIDASE ACTIVITY

In this invention, thanks to the provision of an in vitro test model using the turbidimetric model, what had already emerged from previous clinical studies was confirmed, that is, enzymatic activity of bovine hyaluronidase (bovine PH20) is inhibited by human and/or animal blood, but it was however found that human and/or animal blood does not inhibit hyaluronidase from recombinant *S. koganeiensis* (FIG. 25). The method used to assess, in this invention, inhibition of hyaluronidase activity by (animal/human) blood was previously described by Albert DORFMAN, et al [21]. Briefly, the two concentrations of recombinant hyaluronidase produced according to the invention (40 units, 400 units), and bovine hyaluronidase (40 units, 400 units), were separately and respectively treated with serum coming from animal blood and serum coming from human blood in a sulphate buffer solution (pH 7.0) mixed with substrate buffer containing 0.5 mg hyaluronic acid. The mixture thus obtained was placed at 37° C. for 30 minutes, 1 hour and 6 hours. The relative enzymatic activity of the two concentrations of enzymes treated with the sera was measured at the end of each established time interval after having generated turbidity by adding a 4 ml horse serum-based acid solution and continuing as per the Dorfman's method previously described. The development of turbidity due to the addition of the serum was corrected by the blank containing all the reagents, except for hyaluronidase.

Therefore, these latter studies show that the recombinant hyaluronidase produced according to the invention, which has a high hyaluronidase activity and high stability versus proteolytic enzymes, is capable of performing, with its maximum bioavailability, the total activity in bloodstream without the possibility of detecting bacterial or viral infections, proving to be effective also for cardio- and cerebro-vascular therapies.

BIBLIOGRAPHIC REFERENCES

[1] L. H. Bookbinder, et al, Journal of Control Release. 2006 Aug. 28; 114(2):230-41. Epub 2006 Jun. 7.
[2] Bratisl Lek Listy 2009; 110(1).
[3] US 2008/0124316 A1.
[4] Acta Med Scand. 1984; 216(2):209-13.
[5] Dorfman A, Ott M L, Whitney R: The hyaluronidase inhibitor of human blood. J Biol Chem 174: 621, 1948.
[6] McClean D: The in-vivo decapsulation of streptococci by hyaluronidase. J Pathol Bacteriol 54: 284, 1942.
[7] US 2011/0053247 A1.
[8] U.S. Pat. No. 4,258,134.
[9] WO 2010/130810 A1.
[10] Dorfman A. 1955.
[11] Laemmli, U. K. 1970.
[12] Sambrook J, Russel D W (2001).
[13] Peter B. Kaufman, William Wu, Donghern Kim, Leland Cseke 1995; Sambrook and Russell (2001).
[14] Sørensen, H. P. and Mortensen, K. K. (2005). Advanced strategies for recombinant protein expression in *Escherichia coli*. J. Biotechnol. 115, 113-128.
[15] Luo, Q. et al. (2006) Optimization of culture on the overproduction of TRAIL in high-cell-density culture by recombinant *Escherichia coli*. Appl. Microbiol. Biotechnol. 71, 184-191.
[16] Di Ferrante 1956.
[17] McIlvaine's buffer, McIlvaine 1921.
[18] Altschul S F, Madden T L, Schaffer A A, Zhang J, Zhang Z, Miller W, Lipman D J. 1997. Gapped BLAST and PSI-BLAST: a new generation of protein database search programs. Nucleic Acids Res. 25:3389-3402.
[19] Ebner, C., D. Kraft, F. Prasch, R. Steiner, and H. Ebner. Type 1 allergy induced by LYMULUS Amebocyte Lysate (LAL). Clinical and Experimental Allergy 22:417-419 (1992).

[20] Lee, H. G., and Cowman, M. K. (1994) Anal. Biochem. 219, 278-287.

[21] Albert DORFMAN, MELVIN L. OTT, e Richard WHITNEY, Febbraio 20, 1948.

[22] Killmann, H., Benz, R., and Braun, V. (1996). Properties of the FhuA channel in the *Escherichia coli* outer membrane after deletion of FhuA portions within and outside the predicted gating loop. J Bacteriol 178, 6913-20.

[23] The *Bacillus subtilis* centred wiki SubtiWiki: A community curated consensual annotation that is continuously updated. SubtiPathways is a model of *B. subtilis* metabolism and regulation in SBML/SBGN (Systems Biology Markup Language/Graphical Notation).

[24] Perkins J D, et al. XbaI and BlnI genomic cleavage maps of *Escherichia coli* K-12 strain MG1655 and comparative analysis of other strains. J. Mol. Biol. 232: 419-445, 1993.

[25] Heath J D, et al. NotI genomic cleavage map of *Escherichia coli* K-12 strain MG1655. J. Bacteriol. 174: 558-567,1992.

[26] Sambrook, J., Fritsch, E. F. and Maniatis, T. (1989). Molecular Cloning: A Laboratory Manual. Cold Spring Harbor Laboratory Press, Cold Spring Harbor, N.Y.

[27] Weiner, M. P., Anderson, C., Jerpseth, B., Wells, S., Johnson-Browne, B. et al. (1994) Strategies 7(2):41-43.

[28] Altschul et al., 1997.

[29] Lederberg, J and Lederberg, E M (1952) Replica plating and indirect selection of bacterial mutants. J Bacteriol. 63: 399-406.

The invention claimed is:

1. Method for the production of hyaluronidase from *Streptomyces* koganeiensis ATCC 31394 comprising the amino acid sequence shown in SEQ. ID. No. 21 comprising the following steps:
   a) inoculating a bacterial culture medium in a bioreactor with a inoculum of recombinant cells that contain at least one vector comprising the sequence shown as SEQ ID No. 41;
   b) subjecting the content of the bioreactor of step a) to fermentation at a pH between 6.7 and 7.1 in the presence of a nourishment solution;
   c) adding an inducer of the lac genes to the mixture of step b);
   d) subjecting the mixture of step c) to an induction period of between 8 and 24 hours;
   e) centrifuging the bacterial cells obtained in step d);
   f) re-suspending the pellets obtained in step e) and subjecting the resulting suspension to osmotic shock;
   g) extracting the periplasmic proteins by centrifugation of the suspension of step f);
   h) purifying the protein fraction having hyaluronidase enzymatic activity obtained in step g) by a sequence of:
   i. strong ion-exchange chromatography and isolation of the hyaluronidase enzymatic activity fraction;
   ii. weak cation-exchange chromatography and isolation of the hyaluronidase enzymatic activity fraction; and
   iii. aromatic hydrophobic interaction chromatography and isolation of the hyaluronidase enzymatic activity fraction.

2. Method according to claim 1, wherein the recombinant cell of step a) is selected from a cell of *Escherichia coli* and one of *Bacillus subtilis*.

3. Method according to claim 1, wherein in step b), a glycerol solution is used as nourishment solution.

4. A method according to claim 1, wherein the hyaluronidase from *Streptomyces* koganeiensis ATCC 31394 is in purified form, comprises the amino acid sequence in SEQ. ID. No. 21, is free from cysteine and has an endotoxin content<0.5 U/mg.

5. A method of formulating a cosmetic or pharmaceutical composition, which comprises
   producing a hyaluronidase using the method according to claim 4; and
   adding excipients and/or diluents suitable for cosmetic or pharmaceutical use to said hyaluronidase,
   thereby obtaining said hyaluronidase formulated in a cosmetic or a pharmaceutical composition.

6. The method according to claim 5, wherein, said cosmetic or pharmaceutical composition contains at least one other active ingredient, and wherein said method further comprises the step of adding said at least one other active principle.

* * * * *